US009669035B2

(12) United States Patent
Megens et al.

(10) Patent No.: US 9,669,035 B2
(45) Date of Patent: Jun. 6, 2017

(54) COMBINATIONS COMPRISING PDE 2 INHIBITORS SUCH AS 1-ARYL-4-METHYL-[1,2,4]TRIAZOLO-[4,3-A]]QUINOXALINE COMPOUNDS AND PDE 10 INHIBITORS FOR USE IN THE TREATMENT OF NEUROLOGICAL OF METABOLIC DISORDERS

(71) Applicant: Janssen Pharmaceutica NV, Beerse (BE)

(72) Inventors: Antonius Adrianus Hendrikus Petrus Megens, Beerse (BE); Xavier Jean Michel Langlois, Beerse (BE); José Ignacio Andrés-Gil, Toledo (ES)

(73) Assignee: JANSSEN PHARMACEUTICA NV, Beerse (BE)

(*) Notice: Subject to any disclaimer, the term of this patent is extended or adjusted under 35 U.S.C. 154(b) by 0 days.

(21) Appl. No.: 14/410,497

(22) PCT Filed: Jun. 25, 2013

(86) PCT No.: PCT/EP2013/063244
§ 371 (c)(1),
(2) Date: Dec. 22, 2014

(87) PCT Pub. No.: WO2014/001314
PCT Pub. Date: Jan. 3, 2014

(65) Prior Publication Data
US 2015/0366873 A1 Dec. 24, 2015

(30) Foreign Application Priority Data
Jun. 26, 2012 (EP) .................... 12173681

(51) Int. Cl.
A61K 31/535 (2006.01)
A61K 31/5377 (2006.01)
A61K 45/06 (2006.01)
A61K 31/4709 (2006.01)
A61K 31/472 (2006.01)
A61K 31/4725 (2006.01)
A61K 31/517 (2006.01)

(52) U.S. Cl.
CPC ........ A61K 31/5377 (2013.01); A61K 31/472 (2013.01); A61K 31/4709 (2013.01); A61K 31/4725 (2013.01); A61K 31/517 (2013.01); A61K 45/06 (2013.01)

(58) Field of Classification Search
CPC .................................................. A61K 31/5377
USPC ...................................................... 514/233.2
See application file for complete search history.

(56) References Cited

U.S. PATENT DOCUMENTS

| 4,242,513 | A | 12/1980 | Hoover et al. |
| 4,713,381 | A | 12/1987 | Ao et al. |
| 5,137,876 | A | 8/1992 | MacCoss et al. |
| 5,317,019 | A | 5/1994 | Bender et al. |
| 5,360,796 | A | 11/1994 | Hansen, Jr. et al. |
| 5,486,525 | A | 1/1996 | Summers, Jr. et al. |
| 5,498,774 | A | 3/1996 | Mitsudera et al. |
| 5,559,106 | A | 9/1996 | Jacobsen et al. |
| 5,683,998 | A | 11/1997 | Shibayama et al. |
| 6,054,587 | A | 4/2000 | Reddy et al. |
| 6,245,769 | B1 | 6/2001 | Arvanitis et al. |
| 6,248,755 | B1 | 6/2001 | Chapman et al. |
| 6,352,990 | B1 | 3/2002 | McCarthy |
| 6,403,588 | B1 | 6/2002 | Hayakawa et al. |
| 6,589,947 | B1 | 7/2003 | Hamanaka et al. |

(Continued)

FOREIGN PATENT DOCUMENTS

| CA | 2398956 A1 | 8/2001 |
| CA | 2668738 A1 | 7/2008 |

(Continued)

OTHER PUBLICATIONS

Andres et al. Bioorganic & Medicinal Chemistry Letters, 23, (2013), 785-790.*
Aggarwal, Journal of Fluorine Chemistry, 130(10), 886-893, (2009).
Aggarwal, Synthetic Communications, 2006, 36, 1873-1878.
Andres J et al., Bioorganic & Medicinal Chemistry Letters,785-790, 2012.
Baratti, Behav Pharmacol, 10, 731-737 (1999).
Domek Lopacinska, Mol Neurobiol, 41(2-3), 129-137, 2010.
Kehler J et al., Expert Opin. Ther.patents, 19, 12, 1715-1725, 2009.
Kumar, Behav Pharmacol, 21(3), 217-230, 2010.
Kumar, Green Chem., 2004, 6, 156-157.
Mennitti, Nature Rev Drug Discovery, 5, 660-669, 2006.
Miller, Angew Chem Int Ed, 47, 8998-9033, 2008.
Prickaerts, Neuroscience, 2002; 113: p. 351-361.

(Continued)

Primary Examiner — Nizal Chandrakumar

(57) ABSTRACT

The present invention relates to combinations of phosphodiesterase 2 (PDE2) inhibitors with inhibitors of phosphodiesterase 10 (PDE10). In particular, the invention relates to combinations of 1-aryl-4-methyl-[1,2,4]triazolo[4,3-a]-quinoxaline derivatives which have been found to inhibit phosphodiesterase 2 (PDE2), with inhibitors of phosphodiesterase 10 (PDE10). Particular PDE10 inhibitors are selected from the group of MP-10, PQ-10, TP-10, papaverine, and the compounds disclosed in WO 2011/051324 and in WO 2011/110545. The invention is also directed to pharmaceutical compositions comprising such combinations, to processes for preparing such compositions, to the use of PDE2 inhibitors, in particular of 1-aryl-4-methyl-[1,2,4]triazolo[4,3-a]-quinoxaline derivatives for the potentiation of said PDE10 inhibitors, and to the use of said PDE10 inhibitors for the potentiation of the effect of said PDE2 inhibitors, in particular, 1-aryl-4-methyl-[1,2,4]triazolo[4,3-a]-quinoxaline derivatives, and to the use of such combinations and compositions for the prevention and treatment of disorders in which PDE2 and PDE10 are involved, such as neurological and psychiatric disorders, and endocrinological or metabolic diseases.

2 Claims, 11 Drawing Sheets

(56) References Cited

U.S. PATENT DOCUMENTS

| | | |
|---|---|---|
| 6,777,395 B2 | 8/2004 | Bhat et al. |
| 6,806,268 B2 | 10/2004 | Gall |
| 6,844,341 B2 | 1/2005 | Thomas |
| 6,855,719 B1 | 2/2005 | Thomas et al. |
| 6,900,217 B2 | 5/2005 | Chen |
| 6,936,617 B2 | 8/2005 | Hutchison et al. |
| 6,992,080 B2 | 1/2006 | Dwyer et al. |
| 6,992,188 B1 | 1/2006 | Chen |
| 7,074,801 B1 | 7/2006 | Yoshida et al. |
| 7,078,405 B2 | 7/2006 | Hibi et al. |
| 7,078,410 B2 | 7/2006 | Berg et al. |
| 7,105,533 B2 | 9/2006 | Campbell et al. |
| 7,132,426 B2 | 11/2006 | Jones et al. |
| 7,148,353 B2 | 12/2006 | Fang et al. |
| 7,186,714 B2 | 3/2007 | Gudmundsson et al. |
| 7,186,740 B2 | 3/2007 | Paruch et al. |
| 7,186,832 B2 | 3/2007 | Sun et al. |
| 7,189,723 B2 | 3/2007 | Mitchell et al. |
| 7,196,095 B2 | 3/2007 | Biftu et al. |
| 7,244,740 B2 | 7/2007 | Gudmundsson et al. |
| 7,259,164 B2 | 8/2007 | Mitchell et al. |
| 7,306,631 B2 | 12/2007 | Glenn, Jr. et al. |
| 7,312,341 B2 | 12/2007 | DeSimone et al. |
| 7,320,995 B2 | 1/2008 | Bonjouklian et al. |
| 7,348,359 B2 | 3/2008 | Gardinier et al. |
| 7,393,848 B2 | 7/2008 | Currie et al. |
| 7,405,295 B2 | 7/2008 | Currie et al. |
| 7,417,041 B2 | 8/2008 | Blumberg et al. |
| 7,491,716 B2 | 2/2009 | Engler |
| 7,504,404 B2 | 3/2009 | McArthur et al. |
| 7,511,040 B2 | 3/2009 | Belanger et al. |
| 7,557,103 B2 | 7/2009 | Collins et al. |
| 7,563,797 B2 | 7/2009 | Araldi et al. |
| 7,572,807 B2 | 8/2009 | Li et al. |
| 7,576,085 B2 | 8/2009 | Guzi et al. |
| 7,622,584 B2 | 11/2009 | Kim et al. |
| 7,666,880 B2 | 2/2010 | Lee et al. |
| 7,674,801 B2 | 3/2010 | Basarab et al. |
| 8,716,282 B2 | 5/2014 | Pastor-Fernandez et al. |
| 8,859,543 B2 | 10/2014 | Bartolome-Nebreda et al. |
| 2001/0041673 A1 | 11/2001 | Fossa |
| 2002/0049208 A1 | 4/2002 | Bakthavatchalam et al. |
| 2003/0027820 A1 | 2/2003 | Gall |
| 2004/0014957 A1 | 1/2004 | Eldrup et al. |
| 2004/0058938 A1 | 3/2004 | Cullmann et al. |
| 2005/0031588 A1 | 2/2005 | Sommadossi et al. |
| 2005/0079176 A1 | 4/2005 | Pierson III et al. |
| 2005/0079387 A1 | 4/2005 | Lee et al. |
| 2005/0165232 A1 | 7/2005 | Beresis et al. |
| 2005/0234029 A1 | 10/2005 | Dodic et al. |
| 2005/0245520 A1 | 11/2005 | Dodic et al. |
| 2005/0288295 A1 | 12/2005 | Currie et al. |
| 2006/0094699 A1 | 5/2006 | Kampen et al. |
| 2006/0100235 A1 | 5/2006 | Andersen et al. |
| 2006/0135517 A1 | 6/2006 | Lee et al. |
| 2006/0154105 A1 | 7/2006 | Yamamoto et al. |
| 2006/0178367 A1 | 8/2006 | Currie et al. |
| 2006/0258722 A1 | 11/2006 | Yasuma et al. |
| 2007/0004736 A1 | 1/2007 | Kubo et al. |
| 2007/0049591 A1 | 3/2007 | Pinkerton et al. |
| 2007/0078136 A1 | 4/2007 | Vaccaro et al. |
| 2007/0099925 A1 | 5/2007 | Calderwood et al. |
| 2007/0105864 A1 | 5/2007 | Guzi et al. |
| 2007/0117804 A1 | 5/2007 | Zhao et al. |
| 2007/0149535 A1 | 6/2007 | Berset et al. |
| 2007/0185063 A1 | 8/2007 | Storer et al. |
| 2007/0197507 A1 | 8/2007 | Morgan et al. |
| 2007/0219205 A1 | 9/2007 | Brenchley et al. |
| 2008/0021217 A1 | 1/2008 | Borchardt et al. |
| 2008/0045536 A1 | 2/2008 | Vaccaro et al. |
| 2008/0070894 A1 | 3/2008 | Kawamura et al. |
| 2008/0102028 A1 | 5/2008 | Morel |
| 2008/0103136 A1 | 5/2008 | Sato et al. |
| 2008/0113978 A1 | 5/2008 | Barbosa et al. |
| 2008/0161341 A1 | 7/2008 | Calderwood et al. |
| 2008/0167314 A1 | 7/2008 | Uchikawa et al. |
| 2008/0207634 A1 | 8/2008 | Gudmundsson |
| 2008/0221092 A1 | 9/2008 | Bluhm et al. |
| 2008/0242862 A1 | 10/2008 | Calderwood et al. |
| 2008/0255358 A1 | 10/2008 | Bamford et al. |
| 2008/0300242 A1 | 12/2008 | Kuntz et al. |
| 2008/0305081 A1 | 12/2008 | Hashihayata et al. |
| 2008/0318975 A1 | 12/2008 | Wagner et al. |
| 2009/0005374 A1 | 1/2009 | Melvin, Jr. et al. |
| 2009/0023737 A1 | 1/2009 | Xu et al. |
| 2009/0054409 A1 | 2/2009 | Andrews et al. |
| 2009/0124625 A1 | 5/2009 | Bessis et al. |
| 2009/0143376 A1 | 6/2009 | Milburn et al. |
| 2009/0153035 A1 | 6/2009 | Shin et al. |
| 2009/0156604 A1 | 6/2009 | Holder et al. |
| 2009/0175852 A1 | 7/2009 | Ciavarri et al. |
| 2009/0176778 A1 | 7/2009 | Schmitz et al. |
| 2009/0203732 A1 | 8/2009 | Dhanak et al. |
| 2009/0209573 A1 | 8/2009 | Wu et al. |
| 2009/0215818 A1 | 8/2009 | Adams et al. |
| 2009/0270436 A1 | 10/2009 | Iino et al. |
| 2009/0317361 A1 | 12/2009 | Cho et al. |
| 2009/0325953 A1 | 12/2009 | Sahoo et al. |
| 2010/0029633 A1 | 2/2010 | Allen et al. |
| 2010/0029638 A1 | 2/2010 | Melvin, Jr. et al. |
| 2010/0063068 A1 | 3/2010 | Pracitto et al. |
| 2010/0160280 A1 | 6/2010 | Allen et al. |
| 2012/0302564 A1 | 11/2012 | Lankau et al. |

FOREIGN PATENT DOCUMENTS

| | | |
|---|---|---|
| CL | 3212-2007 | 6/2008 |
| CN | 1066849 | 12/1992 |
| CN | 1122601 | 5/1996 |
| EP | 0728759 | 8/1996 |
| EP | 1 293 213 A1 | 3/2003 |
| IT | 1374954 B1 | 5/2010 |
| JP | 6247969 A | 9/1994 |
| JP | 2001-006877 | 1/2001 |
| JP | 2001-057292 A | 2/2001 |
| JP | 2003-313126 A | 11/2003 |
| JP | 2004-002826 A | 1/2004 |
| JP | 2005-343889 A | 12/2005 |
| WO | WO 90/15534 A1 | 12/1990 |
| WO | WO 91/19497 A1 | 12/1991 |
| WO | WO 92/10190 A1 | 6/1992 |
| WO | WO 92/10498 A1 | 6/1992 |
| WO | WO 96/34866 A1 | 11/1996 |
| WO | WO 02/34748 A1 | 5/2002 |
| WO | WO 02/066478 A1 | 8/2002 |
| WO | WO 2004/017950 A2 | 3/2004 |
| WO | WO 2004/026877 A1 | 4/2004 |
| WO | WO 2004/035579 A1 | 4/2004 |
| WO | WO 2004/075846 | 9/2004 |
| WO | WO 2004/087710 | 10/2004 |
| WO | WO 2004/089416 A2 | 10/2004 |
| WO | WO 2004/103991 A1 | 12/2004 |
| WO | WO 2005/014599 A1 | 2/2005 |
| WO | WO 2005/020885 A1 | 3/2005 |
| WO | WO 2005/020885 A2 | 3/2005 |
| WO | WO 2005/047290 A2 | 5/2005 |
| WO | WO 2006/044509 A2 | 4/2006 |
| WO | WO 2006/102194 | 9/2006 |
| WO | WO 2007/003386 A1 | 1/2007 |
| WO | WO 2007/013673 A1 | 2/2007 |
| WO | WO 2007/048779 | 5/2007 |
| WO | WO 2007/087548 A2 | 8/2007 |
| WO | WO 2007/145921 A1 | 12/2007 |
| WO | WO 2008/003511 A1 | 1/2008 |
| WO | WO 2008/030579 A2 | 3/2008 |
| WO | WO 2008/030795 A2 | 3/2008 |
| WO | WO 2008/057402 A2 | 5/2008 |
| WO | WO 2008/079460 A2 | 7/2008 |
| WO | WO 2008/081910 A1 | 7/2008 |
| WO | WO 2008/121687 A2 | 10/2008 |
| WO | WO 2008/124153 A1 | 10/2008 |
| WO | WO 2008/133192 A1 | 11/2008 |
| WO | WO 2008/134553 A1 | 11/2008 |
| WO | WO 2008/138834 A1 | 11/2008 |

(56) References Cited

FOREIGN PATENT DOCUMENTS

| | | |
|---|---|---|
| WO | WO 2008/141079 A1 | 11/2008 |
| WO | WO 2008/156614 A2 | 12/2008 |
| WO | WO 2009/005675 A1 | 1/2009 |
| WO | WO 2009/016286 A2 | 2/2009 |
| WO | WO 2009/016560 A2 | 2/2009 |
| WO | WO 2009/017701 A2 | 2/2009 |
| WO | WO 2009/021990 A1 | 2/2009 |
| WO | WO 2009/023253 A2 | 2/2009 |
| WO | WO 2009/024585 A2 | 2/2009 |
| WO | WO 2009/077334 | 2/2009 |
| WO | WO 2009/037394 A2 | 3/2009 |
| WO | WO 2009/060197 A1 | 5/2009 |
| WO | WO 2009/061856 A1 | 5/2009 |
| WO | WO 2009/081857 A1 | 7/2009 |
| WO | WO 2009/086123 A1 | 7/2009 |
| WO | WO 2009/086130 A1 | 7/2009 |
| WO | WO 2009/097233 A1 | 8/2009 |
| WO | WO 2009/108546 A1 | 9/2009 |
| WO | WO 2009/112679 A1 | 9/2009 |
| WO | WO 2009/117157 A1 | 9/2009 |
| WO | WO 2009/124653 A2 | 10/2009 |
| WO | WO 2009/126691 A1 | 10/2009 |
| WO | WO 2009/143156 A2 | 11/2009 |
| WO | WO 2009/146358 | 12/2009 |
| WO | WO 2009/152072 A1 | 12/2009 |
| WO | WO 2010/002985 A1 | 1/2010 |
| WO | WO 2010/009155 A2 | 1/2010 |
| WO | WO 2010/011837 A1 | 1/2010 |
| WO | WO 2010/016005 A1 | 2/2010 |
| WO | WO 2010/018327 A1 | 2/2010 |
| WO | WO 2010/033906 A2 | 3/2010 |
| WO | WO 2010/036407 A2 | 4/2010 |
| WO | WO 2010/047279 A1 | 4/2010 |
| WO | WO 2010/048149 A2 | 4/2010 |
| WO | WO 2010/054253 | 5/2010 |
| WO | WO 2010/059836 A1 | 5/2010 |
| WO | WO 2010/059838 A2 | 5/2010 |
| WO | WO 2010/069684 A1 | 6/2010 |
| WO | WO 2010/084425 A1 | 7/2010 |
| WO | WO 2010/084690 A1 | 7/2010 |
| WO | WO 2010/088368 A2 | 8/2010 |
| WO | WO 2010/088518 A2 | 8/2010 |
| WO | WO 2010/097367 A1 | 9/2010 |
| WO | WO 2010/098458 A1 | 9/2010 |
| WO | WO 2010/101230 | 9/2010 |
| WO | WO 2010/101230 A1 | 9/2010 |
| WO | WO 2010/108074 A2 | 9/2010 |
| WO | WO 2010/110277 A1 | 9/2010 |
| WO | WO 2010/119264 A1 | 10/2010 |
| WO | WO 2010/138833 | 12/2010 |
| WO | WO 2010/138833 A1 | 12/2010 |
| WO | WO 2011/013729 A1 | 2/2011 |
| WO | WO 2011/021520 A1 | 2/2011 |
| WO | WO 2011/051324 | 5/2011 |
| WO | WO 2011/051342 | 5/2011 |
| WO | WO 2011/051342 A1 | 5/2011 |
| WO | WO 2011/059099 A1 | 5/2011 |
| WO | WO 2011/089400 A1 | 7/2011 |
| WO | WO 2011/110545 | 9/2011 |
| WO | WO 2011/110545 A1 | 9/2011 |
| WO | WO 2012/104293 | 8/2012 |
| WO | WO 2013/000924 | 1/2013 |
| WO | WO 2013/034755 | 3/2013 |
| WO | WO 2013/034761 | 3/2013 |
| WO | WO 2014/009305 | 1/2014 |

OTHER PUBLICATIONS

Reierson, Current Neuropharmacology, 9, 715-727, 2011.
Reneerkens O et al_Behavioural Brain Research, 236, 16-22, 2013.
West, Frontiers in Systems Neuroscience, 5, 55-64, 2011.
Belanger, et al. "Discovery of imidazo[1,2-a]pyrazine-based Aurora kinase inhibitors", Bioorganic & Medicinal Chemistry Letters (2010), 20(17), 5170-5174.
Belanger, et al. "Discovery of orally bioavailable imidazo[1,2-a]pyrazine-based Aurora kinase inhibitors", Bioorganic & Medicinal Chemistry Letters (2010), 20(22), 6739-6743.
Bouloc, et al. "Structure-based design of imidazo[1,2-a]pyrazine derivatives as selective inhibitors of Aurora-A kinase in cells", Bioorganic & Medicinal Chemistry Letters (2010), 20(20), 5988-5993.
Blokland et al., Expert Opin. Ther. Patents (2012) 22(4), pp. 349-354.
Carverley, M.J. Tetrahedron, 1987, 43(20), 4609-19.
Charych et al., The Journal of Neuroscience, Jul. 7, 2010 • 30(27):9027-9037.
Ennanceur, Behav Brain Res 1988, 31, 47-59.
Gaudry et al., Organic Syntheses, 1976, 55, 24-27.
Gehlert, et al. "3-(4-Chloro-2-morpholin-4-yl-thiazol-5-yl)-8-(1-ethylpropyl)-2,6- dimethyl- imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.
Gennaro et al. Remington's Pharmaceutical Sciences (18th ed., Mack Publishing Company, 1990, see especially Part 8: Pharmaceutical preparations and their Manufacture), pp. 1435-1712 (split/uploaded into 4 separate files due to size).
Gudmundsson, et al. "Imidazo[1,2-a]pyridines with potent activity against herpesviruses", Bioorganic & Medicinal Chemistry Letters (2007), 17(10), 2735-2739.
Gudmundsson, et al. "Synthesis of Novel Imidazo[1,2-a]pyridines with Potent Activity against Herpesviruses", Organic Letters (2003), 5(8), 1369-1372 CODEN: ORLEF7; ISSN: 1523-7060.
Hebb et al., Current Opinion in Pharmacology 2007, 7:86-92.
Il'icheva, et al. "Theoretical Study of the Structure of Adenosine Deaminase Complexes with Adenosine Analogues: I. Aza-, Deaza-, and Isomeric Azadeazaanalogues of Adenosine", Russian Journal of Bioorganic Chemistry (2005), 31(5), 439-452.
Kehler et al., Expert Opin. Ther. Patents (2007) 17(2), pp. 147-158.
Kehler et al. Expert Opin. Ther. Patents (2009) 19(12), pp. 1715-1725.
Kerekes, et al. "Aurora Kinase Inhibitors Based on the Imidazo[1,2-a]pyrazine Core: Fluorine and Deuterium Incorporation Improve Oral Absorption and Exposure" Journal of Medicinal Chemistry (2011), 54(1), 201-210.
Kobe, et al. "Use of distance geometry approach for the in vitro antiviral activity evaluation of N-bridgehead C-nucleosides", European Journal of Medicinal Chemistry (1992), 27(3), 259-66.
Kolar, et al. "Transformations of the pyrido[1,2-a]pyrazine ring system into imidazo[1,2-a]pyridines, imidazo[1,2-a]pyrimidines and 2-oxa-6a, 10c-diazaaceanthrylenes", Journal of Heterocyclic Chemistry (1996), 33(3), 639-642.
Lhassani, et al. "Synthesis and antiviral activity of imidazo[1,2-a]pyridines", European Journal of Medicinal Chemistry (1999), 34(3), 271-274.
MacCoss, et al. "Synthesis and biological evaluation of nucleosides containing 8- aminoimidazol[1,2-a]pyrazine as an isosteric replacement for adenine", Journal of Heterocyclic Chemistry (1993), 30(5), 1213-20.
Meng, et al. "Bioisosteric approach to the discovery of imidazo[1,2-a]pyrazines as potent Aurora kinase inhibitors" Bioorganic & Medicinal Chemistry Letters (2011), 21(1), 592-598.
Owen et al., Bioorganic & Medicinal Chemistry Letters, vol. 17, No. 2, pp. 486-490 (2007).
Pan, et al. "Synthesis of novel isoxazolinyl substituted imidazo[1,2-a]pyridine C-nucleoside analogs", Tetrahedron Letters (1998), 39(45), 8191-8194.
Schmidt et al., The Journal of Pharmacology and Experimental Therapeutics, vol. 325, No. 2, pp. 681-690.
Siuciak, Judith A., CNS Drugs 2008; 22(12): 983-993.
van den Heuvel, M. et al.; J. Org. Chem., 2004, 250.
Wang, et al. "Synthesis of novel isoxazolinyl substituted imidazo]1,2-a]pyridine C-nucleoside analogs", Hecheng Huaxue (2001), 9(5), 386-389.
Wang, X. et al. Tetrahedron Lett., 2000, 4335-4338.
Yu, Tao et al. "Discovery of a Potent, Injectable Inhibitor of Aurora Kinases Based on the Imidazo-[1,2-a]-Pyrazine Core", ACS Medicinal Chemistry Letters (2010), 1(5), 214-218.

(56) References Cited

OTHER PUBLICATIONS

Zarubin, et al. "Theoretical study of adenosine and its isosteric analogs. A possible mechanism of their binding in an active site of mammalian adenosine deaminase", Vestnik Samarskogo Gosudarstvennogo Universiteta, Estestvennonauchnaya Seriya (2003), (Spec.), 152-173.
Aggarwal, Synthetic Communications, pp. 1873-1878, 2006.
Aggarwal et al., Journal of Fluorine Chemistry (2009), 130 (10), 886-893.
Aggarwal R et al_European Journal of Medicinal Chemistry, Editions Scientific Elsevier, Paris, FR, 46(12), 6083-6088, (2011).
Andres J et al., Bioorganic & Medicinal Chemistry Letters, 785-790, 2013.
Baratti et al., Behav. Pharmacol. 1999; 10:731-737.
Bertelsen, et al., Arch Gen Psychiatry, 65:762 (2008).
Boess, Neuropharmacology, 47, 1081-1092, 2004.
Domek-Łopacińska Ku, Strosznajder JB Mol Neurobiol. 2010; 41(2-3):129-37).
Harig et al., J. Translational Med. 2:44 (2004).
Kehler, et al., Expert Opin. Ther. Pat., "Phosphodiesterase 10A inhibitors: a 2009-20012 patent update", pp. 1-15 (Dec. 5, 2012).
Kingsbury et al. J. Med. Chem. 1991, 98-107.
Kumar, Green Chemistry, pp. 156-157, 2004.
Kumar P, et al. Behav Pharmacol. May 2010; 21(3):217-30).
Lasne et al. Top. curr. Chem. 2002, 202-258.
Masood, J Pharmacol Exp Ther, 326(2), 369-379, 2008.
Mennitti, F. S. et al. Nature Rev. Drug Discovery 2006, 5, 660-669.
Miller et al. Angew. Chem. Int. Ed. 2008, 47, 8998-9033.
Netscher et al. Eur. J. Org. chem. 2007, 1176-1183.
Pandit, Proc. Natl. Acad. Sci. USA, 106(43), 18225-30, 2009.
Prickaerts, Neuroscience, 2002:113: :351-361.
Reierson, G.W. et al. Current Neuropharmacology 2011; 9:715-727).
Reneerkens O et al Behavioral Brain Research, 236, 16-22, 2013.
Siuciak, et al., Expert Opin. Drug Discov. 2:1001 (2007).
Vyas et al, Ind. J. Het. Chem. 2005, 361-362.
International Search Report for PCT/EP2012/062381 dated Sep. 19, 2012.
International Search Report for PCT/EP2013/063244 dated Aug. 16, 2013.
International Search Report for PCT/EP2013/064355 dated Oct. 10, 2013.
Gehlert, et al. "3-(4-Chloro-2-morpholin-4-yl-thiazol-5-yl)-8-(1-ethylpropyl)-2,6-dimethyl-imidazo[1,2-b]pyridazine: a novel brain-penetrant, orally available corticotropin-releasing factor receptor 1 antagonist with efficacy in animal models of alcoholism", Journal of Neuroscience (2007), 27(10), 2718-2726.
MacCoss, et al. "Synthesis and biological evaluation of nucleosides containing 8-aminoimidazo[1,2-a]pyrazine as an isosteric replacement for adenine", Journal of Heterocyclic Chemistry (1993), 30(5), 1213-20.
International Search Report for PCT/EP2010/066264 dated Aug. 12, 2010.
International Search Report for PCT/EP2011/053445 dated Aug. 18, 2011.

\* cited by examiner

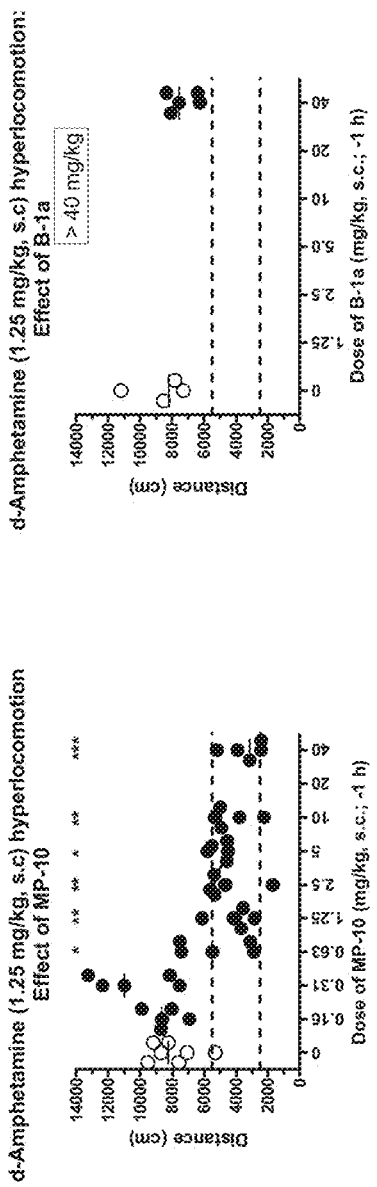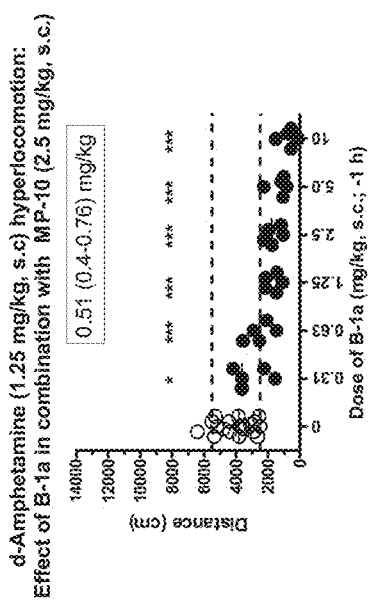
FIG 6a
FIG 6b
FIG 6c

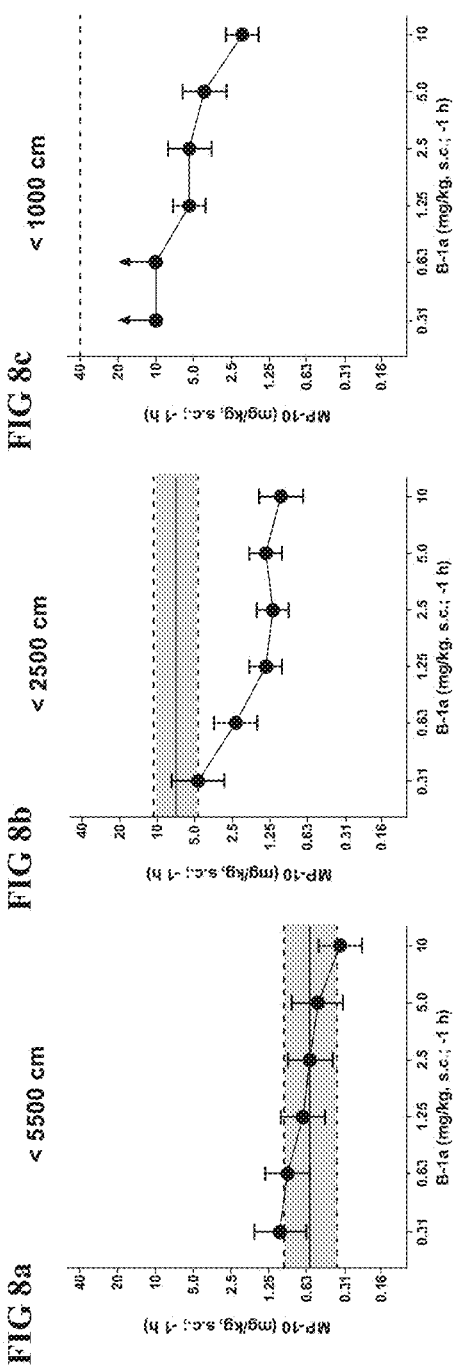

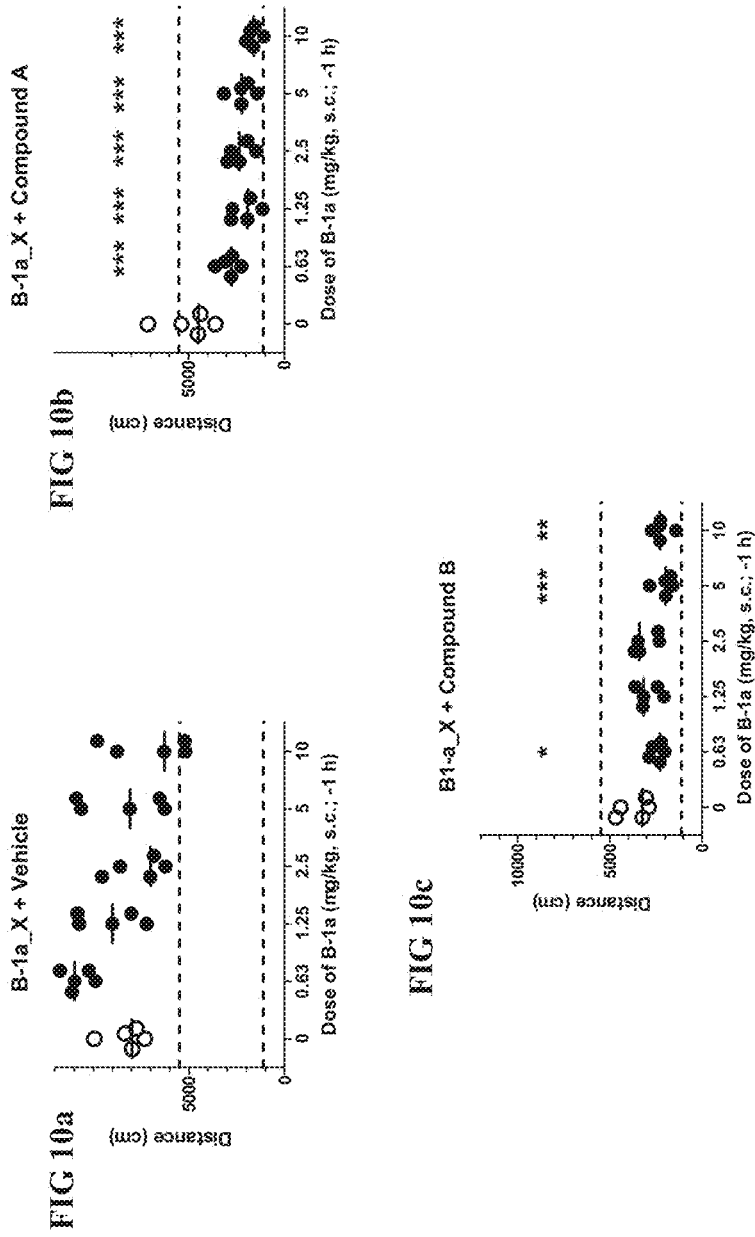

COMBINATIONS COMPRISING PDE 2 INHIBITORS SUCH AS 1-ARYL-4-METHYL-[1,2,4]TRIAZOLO-[4,3-A]]QUINOXALINE COMPOUNDS AND PDE 10 INHIBITORS FOR USE IN THE TREATMENT OF NEUROLOGICAL OF METABOLIC DISORDERS

CROSS REFERENCE TO RELATED APPLICATIONS

This application is the national stage of PCT Application No. PCT/EP2013/063244, filed Jun. 25, 2013, which claims priority from European Patent Application No. 12173681.3, filed Jun. 26, 2012, the entire disclosures of which are hereby incorporated in their entirety.

FIELD OF THE INVENTION

The present invention relates to combinations of phosphodiesterase 2 (PDE2) inhibitors with inhibitors of phosphodiesterase 10 (PDE10). In particular, the invention relates to combinations of 1-aryl-4-methyl-[1,2,4]triazolo[4, 3-a]-quinoxaline derivatives which have been found to inhibit phosphodiesterase 2 (PDE2), with inhibitors of phosphodiesterase 10 (PDE10). Particular PDE10 inhibitors are selected from the group of MP-10, PQ-10, TP-10, papaverine, and the compounds disclosed in WO 2011/051324 and in WO 2011/110545. The invention is also directed to pharmaceutical compositions comprising such combinations, to processes for preparing such compositions, to the use of PDE2 inhibitors, in particular of 1-aryl-4-methyl-[1, 2,4]triazolo[4,3-a]-quinoxaline derivatives, for the potentiation of said PDE10 inhibitors, and to the use of said PDE10 inhibitors for the potentiation of the effect of said PDE2 inhibitors, in particular of 1-aryl-4-methyl-[1,2,4]triazolo[4, 3-a]-quinoxaline derivatives, and to the use of such combinations and compositions for the prevention and treatment of disorders in which PDE2 and PDE10 are involved, such as neurological and psychiatric disorders, and endocrinological or metabolic diseases.

BACKGROUND OF THE INVENTION

Journal of Fluorine Chemistry (2009), 130 (10), 886-893 discloses 1-aryl-4-methyl-[1,2,4]triazolo[3,4-a]quinoxalines wherein aryl is phenyl, 4-methoxyphenyl, 4-chlorophenyl or 4-nitrophenyl, unexpectedly arising in a reaction of 2-hydrazine-3-methylquinoxaline with trifluoromethyl-beta-diketones.

Green Chemistry (2004), 6, 156-157 discloses solvent-free methods for the synthesis of 1-aryl-4-methyl-[1,2,4]triazolo[3,4-a]quinoxalines wherein aryl is phenyl, 4-methylphenyl, 4-chlorophenyl, 4-methoxyphenyl and 3-methoxyphenyl.

Synthetic Communications (2006), 36, 1873-1878 discloses methods for the synthesis of 1-aryl-4-methyl-[1,2,4]triazolo[3,4-a]quinoxalines wherein aryl is phenyl, 4-methylphenyl, 4-chlorophenyl, 2-methoxyphenyl and 4-methoxyphenyl.

WO-2010/101230 discloses [1,2,4]triazolo[4,3-a]quinoxalin-4(5H)-ones as PDE9 inhibitors useful for treating urination disorders. WO 2012/104293, WO 2010/054253 and Expert Opinion on Therapeutic Patents, Informa Healthcare, GB, (2009), 19 (12), 1715-1725 disclose compounds as phosphodiesterase inhibitors.

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

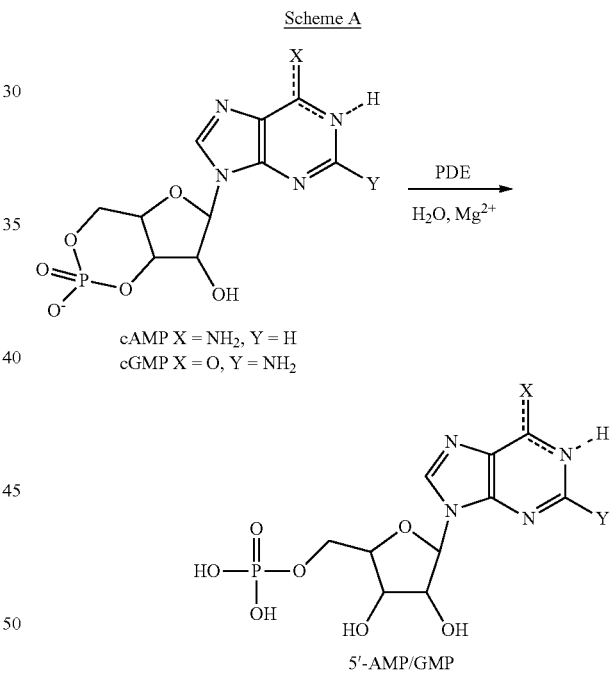

Scheme A

On the basis of substrate specificity, the PDE families can be divided into three groups: i) the cAMP-specific PDEs, which include PDE4, 7 and 8; ii) the cGMP-selective enzymes PDE5, 6 and 9; and iii) the dual-substrate PDEs, PDE1, 2 and 3, as well as PDE10 and 11.

Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

Phosphodiesterase 2A (PDE2A) inactivates intracellular signalling mechanisms reliant on cyclic nucleotide signalling mediated by cAMP and cGMP via their degradation.

Such signalling pathways are known to play a role in the regulation of genes involved in the induction of synaptic plasticity.

The pharmacological inhibition of PDE2 therefore causes increased levels of synaptic plasticity (an underlying correlate of learning and memory), suggesting that PDE2A modulation may be a target for alleviating cognitive deficits seen in people suffering from disorders such as for example, schizophrenia, Alzheimer's disease, Parkinson's disease and other CNS disorders associated with cognitive dysfunction (Neuropharmacology 47, (2004), 1081-92).

Phosphodiesterase 2A (PDE2A) is more abundantly expressed in the brain relative to peripheral tissues. The high expression of PDE2 in the limbic system (isocortex, hippocampus, amygdala, habenula, basal ganglia) suggests that PDE2 may modulate neuronal signalling involved in emotion, perception, concentration, learning and memory. Additionally, PDE2 is expressed in the nucleus accumbens, the olfactory bulb, the olfactory tubercle and the amygdala, supporting the suggestion that PDE2 may also be involved in anxiety and depression.

Additionally, PDE2 inhibitors have been shown to be beneficial in the reduction of oxidative stress-induced anxiety, supporting their use in the treatment of anxiety in neuropsychiatric and neurodegenerative disorders that involve oxidative stress, such as Alzheimer's disease, Parkinson's disease and multiple sclerosis (J. Pharmacol. Exp. Ther. 2008, 326(2), 369-379).

PDE2 inhibitors have been shown to enhance long term potentiation of synaptic transmission and to improve memory acquisition and consolidation in the object recognition and in the social recognition tests in rats. Furthermore, PDE2 inhibitors have been shown to reverse the MK-801 induced working memory deficit in the T-maze in mice. PDE2 inhibitors have also been shown to display activity in forced swim test and light/dark box models; and to show anxiolytic-like effects in elevated plus-maze, hole-board and open-field tests and to prevent stress-induced changes in apoptosis and behaviour (Neuropharmacology 47, (2004), 1081-92).

Thus, PDE2 inhibitors may be useful in the treatment of memory deficiency, cognitive disorders, anxiety, bipolar disorder and depression.

Of all the 11 known PDE families, PDE10 has the most restricted distribution with high expression only in the brain and testes. In the brain, PDE10A mRNA and protein are highly expressed in a majority of striatal Medium Spiny Neurons (MSNs). This unique distribution of PDE10A in the brain, together with its increased pharmacological characterization, indicates a potential use of PDE10A inhibitors for treating neurological and psychiatric disorders like schizophrenia.

Thus, PDE10 inhibitors may possess a pharmacological profile similar to that of the current antipsychotics which mainly treat positive symptoms of schizophrenia, but also having the potential to improve the negative and cognitive symptoms of schizophrenia, while lacking the non-target related side effects such as EPS or prolactin release, that are often observed with the currently available antipsychotics.

Since PDE10 inhibitors can be used to raise levels of cAMP and/or cGMP within cells that express the PDE10 enzyme, for example neurons that comprise the basal ganglia, PDE10 inhibitors may be useful in treating schizophrenia and additionally, a variety of conditions as described herein, for example, Parkinson's Disease, Huntington's Disease, addiction and depression. PDE10 inhibitors may be also useful in other conditions such as obesity, non-insulin dependent diabetes, bipolar disorder, obsessive compulsive disorder and pain.

SUMMARY OF THE INVENTION

It has now been surprisingly found that the effect of PDE10 inhibitors can be potentiated with PDE2 inhibitors. In particular the PDE10 inhibitors can be selected from the group of MP-10, PQ-10, TP-10, papaverine, and the compounds disclosed in WO 2011/051324 and in WO 2011/110545, documents which are hereby incorporated by reference in their entirety. The effect of PDE10 inhibitors can be potentiated in particular with 1-aryl-4-methyl-[1,2,4]triazolo[4,3-a]-quinoxaline derivatives of formula (I) according to the invention, which are inhibitors of PDE2. For example, it has been observed that the PDE2 inhibitors of the invention in combination with PDE10 inhibitors, in particular with the PDE10 inhibitor MP-10 or with the PDE10 inhibitors compound A (compound number 1 in WO 2011/051324) and compound B (compound number 25 in WO 2011/110545) below could inhibit the effects of apomorphine or amphetamine in rats Compound A

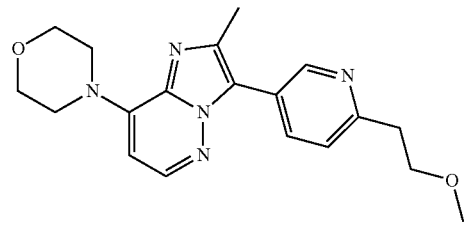

(Compound number 1 in WO 2011/051324)

Compound B

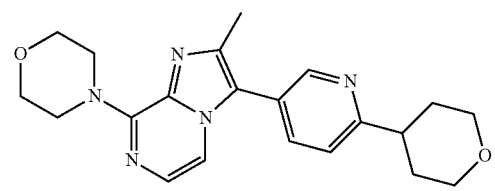

(Compound number 25 in WO 2011/110545).

It has also been observed that PDE10 inhibitor MP-10 could dose-dependently potentiate the in vivo binding of a radioligand binding selectively to the catalytic domain of the PDE2 enzyme.

Thus, it is an object of the present invention to provide novel combinations comprising a) a PDE2 inhibitor, or a pharmaceutically acceptable salt or a solvate thereof; and b) one or more PDE10 inhibitor(s), or a pharmaceutically acceptable salt or a solvate thereof.

The present invention also relates to products containing as first active ingredient a) a PDE2 inhibitor or a pharmaceutically acceptable salt or a solvate thereof, as defined herein, and as a second active ingredient b) one or more PDE10 inhibitors or a pharmaceutically acceptable salt of a solvate thereof, as combined preparations for simultaneous, separate or sequential use in the treatment of patients suffering from neurological or psychiatric disorders, or endocrinological or metabolic diseases.

Illustrative of the invention is a pharmaceutical composition comprising a pharmaceutically acceptable carrier and any of the combinations described above. An illustration of the invention is a pharmaceutical composition made by mixing any of the combinations described above and a pharmaceutically acceptable carrier. Illustrating the invention is a process for making a pharmaceutical composition comprising mixing any of the combinations described above and a pharmaceutically acceptable carrier.

In a further aspect, the invention relates to the use of a PDE2 inhibitor or a pharmaceutically acceptable salt or a solvate thereof for the potentiation of the effect of one or more PDE10 inhibitor(s) or a pharmaceutically acceptable salt or a solvate thereof.

The invention also relates to a PDE2 inhibitor or a pharmaceutically acceptable salt or a solvate thereof, as defined herein, for use in the enhancement of the therapeutic effect of one or more PDE10 inhibitor(s) or a pharmaceutically acceptable salt or a solvate thereof, in patients suffering from neurological or psychiatric disorders, or endocrinological or metabolic diseases.

Further, the present invention also concerns the use of a PDE2 inhibitor or a pharmaceutically acceptable salt or a solvate thereof, as defined herein, for the preparation of a medicament for enhancing the therapeutic effect of one or more PDE10 inhibitor(s) or a pharmaceutically acceptable salt or a solvate thereof in patients suffering from neurological or psychiatric disorders, or endocrinological or metabolic diseases.

The invention further relates to the use of one or more PDE10 inhibitor(s) or a pharmaceutically acceptable salt or a solvate thereof, for the potentiation of the effect of a PDE2 inhibitor or a pharmaceutically acceptable salt or a solvate thereof. The invention also relates to one or more PDE10 inhibitor(s), for use in the enhancement of the therapeutic effect of a compound of Formula (I) or a pharmaceutically acceptable salt or a solvate thereof, as defined herein. In a further aspect, the present invention also concerns the use of one or more PDE10 inhibitor(s) or a pharmaceutically acceptable salt or a solvate thereof, for the preparation of a medicament for enhancing the therapeutic effect of a PDE2 inhibitor or a pharmaceutically acceptable salt or a solvate thereof, as defined herein, in patients suffering from neurological or psychiatric disorders, or endocrinological or metabolic diseases.

The invention further relates to a method of treating a neurological or psychiatric disorder, or an endocrinological or a metabolic disease comprising administering to a subject in need thereof a therapeutically effective amount of a combination comprising a) a PDE2 inhibitor or a pharmaceutically acceptable salt or a solvate thereof and b) one or more PDE10 inhibitor(s) or a pharmaceutically acceptable salt or a solvate thereof or a therapeutically effective amount of a pharmaceutical composition as described above.

The invention further relates to a method of enhancing the therapeutic effect of a PDE2 inhibitor or a pharmaceutically acceptable salt or a solvate thereof, as defined herein, comprising administering to a subject in need thereof a therapeutically effective amount of a combination comprising a) a PDE2 inhibitor or a pharmaceutically acceptable salt or a solvate thereof as defined herein and b) one or more PDE10 inhibitor(s) or a pharmaceutically acceptable salt or a solvate thereof a therapeutically effective amount of a pharmaceutical composition as described above.

The invention further relates to a method of enhancing the therapeutic effect of one or more PDE10 inhibitor(s) or a pharmaceutically acceptable salt or a solvate thereof, comprising administering to a subject in need thereof a therapeutically effective amount of a combination comprising a) a PDE2 inhibitor or a pharmaceutically acceptable salt or a solvate thereof and b) one or more PDE10 inhibitor(s) or a pharmaceutically acceptable salt or a solvate thereof or a therapeutically effective amount of a pharmaceutical composition as described above.

DESCRIPTION OF THE FIGURES

In FIG. 2, the following symbols correspond with the indicated doses below ⊖ 0 mg/kg B1-a, s.c., −1 h; ✦ 0.31 mg/kg B1-a, s.c., −1 h; ▽ 0.63 mg/kg B1-a, s.c., −1 h; ✱ 1.25 mg/kg B1-a, s.c., −1 h; ● 2.5 mg/kg B1-a, s.c., −1 h; ▼ 5.0 mg/kg B1-a, s.c., −1 h; ▲ 10 mg/kg B1-a, s.c., −1 h.

FIG. 4 shows the effect of B-1a (0 vs. 10 mg/kg s.c.; −1 h) on the dose-response of Compound A (−1 h, s.c.; In FIG. 4: * $p<0.05$,  $p<0.01$, * $p<0.001$ (Bonferroni posttests 0 vs 10 mg/kg). $ED_{50}$s (and 95% confidence limits) of the PDE10 inhibitors (PDE10-is) for reducing agitation scores to <21, <10 and <5 have been listed for co-treatment with the PDE2-i at 0 and 10 mg/kg.

(FIG. 4a) $ED_{50}$s (95% Confidence Limits):
<21:
  0 mg/kg: 2.71 (2.00-3.7) mg/kg
  10 mg/kg: 3.1 (2.30-4.2) mg/kg
<10:
  0 mg/kg: 16.3 (10.1-26.3) mg/kg
  10 mg/kg: 6.2 (4.6-8.4) mg/kg
<5:
  0 mg/kg: ≥40 mg/kg
  10 mg/kg: 12.4 (9.1-16.7) mg/kg (FIG. 4b) $ED_{50}s$ (95% Confidence Limits):
<21:
  0 mg/kg: 2.71 (1.68-4.4) mg/kg
  10 mg/kg: 2.36 (1.74-3.2) mg/kg
<10:
  0 mg/kg: 32 (2736-50) mg/kg
  10 mg/kg: 6.2 (4.6-8.4) mg/kg
<5:
  0 mg/kg: ≥40 mg/kg
  10 mg/kg: 10.8 (7.2-16.1) mg/kg
FIGS. 5a and 5c, respectively) or Compound B (0 or 2.5 mg/kg, s.c., −1 h;
FIGS. 5b and 5d, respectively). The dotted horizontal line represents the criterion for mild inhibition of agitation (score <21).
In FIG. 5: * p<0.05 (Dunnett's Multiple Comparison Test vs. 0 mg/kg)

FIG. 6a shows the dose-dependent inhibition of d-amphetamine-induced hyperlocomotion measured 1 h after s.c. injection of MP-10; FIG. 6b shows the absence of effect against d-amphetamine-induced hyperlocomotion measured 1 h after s.c. injection of B-1a (40 mg/kg); FIG. 6c shows the dose-dependent potentiation of the effect of MP-10 (2.5 mg/kg, s.c.) on d-amphetamine-induced hyperlocomotion measured 1 h after s.c. injection of B-1a.

In FIG. 7, the following symbols correspond with the indicated doses below ⊖ 0 mg/kg B1-a, s.c., −1 h; ∀ 0.31 mg/kg B1-a, s.c., −1 h; ⊼ 0.63 mg/kg B1-a, s.c., −1 h; ● 1.25 mg/kg B1-a, s.c., −1 h; ▼ 2.5 mg/kg B1-a, s.c., −1 h; ▲ 5.0 mg/kg B1-a, s.c., −1 h; ✱ 10 mg/kg B1-a, s.c., −1 h.

FIGS. 8a-c show the $ED_{50}$ (and 95% confidence limits) of MP-10 (−1 h, s.c.) for reducing d-amphetamine-induced hyperlocomotion to a distance <5500 cm (FIG. 8a), <2500 cm, (FIG. 8b) and <1000 cm (FIG. 8c) as a function of dose of co-administered PDE2-i B-1a (0.63 to 10 mg/kg, s.c.; −1 h; closed symbols) or solvent (10 ml/kg, s.c.; −1 h; open symbols). The gray horizontal bar represents the $ED_{50}$ (and 95% confidence limits) of MP-10 (−1 h, s.c.) combined with the solvent of B-1a (FIGS. 8a and 8b) or of MP-10 (−1 h, s.c.) alone (FIG. 8c; >40 mg/kg, historical data).

FIG. 9 shows the effect of a standard dose B-1a (0 vs. 10 mg/kg s.c.; −1 h) on the dose-response of Compound A (−1 h, s.c.; In FIG. 9: * p<0.05,  p<0.01, * p<0.001 (Bonferroni posttests 0 vs 10 mg/kg). $ED_{50}s$ (and 95% confidence limits) of the PDE10-is for reducing distance traveled to <5500 cm and to <1100 cm have been listed for co-treatment with B-1a at 0 and 10 mg/kg.

(FIG. 9a) $ED_{50}s$ (95% Confidence Limits):
<5500 cm:
  0 mg/kg: 0.89 (0.55-1.43) mg/kg
  10 mg/kg: 0.67 (0.45-1.01) mg/kg
<1100 cm:
  0 mg/kg: >40 mg/kg
  10 mg/kg: 6.2 (3.6-10.6) mg/kg
(FIG. 9b) $ED_{50}s$ (95% Confidence Limits):
<5500 cm:
  0 mg/kg: 3.1 (1.70-5.6) mg/kg
  10 mg/kg: 2.04 (1.51-2.76) mg/kg
<1100 cm:
  0 mg/kg: >40 mg/kg
  10 mg/kg: 16.3 (12.0-22.1) mg/kg FIG. 10 shows the effect of B-1a (0, 0.63, 1.25, 2.5 and 5.0 mg/kg s.c.; −1 h; FIG. 10a) on d-amphetamine-induced hyperlocomotion in the presence of standard doses of Compound A (0 or 2.5 mg/kg, s.c., −1 h; FIG. 10b) or Compound B (0 or 2.5 mg/kg, s.c., −1 h; FIG. 10c) (open and closed circles for PDE10-i at 0 and 10 mg/kg, respectively). The dotted horizontal lines represent the critical levels for drug-induced effects (<5500 cm and <1100 cm). B-1a was ineffective against the d-amphetamine-induced hyperlocomotion when combined with the solvent of the PDE10-is but potentiated the effect of both PDE10-is (2.5 mg/kg vs. 0 mg/kg).

DETAILED DESCRIPTION OF THE INVENTION

Figure 1A:
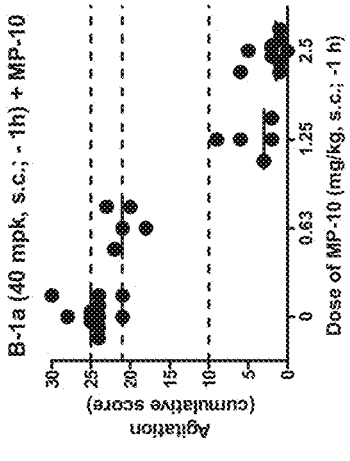
FIGS. 1a-c show the effect of (a) solvent+various doses of MP-10 (0, 0.63, 1.25 and 2.5 mg/kg) administered subcutaneously (s.c.); (b) compound B-1a (40 mg/kg, s.c.) administered subcutaneously+various doses of MP-10 (0, 0.63, 1.25 and 2.5 mg/kg, s.c.); and (c) MP-10 (2.5 mg/kg, s.c.)+various doses of compound B-1a (0, 0.63, 2.5, 10 and 40 mg/kg, s.c.) on apomorphine-induced agitation.

In one aspect, as already stated, the present invention is directed to combinations comprising
a) a PDE2 inhibitor, or a pharmaceutically acceptable salt or a solvate thereof; and
b) one or more PDE10 inhibitor(s), or a pharmaceutically acceptable salt or a solvate thereof.

In a particular embodiment, a) is a compound of Formula (I),

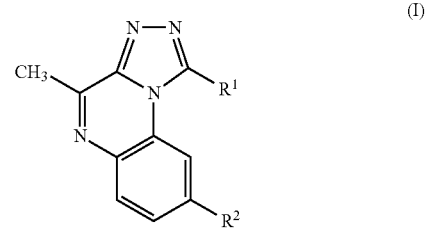

or a stereochemically isomeric form thereof,
wherein
$R^1$ is phenyl or pyridinyl each optionally substituted with 1 or 2 substituents independently selected from the group consisting of halo, ($C_{3-6}$cycloalkyl)$C_{1-3}$alkyloxy and $C_{1-6}$alkyloxy; and
$R^2$ is —$CH_2$—$NR^3R^4$;
wherein
$R^3$ is hydrogen or methyl;
$R^4$ is $C_{1-3}$alkyl; or
$NR^3R^4$ is morpholinyl;
or a pharmaceutically acceptable salt or a solvate thereof.

In a further embodiment, a) is a compound of Formula (I), as described herein, wherein
$R^1$ is phenyl substituted with halo and $C_{1-6}$alkyloxy, or pyridinyl substituted with $C_{1-6}$alkyloxy or ($C_{3-6}$cycloalkyl)

$C_{1-3}$alkyloxy; and $R^2$ is as previously defined; or a pharmaceutically acceptable salt or a solvate thereof.

In a further embodiment, a) is a compound of Formula (I), as described herein, wherein
$R^1$ is phenyl substituted with chloro and $C_{1-6}$alkyloxy, in particular ethoxy, isopropoxy or butoxy; or pyridinyl substituted with $C_{1-6}$alkyloxy or $(C_{3-6}$cycloalkyl)$C_{1-3}$alkyloxy, in particular butoxy or cyclopropylmethoxy; and
$R^2$ is —$CH_2$—$NHCH_3$, —$CH_2$—$N(CH_3)_2$ or —$CH_2$-(4-morpholinyl);
or a pharmaceutically acceptable salt or a solvate thereof.

In an additional embodiment of the present invention, the compound of Formula (I) is selected from
1-[1-(2-Chlorophenyl)-4-methyl[1,2,4]triazolo[4,3-a]quinoxalin-8-yl]-N,N-dimethylmethanamine;
1-(2-Chlorophenyl)-4-methyl-8-(morpholin-4-ylmethyl)[1,2,4]triazolo[4,3-a]quinoxaline;
N-{[1-(2-Chlorophenyl)-4-methyl[1,2,4]triazolo[4,3-a]quinoxalin-8-yl]methyl}ethanamine;
1-(2-Chloro-4-fluorophenyl)-4-methyl-8-(morpholin-4-ylmethyl) [1,2,4]triazolo[4,3-a]quinoxaline;
1-(2-Chloro-6-fluorophenyl)-4-methyl-8-(morpholin-4-ylmethyl) [1,2,4]triazolo[4,3-a]quinoxaline;
1-(5-Methoxypyridin-3-yl)-4-methyl-8-(morpholin-4-ylmethyl) [1,2,4]triazolo[4,3-a]quinoxaline;
1-(2-Chloro-5-methoxyphenyl)-4-methyl-8-(morpholin-4-ylmethyl)[1,2,4]triazolo[4,3-a]quinoxaline;
1-(5-Butoxypyridin-3-yl)-4-methyl-8-(morpholin-4-ylmethyl)[1,2,4]triazolo[4,3-a]quinoxaline or a hydrochloride salt or an oxalate salt thereof;
1-(5-Butoxy-2-chlorophenyl)-4-methyl-8-(morpholin-4-ylmethyl) [1,2,4]triazolo[4,3-a]quinoxaline or a hydrochloride salt thereof;
1-[2-Chloro-5-(1-methylethoxy)phenyl]-4-methyl-8-(morpholin-4-ylmethyl)[1,2,4]triazolo[4,3-a]quinoxaline or a hydrochloride salt thereof;
N-({1-[2-Chloro-5-(1-methylethoxy)phenyl]-4-methyl[1,2,4]triazolo[4,3-a]quinoxalin-8-yl}methyl)ethanamine or a hydrochloride salt thereof;
1-[1-(2-Chloro-5-propoxyphenyl)-4-methyl[1,2,4]triazolo[4,3-a]quinoxalin-8-yl]-N,N-dimethylmethanamine or a hydrochloride salt thereof;
1-{1-[2-Chloro-5-(1-methylethoxy)phenyl]-4-methyl[1,2,4]triazolo[4,3-a]quinoxalin-8-yl}-N,N-dimethylmethanamine;
1-[1-(5-Butoxy-2-chlorophenyl)-4-methyl[1,2,4]triazolo[4,3-a]quinoxalin-8-yl]-N,N-dimethylmethanamine;
1-[1-(2-Chloro-5-ethoxyphenyl)-4-methyl[1,2,4]triazolo[4,3-a]quinoxalin-8-yl]-N,N-dimethylmethanamine;
N-{[1-(2-Chloro-5-ethoxyphenyl)-4-methyl[1,2,4]triazolo[4,3-a]quinoxalin-8-yl]methyl}ethanamine;
N-{[1-(2-Chloro-5-ethoxyphenyl)-4-methyl[1,2,4]triazolo[4,3-a]quinoxalin-8-yl]methyl}ethanamine or a hydrochloride salt thereof;
1-(2-Chloro-5-ethoxyphenyl)-4-methyl-8-(morpholin-4-ylmethyl)[1,2,4]triazolo[4,3-a]quinoxaline or a hydrochloride salt thereof;
N-{[1-(2-Chloro-5-propoxyphenyl)-4-methyl[1,2,4]triazolo[4,3-a]quinoxalin-8-yl]methyl}ethanamine;
1-(2-Chloro-5-propoxyphenyl)-4-methyl-8-(morpholin-4-ylmethyl) [1,2,4]triazolo[4,3-a]quinoxaline or a hydrochloride salt thereof;
N-{[1-(5-Butoxy-2-chlorophenyl)-4-methyl[1,2,4]triazolo[4,3-a]quinoxalin-8-yl]methyl}propan-2-amine;
N-{[1-(5-Butoxypyridin-3-yl)-4-methyl[1,2,4]triazolo[4,3-a]quinoxalin-8-yl]methyl}ethanamine or a hydrochloride salt thereof;

N-{[1-(5-Butoxypyridin-3-yl)-4-methyl[1,2,4]triazolo[4,3-a]quinoxalin-8-yl]methyl}propan-2-amine or a hydrochloride salt thereof;
4-Methyl-8-(morpholin-4-ylmethyl)-1-(5-propoxypyridin-3-yl)[1,2,4]triazolo[4,3-a]quinoxaline or a hydrochloride salt thereof;
N-{[4-Methyl-1-(5-propoxypyridin-3-yl)[1,2,4]triazolo[4,3-a]quinoxalin-8-yl]methyl}ethanamine or a hydrochloride salt thereof;
1-[5-(Cyclopropylmethoxy)pyridin-3-yl]-4-methyl-8-(morpholin-4-ylmethyl)[1,2,4]triazolo[4,3-a]quinoxaline or a hydrochloride salt thereof;
N-({1-[5-(Cyclopropylmethoxy)pyridin-3-yl]-4-methyl[1,2,4]triazolo[4,3-a]quinoxalin-8-yl}methyl)ethanamine or a hydrochloride salt thereof;
1-[1-(5-Butoxypyridin-3-yl)-4-methyl[1,2,4]triazolo[4,3-a]quinoxalin-8-yl]-N,N-dimethylmethanamine or a hydrochloride salt thereof;
1-[1-(5-Butoxy-2-chlorophenyl)-4-methyl[1,2,4]triazolo[4,3-a]quinoxalin-8-yl]-N-methylmethanamine or a hydrochloride salt thereof;
1-{1-[5-(Cyclopropylmethoxy)pyridin-3-yl]-4-methyl[1,2,4]triazolo[4,3-a]quinoxalin-8-yl}-N,N-dimethylmethanamine or a hydrochloride salt thereof;
N-({1-[5-(Cyclopropylmethoxy)pyridin-3-yl]-4-methyl[1,2,4]triazolo[4,3-a]quinoxalin-8-yl}methyl)propan-2-amine or a hydrochloride salt thereof;
1-[1-(5-Butoxypyridin-3-yl)-4-methyl[1,2,4]triazolo[4,3-a]quinoxalin-8-yl]-N-methylmethanamine or a hydrochloride salt thereof; and
1-(5-Butoxy-6-chloropyridin-3-yl)-4-methyl-8-(morpholin-4-ylmethyl)[1,2,4]triazolo[4,3-a]quinoxaline;
or a pharmaceutically acceptable salt or a solvate thereof.

In an additional embodiment, the compound of Formula (I) is selected from the group of
1-(5-Butoxypyridin-3-yl)-4-methyl-8-(morpholin-4-ylmethyl)[1,2,4]triazolo[4,3-a]quinoxaline or a hydrochloride salt or an oxalate salt thereof;
1-[2-Chloro-5-(1-methylethoxy)phenyl]-4-methyl-8-(morpholin-4-ylmethyl)[1,2,4]triazolo[4,3-a]quinoxaline or a hydrochloride salt thereof;
1-{1-[2-Chloro-5-(1-methylethoxy)phenyl]-4-methyl[1,2,4]triazolo[4,3-a]quinoxalin-8-yl}-N,N-dimethylmethanamine;
1-[1-(5-Butoxy-2-chlorophenyl)-4-methyl[1,2,4]triazolo[4,3-a]quinoxalin-8-yl]-N,N-dimethylmethanamine;
1-[5-(Cyclopropylmethoxy)pyridin-3-yl]-4-methyl-8-(morpholin-4-ylmethyl)[1,2,4]triazolo[4,3-a]quinoxaline or a hydrochloride salt thereof;
1-[1-(5-Butoxypyridin-3-yl)-4-methyl[1,2,4]triazolo[4,3-a]quinoxalin-8-yl]-N,N-dimethylmethanamine or a hydrochloride salt thereof; and
1-[1-(5-Butoxy-2-chlorophenyl)-4-methyl[1,2,4]triazolo[4,3-a]quinoxalin-8-yl]-N-methylmethanamine or a hydrochloride salt thereof.

In a further embodiment the compound of Formula (I) is

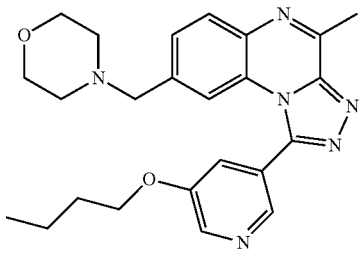 [SMILES: CCCCOc1cncc(-c2nnc3c(C)nc4ccc(CN5CCOCC5)cc4n23)c1]

or a pharmaceutically acceptable salt or a solvate thereof as defined herein, in particular a hydrochloride salt thereof (compound B-1a)

Radiolabelled compounds of Formula (I), for example,
1-(5-Butoxypyridin-3-yl)-4-methyl-8-[morpholin-4-yl($^3H_1$)methyl][1,2,4]triazolo[4,3-a]quinoxaline; and
1-[2-Chloro-6-($^{18}F$)fluorophenyl]-4-methyl-8-(morpholin-4-ylmethyl)[1,2,4]triazolo[4,3-a]quinoxaline;
and the pharmaceutically acceptable salts and the solvates thereof,
can be used on their own or in compositions comprising said particular compounds, for imaging a tissue, cells or a host, in vitro or in vivo.

Thus, the invention also relates in particular to a compound of Formula [$^3H$]-B1a

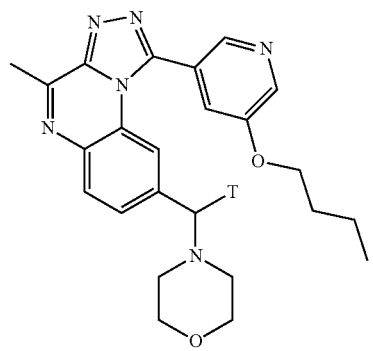

or a pharmaceutically acceptable salt or a solvate thereof,
or a sterile solution comprising said compound of Formula [$^3H$]-B1a for use in imaging a tissue, cells or a host, in vitro or in vivo, in particular in vivo.

Thus, the invention also relates in particular to a compound of Formula [$^3H$]-B1a

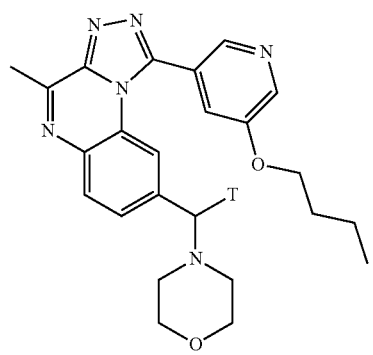

or a pharmaceutically acceptable salt or a solvate thereof,
or a sterile solution comprising said compound of Formula [$^3H$]-B1a intended for use in imaging a tissue or cells n vitro.

The invention also relates to the use of a compound of Formula [$^3H$]-B1a

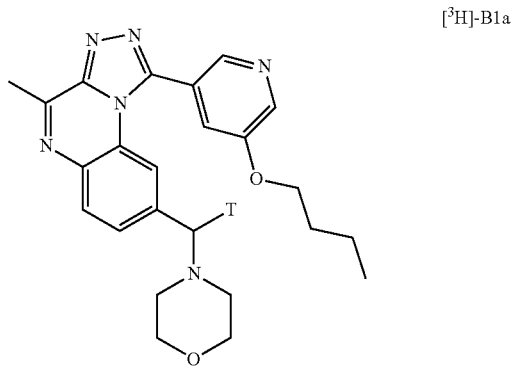

or a pharmaceutically acceptable salt or a solvate thereof,
or a sterile solution comprising said compound of Formula [$^3H$]-B1a for imaging a tissue or cells in vitro.

In a particular embodiment, the b) component of the combination is a PDE10 inhibitor selected from MP-10, PQ-10, TP-10, papaverine, and the compounds disclosed in WO 2011/051324 and in WO 2011/110545. Said compounds disclosed in WO 2011/051324 and in WO 2011/110545 are referred to herein as compounds of Formula (II) and compounds of Formula (III).

In another embodiment, the b) component of the combination is a PDE10 inhibitor selected from the group of MP-10, PQ-10, TP-10 and papaverine.

Such b) components correspond with compounds known from the art, thus MP-10 is 2-{[4-(1-methyl-4-pyridin-4-yl-1H-pyrazol-3-yl)phenoxy]methyl}quinoline [CAS 898562-94-2]; PQ-10 is 6,7-dimethoxy-4-[(3R)-3-(quinoxalin-2-yloxy)pyrrolidin-1-yl]quinazoline [CAS 927691-21-2]; TP-10 is 2-({4-[4-pyridin-4-yl-1-(2,2,2-trifluoroethyl)-1H-pyrazol-3-yl]phenoxy}methyl)quinoline [CAS 898563-00-3]; and papaverine or papaverine hydrochloride is 1-[(3,4-dimethoxyphenyl)methyl]-6,7-dimethoxy-isoquinoline or its hydrochloride (1:1) [CAS 61-25-6]. In a particular embodiment, the PDE10 inhibitor is selected from MP-10 and TP-10. In a further embodiment, the PDE10 inhibitor is MP-10.

The compounds disclosed in WO 2011/051324 are herein referred to as compounds of Formula (II)

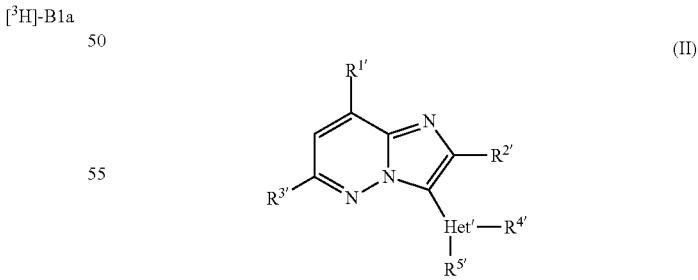

and the stereoisomeric forms thereof,
wherein
$R^{1'}$ is pyridinyl; pyridinyl optionally substituted with halogen, $C_{1-4}$alkyl, trifluoromethyl or $C_{1-4}$alkyloxy; tetrahydropyranyl; or $NR^{6'}R^{7'}$;
$R^{2'}$ is hydrogen, $C_{1-4}$alkyl, trifluoromethyl, $C_{3-8}$cycloalkyl, or $C_{1-4}$alkyloxy;

$R^{3'}$ is hydrogen, chloro, $C_{1-4}$alkyl, trifluoromethyl, or $C_{3-8}$cycloalkyl;

Het' is a 5- or 6-membered heterocyclic ring selected from the group consisting of pyridinyl, pyrimidinyl, pyridazinyl, pyrrolyl, oxazolyl, thiazolyl, imidazolyl, pyrazolyl, isothiazolyl, isoxazolyl, oxadiazolyl and triazolyl;

$R^{4'}$ is hydrogen, $C_{1-4}$alkyl, trifluoromethyl$C_{0-4}$alkyl, hydroxy$C_{1-4}$alkyl, difluorocyclopropylmethyl, cyclopropyldifluoroethyl, $C_{3-8}$cycloalkyl, $C_{1-4}$alkyloxy$C_{1-5}$alkyl, $C_{1-4}$alkyloxy, trifluoromethyl$C_{0-4}$alkyloxy, $C_{3-8}$cycloalkyl$C_{1-4}$alkyloxy, $C_{3-8}$cycloalkyl$C_{1-4}$alkyl, $C_{1-6}$alkyloxy$C_{1-4}$alkyloxy, tetrahydropyranyl, pyridinylmethyl, $NR^{6a}R^{7a}C_{1-4}$alkyl or $NR^{6a}R^{7a}$;

$R^{5'}$ is hydrogen or $C_{1-4}$alkyl;

$R^{6'}$, $R^{6a'}$, $R^{7'}$ and $R^{7a'}$ are each independently hydrogen, or $C_{1-4}$alkyl, or taken together with N can be a radical of Formula (a'), (b') or (c')

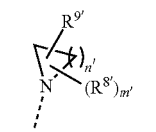

(a')

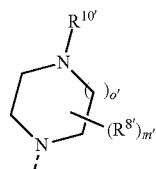

(b')

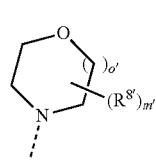

(c')

wherein each $R^{8'}$, if present, independently of one another is $C_{1-4}$alkyl;

$R^{9'}$ is hydrogen or $C_{1-4}$alkyloxy;

$R^{10'}$ is hydrogen or $C_{1-4}$alkyl;

m' is 0, 1, 2, 3, 4 or 5;

n' is 2, 3, 4, 5 or 6;

o' is 1 or 2;

and the pharmaceutically acceptable salts and the solvates thereof.

Particular compounds of Formula (II) are selected from

3-[6-(2-methoxyethyl)-3-pyridinyl]-2-methyl-8-(4-morpholinyl)-imidazo[1,2-b]pyridazine hydrochloride, 3-[6-(2-methoxyethyl)-3-pyridinyl]-2-methyl-8-(4-morpholinyl)-imidazo[1,2-b]pyridazine maleate, 3-[6-(2-methoxyethyl)-3-pyridinyl]-2-methyl-8-(4-morpholinyl)-imidazo[1,2-b]pyridazine monohydrate, 3-[6-(2-methoxyethoxy)-3-pyridinyl]-2-methyl-8-(4-pyridinyl)-imidazo[1,2-b]pyridazine hydrochloride, 2-cyclopropyl-3-[6-(2-methoxy-2-methylpropyl)-3-pyridinyl]-8-(4-morpholinyl)-imidazo[1,2-b]pyridazine hydrochloride, 3-[6-(2-methoxy-2-methylpropyl)-3-pyridinyl]-2,6-dimethyl-8-(4-pyridinyl)-imidazo[1,2-b]pyridazine, 2-cyclopropyl-3-[6-(2-methoxy-2-methylpropyl)-3-pyridinyl]-8-(4-pyridinyl)-imidazo[1,2-b]pyridazine, 5-[2-cyclopropyl-8-(4-morpholinyl)imidazo[1,2-b]pyridazin-3-yl]-α,α-dimethyl-2-pyridineethanol, 3-[6-(4-morpholinyl)-3-pyridinyl]-8-(4-pyridinyl)-imidazo[1,2-b]pyridazine, 2,6-dimethyl-8-(4-morpholinyl)-3-[6-(4-morpholinyl)-3-pyridinyl]-imidazo[1,2-b]pyridazine, 2-cyclopropyl-6-methyl-3-[6-(4-morpholinyl)-3-pyridinyl]-8-(4-pyridinyl)-imidazo[1,2-b]pyridazine, 2-cyclopropyl-3-[6-(2-methoxyethoxy)-3-pyridinyl]-6-methyl-8-(4-pyridinyl)-imidazo[1,2-b]pyridazine, 2-methyl-8-(4-morpholinyl)-3-[2-(4-morpholinyl)-4-pyridinyl]-imidazo[1,2-b]pyridazine, 3-{1-[(2,2-difluorocyclopropyl)methyl]-1H-pyrazol-4-yl}-2-methyl-8-morpholin-4-ylimidazo[1,2-b]pyridazine, 2-methyl-3-[1-(2-methylpropyl)-1H-pyrazol-4-yl]-8-(4-pyridinyl)-imidazo[1,2-b]pyridazine, 6-cyclopropyl-3-[1-(2-methoxyethyl)-1H-pyrazol-4-yl]-2-methyl-8-(4-morpholinyl)-imidazo[1,2-b]pyridazine, 2-ethyl-3-[1-(2-methoxyethyl)-1H-pyrazol-4-yl]-8-(4-morpholinyl)-imidazo[1,2-b]pyridazine, 3-[1-[(2S)-2-methoxypropyl]-1H-pyrazol-4-yl]-2-methyl-8-(4-morpholinyl)-imidazo[1,2-b]pyridazine, 3-[1-(2-methoxyethyl)-1H-pyrazol-4-yl]-2,6-dimethyl-8-(4-morpholinyl)-imidazo[1,2-b]pyridazine, 3-[1-(2-methoxyethyl)-1H-pyrazol-4-yl]-2,6-dimethyl-8-(4-pyridinyl)-imidazo[1,2-b]pyridazine, 2-methyl-8-(4-pyridinyl)-3-[1-(2,2,2-trifluoroethyl)-1H-pyrazol-4-yl]-imidazo[1,2-b]pyridazine, 2-cyclopropyl-3-[1-(2-methoxyethyl)-1H-pyrazol-4-yl]-8-(4-pyridinyl)-imidazo[1,2-b]pyridazine, 2-cyclopropyl-3-[1-(2-methoxy-2-methylpropyl)-1H-pyrazol-4-yl]-8-(4-pyridinyl)-imidazo[1,2-b]pyridazine, 6-chloro-3-[1-(2-methoxyethyl)-1H-pyrazol-4-yl]-2-methyl-8-(4-pyridinyl)-imidazo[1,2-b]pyridazine, and 2-cyclopropyl-3-[1-(2-methylpropyl)-1H-pyrazol-4-yl]-8-(4-pyridinyl)-imidazo[1,2-b]pyridazine.

A particular example of a compound of Formula (II) is Compound A:

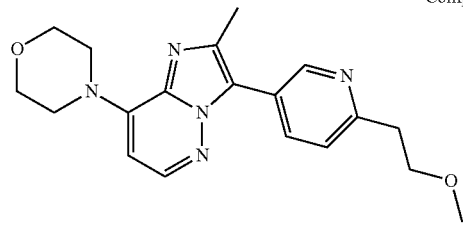

Compound A or a pharmaceutically acceptable salt or a solvate thereof.

The compounds disclosed in WO 2011/110545 are herein referred to as compounds of Formula (III)

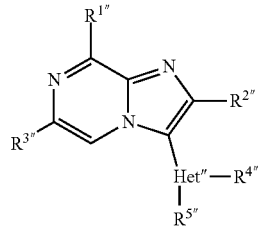

(III)

and the stereoisomeric forms thereof, wherein $R^{1''}$ is selected from the group consisting of a radical of formula (a-1''), (a-2'') and (a-3'');

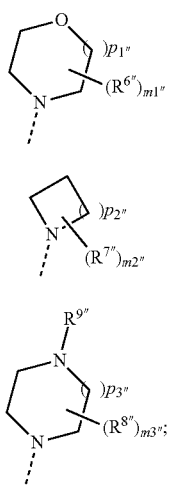

wherein
each $R^{6''}$, $R^{7''}$, and $R^{8''}$ independently is selected from the group consisting of fluoro; $C_{1-4}$alkyl; $C_{1-4}$alkyloxy; and $C_{1-4}$alkyl substituted with 1, 2 or 3 fluoro atoms;
$R^{9''}$ is hydrogen or $C_{1-4}$alkyl;
each $m_{1''}$, $m_{2''}$, and $m_{3''}$ is independently selected from 0, 1, 2, 3 and 4;
$p_{2''}$ is selected from 1, 2, 3 and 4;
each $p_{1''}$ and $p_{3''}$ is independently selected from 1 and 2;
or $R^{1''}$ is selected from the group consisting of unsubstituted pyridinyl; pyridinyl substituted with 1 or 2 substituents selected from the group consisting of halogen, $C_{1-4}$alkyl, trifluoromethyl and $C_{1-4}$alkyloxy; and unsubstituted tetrahydropyranyl;
$R^{2''}$ is selected from the group consisting of hydrogen; $C_{1-4}$alkyl; trifluoromethyl; $C_{3-8}$cycloalkyl; $C_{1-4}$alkyloxy; and cyano;
$R^{3''}$ is selected from the group consisting of hydrogen; $C_{1-4}$alkyl; $C_{3-8}$cycloalkyl; and $C_{1-4}$alkyl substituted with 1, 2 or 3 fluoro atoms;
Het'' is a 5- or 6-membered heterocyclic ring, selected from the group consisting of pyridinyl; pyrimidinyl; pyridazinyl; pyrazinyl; pyrrolyl; oxazolyl; thiazolyl; imidazolyl; pyrazolyl; isothiazolyl; isoxazolyl; oxadiazolyl and triazolyl;
$R^{4''}$ is selected from the group consisting of hydrogen; $C_{1-4}$alkyl; $C_{1-4}$alkyl substituted with 1, 2 or 3 fluoro atoms; (difluorocyclopropyl)methyl; (cyclopropyl)difluoromethyl; hydroxy$C_{1-4}$alkyl; $C_{3-8}$cycloalkyl; ($C_{3-8}$cycloalkyl)-$C_{1-4}$alkyl; $C_{1-4}$alkyloxy$C_{1-6}$alkyl; $C_{1-4}$alkyloxy; $C_{1-4}$alkyloxy substituted with 1, 2 or 3 fluoro atoms; ($C_{3-8}$cycloalkyl)$C_{1-4}$alkyloxy; ($C_{1-4}$alkyloxy$C_{1-4}$alkyl)oxy; ($C_{1-4}$alkyl)-carbonyl; ($C_{1-4}$alkyl)carbonyl$C_{1-4}$alkyl; ($C_{3-8}$cycloalkyl)carbonyl; ($C_{3-8}$cycloalkyl)-carbonyl$C_{1-4}$alkyl; unsubstituted phenyl; phenyl substituted with 1 or 2 substituents selected from the group consisting of halogen, $C_{1-4}$alkyl, trifluoromethyl, trifluoromethoxy, cyano and $C_{1-4}$alkyloxy; unsubstituted benzyl; benzyl substituted with 1 or 2 substituents selected from the group consisting of halogen, $C_{1-4}$alkyl, trifluoromethyl, trifluoromethoxy, cyano and $C_{1-4}$alkyloxy; unsubstituted tetrahydrofuranyl; tetrahydrofuranylmethyl; unsubstituted tetrahydropyranyl; tetrahydropyranylmethyl; pyridinylmethyl; quinolinylmethyl; ($NR^{10''}R^{11''}$)$C_{1-4}$alkyl; and $NR^{10''}R^{11''}$;
$R^{5''}$ is hydrogen or fluoro;
$R^{10''}$ and $R^{11''}$ are independently selected from hydrogen and $C_{1-4}$alkyl, or taken together with the ring nitrogen atom may form a radical of Formula (b-1''), (b-2'') or (b-3'')

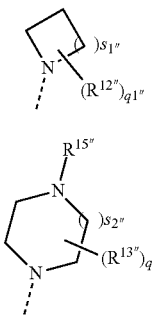

wherein
each $R^{12''}$, $R^{13''}$ and $R^{14''}$ independently is $C_{1-4}$alkyl or $C_{1-4}$alkyloxy;
$R^{15''}$ is hydrogen or $C_{1-4}$alkyl;
each $q_{1''}$, $q_{2''}$ and $q_{3''}$ is independently selected from 0, 1, 2, 3 and 4;
$s_{1''}$ is selected from 1, 2, 3 and 4;
each $s_{2''}$ and $s_{3''}$ is independently selected from 1 and 2;
and the pharmaceutically acceptable salts and the solvates thereof.

Particular compounds of Formula (III) are selected from
3-[1-(2-methoxyethyl)-1H-pyrazol-4-yl]-2-methyl-8-(4-morpholinyl)-imidazo[1,2-a]pyrazine;
3-[1-(2-methoxyethyl)-1H-pyrrol-3-yl]-2-methyl-8-(4-morpholinyl)-imidazo[1,2-a]pyrazine;
3-[6-(2-methoxyethyl)-3-pyridinyl]-2-methyl-8-(4-morpholinyl)-imidazo[1,2-a]pyrazine;
2-methyl-3-[2-(2-methylpropyl)-5-thiazolyl]-8-(4-morpholinyl)-imidazo[1,2-a]pyrazine;
3-[6-(2-methoxyethyl)-3-pyridinyl]-2-methyl-8-(4-pyridinyl)-imidazo[1,2-a]pyrazine;
3-[6-(2-methoxyethoxy)-3-pyridinyl]-2-methyl-8-(4-morpholinyl)-imidazo[1,2-a]pyrazine;
3-(6-cyclopropyl-3-pyridinyl)-2-methyl-8-(4-morpholinyl)-imidazo[1,2-a]pyrazine;
2-methyl-8-(4-morpholinyl)-3-[6-(1-piperazinyl)-3-pyridinyl]-imidazo[1,2-a]pyrazine;
2-methyl-8-(4-morpholinyl)-3-[6-(tetrahydro-2H-pyran-4-yl)-3-pyridinyl]-imidazo[1,2-a]pyrazine;
3-[6-(1-methoxy-1-methylethyl)-3-pyridinyl]-2-methyl-8-(4-morpholinyl)-imidazo[1,2-a]pyrazine;
3-[6-(ethoxymethyl)-3-pyridinyl]-2-methyl-8-(4-morpholinyl)-imidazo[1,2-a]pyrazine; and
3-[2-(2-methoxyethyl)-5-pyrimidinyl]-2-methyl-8-(4-morpholinyl)-imidazo[1,2-a]pyrazine.

A particular example of a compound of Formula (III) is Compound B:

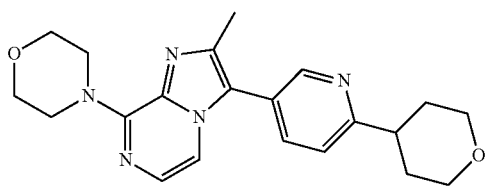

Compound B or a pharmaceutically acceptable salt or a solvate thereof.

In a further embodiment, the present invention relates to a combination comprising
a) a compound of formula

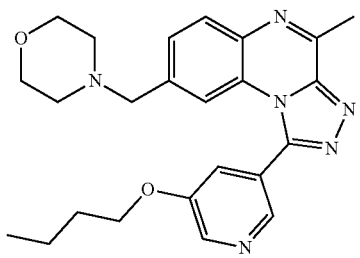 [SMILES: CCCCOc1cncc(-c2nnc3c(C)nc4ccc(CN5CCOCC5)cc4n23)c1]

or a pharmaceutically acceptable salt or a solvate thereof as defined herein, in particular a hydrochloride salt thereof (compound B-1a); and
b) one or more PDE10 inhibitor(s) selected from the group of MP-10, a compound of formula

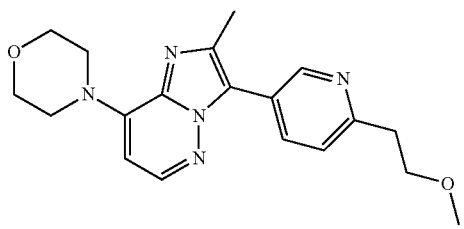 [SMILES: COCCc1ccc(-c2c(C)nc3c(N4CCOCC4)ccnn23)cn1]

(compound A) as defined above or a pharmaceutically acceptable salt or a solvate thereof as defined herein, and a compound of formula

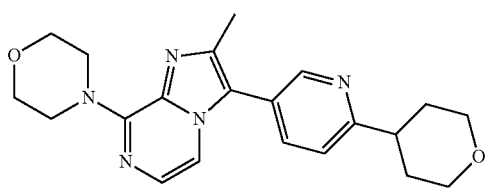 [SMILES: Cc1nc2c(N3CCOCC3)nccn2c1-c1ccc(C2CCOCC2)nc1]

(compound B) as defined above or a pharmaceutically acceptable salt or a solvate thereof as defined herein.

In an additional embodiment the present invention relates to combinations comprising
a) a compound of formula (I),

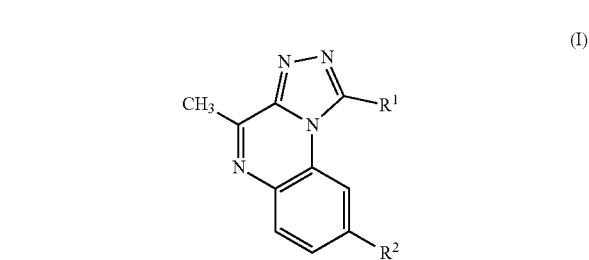

or a stereochemically isomeric form thereof,
wherein
$R^1$ is phenyl or pyridinyl each optionally substituted with 1 or 2 substituents independently selected from the group consisting of halo, $(C_{3-6}cycloalkyl)C_{1-3}alkyloxy$ and $C_{1-6}alkyloxy$; and
$R^2$ is $-CH_2-NR^3R^4$;
wherein
$R^3$ is hydrogen or methyl;
$R^4$ is $C_{1-3}alkyl$; or
$NR^3R^4$ is morpholinyl;
or a pharmaceutically acceptable salt or a solvate thereof; and
b) one or more PDE10 inhibitor(s) selected from the group of MP-10, PQ-10, TP-10 and papaverine.

The present invention also relates to products containing as first active ingredient a) a compound of Formula (I) or a pharmaceutically acceptable salt or a solvate thereof, as defined herein, and as a second active ingredient b) one or more PDE10 inhibitors selected from the group of MP-10, PQ-10, TP-10 and papaverine, as combined preparations for simultaneous, separate or sequential use in the treatment of patients suffering from neurological or psychiatric disorders, or endocrinological or metabolic diseases.

Illustrative of the invention is a pharmaceutical composition comprising a pharmaceutically acceptable carrier and any of the combinations described above. An illustration of the invention is a pharmaceutical composition made by mixing any of the combinations described above and a pharmaceutically acceptable carrier. Illustrating the invention is a process for making a pharmaceutical composition comprising mixing any of the combinations described above and a pharmaceutically acceptable carrier.

In a further embodiment, the invention relates to the use of a compound of Formula (I) or a pharmaceutically acceptable salt or a solvate thereof for the potentiation of the effect of one or more PDE10 inhibitor(s) selected from the group of MP-10, PQ-10, TP-10 and papaverine.

The invention also relates to a compound of Formula (I) or a pharmaceutically acceptable salt or a solvate thereof, as defined herein, for use in the enhancement of the therapeutic effect of one or more PDE10 inhibitor(s) selected from the group of MP-10, PQ-10, TP-10 and papaverine, in patients suffering from neurological or psychiatric disorders, or endocrinological or metabolic diseases.

Further, the present invention also concerns the use of a compound of Formula (I) or a pharmaceutically acceptable salt or a solvate thereof, as defined herein, for the preparation of a medicament for enhancing the therapeutic effect of one or more PDE10 inhibitor(s) selected from the group of MP-10, PQ-10, TP-10 and papaverine in patients suffering from neurological or psychiatric disorders, or endocrinological or metabolic diseases.

The invention further relates to the use of one or more PDE10 inhibitor(s) selected from the group of MP-10, PQ-10, TP-10 and papaverine, for the potentiation of the effect of a compound of formula (I) or a pharmaceutically acceptable salt or a solvate thereof. The invention also relates to one or more PDE10 inhibitor(s) selected from the group of MP-10, PQ-10, TP-10 and papaverine, for use in the enhancement of the therapeutic effect of a compound of Formula (I) or a pharmaceutically acceptable salt or a solvate thereof, as defined herein. In a further aspect, the present invention also concerns the use of one or more PDE10 inhibitor(s) selected from the group of MP-10, PQ-10, TP-10 and papaverine, for the preparation of a medicament for enhancing the therapeutic effect of a compound of Formula (I) or a pharmaceutically acceptable salt or a solvate thereof, as defined herein, in patients suffering from neurological or psychiatric disorders, or endocrinological or metabolic diseases.

The invention further relates to a method of treating a neurological or psychiatric disorder, or an endocrinological or a metabolic disease comprising administering to a subject in need thereof a therapeutically effective amount of a combination comprising a) a compound of Formula (I) or a pharmaceutically acceptable salt or a solvate thereof as defined herein and b) one or more PDE10 inhibitor(s) selected from the group of MP-10, PQ-10, TP-10 and papaverine or a therapeutically effective amount of a pharmaceutical composition as described above.

The invention further relates to a method of enhancing the therapeutic effect of a compound of Formula (I) or a pharmaceutically acceptable salt or a solvate thereof, as defined herein, comprising administering to a subject in need thereof a therapeutically effective amount of a combination comprising a) a compound of Formula (I) or a pharmaceutically acceptable salt or a solvate thereof as defined herein and b) one or more PDE10 inhibitor(s) selected from the group of MP-10, PQ-10, TP-10 and papaverine or a therapeutically effective amount of a pharmaceutical composition as described above.

The invention further relates to a method of enhancing the therapeutic effect of one or more PDE10 inhibitor(s) selected from the group of MP-10, PQ-10, TP-10 and papaverine, comprising administering to a subject in need thereof a therapeutically effective amount of a combination comprising a) a compound of Formula (I), as defined herein and b) one or more PDE10 inhibitor(s) selected from the group of MP-10, PQ-10, TP-10 and papaverine or a therapeutically effective amount of a pharmaceutical composition as described above.

DEFINITIONS

"Halo" shall denote fluoro, chloro and bromo; "$C_{1-6}$alkyl", "$C_{1-4}$alkyl" and "$C_{1-3}$alkyl" as used herein as a group or part of a group shall denote a straight or branched saturated alkyl group having 1, 2, 3, 4, 5, or 6 carbon atoms or 1, 2, 3, or 4 carbon atoms, or 1, 2 or 3 carbon atoms, respectively e.g. methyl, ethyl, 1-propyl, 2-propyl, 1-butyl, 2-butyl, 2-methylpropyl, tert-butyl, 1-pentyl, 2-methylbutyl, pentan-2-yl, 2-methylbutan-2-yl or hexyl and the like; "$C_{0-4}$alkyl" as employed herein alone or as part of another group, unless otherwise stated, refers to a saturated straight or branched hydrocarbon radical, having from 0 to 4 carbon atoms; "$C_{1-6}$alkyloxy", "$C_{1-4}$alkyloxy" and "$C_{1-3}$alkyloxy" shall denote an ether radical wherein $C_{1-6}$alkyl, $C_{1-4}$alkyl and $C_{1-3}$alkyl are as defined before; "$C_{3-8}$cycloalkyl" and "$C_{3-6}$cycloalkyl" shall denote cyclopropyl, cyclobutyl, cyclopentyl, cyclohexyl, and cycloheptyl and cyclooctyl; "($C_{3-6}$cycloalkyl)$C_{1-3}$alkyl" shall denote a $C_{3-6}$cycloalkyl as defined before, bound to the rest of the molecule through a $C_{1-3}$alkyl radical as defined before.

The term "subject" as used herein, refers to an animal, preferably a mammal, most preferably a human, who is or has been the object of treatment, observation or experiment.

As used herein, the term "therapeutically effective amount", means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. More particularly, in the present invention directed to combination therapy comprising administration of a PDE2 inhibitor, in particular of a compound of formula (I), or a pharmaceutically acceptable salt or a solvate thereof and one or more PDE10 inhibitors selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, "therapeutically effective amount" shall mean that amount of the combination of agents taken together so that the combined effect elicits the desired biological or medicinal response. For example, the therapeutically effective amount of PDE2 inhibitor, in particular of compound of formula (I), or pharmaceutically acceptable salt or solvate thereof and PDE10 inhibitor(s) would be the amount of PDE2 inhibitor, in particular of compound of formula (I), or pharmaceutically acceptable salt or solvate thereof and the amount of PDE10 inhibitor(s) that when taken together or sequentially have a combined effect that is therapeutically effective.

Further, it will be recognized by one skilled in the art that in the case of co-therapy with a therapeutically effective amount, as in the example above, the amount of PDE2 inhibitor, in particular of compound of formula (I), or pharmaceutically acceptable salt or solvate thereof and/or the amount of PDE10 inhibitor(s) individually may or may not be therapeutically effective.

As used herein, the term "composition" is intended to encompass a product comprising the specified ingredients in the specified amounts, as well as any product which results, directly or indirectly, from combinations of the specified ingredients in the specified amounts.

In accordance with the methods of the present invention, the individual components of the combination can be administered by any suitable means, simultaneously, sequentially, separately or in a single pharmaceutical formulation. Where the PDE2 inhibitor, in particular the compound of Formula (I), or pharmaceutically acceptable salt or solvate thereof and the PDE10 inhibitor(s) are administered in separate dosage forms, the number of dosages administered per day for each compound may be the same or different. The PDE2 inhibitor, in particular the compound of Formula (I), or pharmaceutically acceptable salt or solvate thereof and the PDE10 inhibitor(s) may be administered via the same or different routes of administration. Examples of suitable methods of administration include, but are not limited to, oral, intravenous (iv), intramuscular (im), subcutaneous (sc), transdermal, nasal and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

The PDE2 inhibitor, in particular the compound of formula (I), or a pharmaceutically acceptable salt or solvate thereof and the PDE10 inhibitor(s) may be administered according to simultaneous or alternating regimens, at the same or different times during the course of the therapy, concurrently in divided or single forms. The instant invention is therefore to be understood as embracing all such regimens of simultaneous or alternating treatment and the term "administering" is to be interpreted accordingly.

Optimal dosages and dosage regimens to be administered may be readily determined by those skilled in the art, and will vary with the mode of administration, the strength of the preparation and the advancement of the disease condition. In addition, factors associated with the particular patient being treated, including patient's sex, age, weight, diet, physical activity, time of administration and concomitant diseases, will result in the need to adjust dosages and/or regimens.

The term "one or more PDE10 inhibitors or inhibitor(s)" as used herein refers to one, two or three PDE10 inhibitors, in particular one PDE10 inhibitor as referred to herein.

The term "host" refers to a mammal, in particular to humans, mice, dogs and rats.

The term "cell" refers to a cell expressing or incorporating the PDE2 enzyme.

It will be appreciated that some of the compounds of Formula (I)-(III) and their pharmaceutically acceptable addition salts and solvates thereof may contain one or more centres of chirality and exist as stereoisomeric forms.

The term "compounds of the invention" as used herein, is meant to include the compounds of Formula (I), and the salts and solvates thereof. As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)-(III)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration.

Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system. The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light. When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I)-(III) is for instance specified as (R), this means that the compound is substantially free of the (S) isomer; when a compound of Formula (I)-(III) is for instance specified as E, this means that the compound is substantially free of the Z isomer; when a compound of Formula (I)-(III) is for instance specified as cis, this means that the compound is substantially free of the trans isomer.

Some of the compounds according to Formula (I)-(III) may also exist in their tautomeric form. Such forms in so far as they may exist, although not explicitly indicated in the above Formula (I)-(III) are intended to be included within the scope of the present invention.

It follows that a single compound may exist in both stereoisomeric and tautomeric form.

In addition, some of the compounds of the present invention may form solvates with water (i.e., hydrates) or common organic solvents, and such solvates are also intended to be encompassed within the scope of this invention.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3H$, $^{11}C$, $^{18}F$, $^{122}I$, $^{123}I$, $^{125}I$ $^{131}I$, $^{75}Br$, $^{76}Br$, $^{77}Br$ and $^{82}Br$. Preferably, the radioactive isotope is selected from the group of $^3H$, $^{11}C$ and $^{18}F$.

For use in medicine, the salts of the compounds of Formula (I)-(III) refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluene-sulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of Formula (I)-(III) were generated according to the nomenclature rules agreed upon by the International Union of Pure and Applied Chemistry (IUPAC) using Advanced Chemical Development, Inc., software (ACD/Name product version 10.01.0.14105, October 2006).

Preparation of the Compounds

The compounds of Formula (I) can generally be prepared by a succession of steps, each of which is known to the skilled person. The transformations of different functional groups present in the final compounds into other functional groups according to Formula (I) can be performed as well by synthesis methods well known to the person skilled in the art. In particular, the compounds can be prepared according to the following synthesis methods.

Preparation of the Final Compounds

Compounds of Formula (I) can be prepared by synthesis methods well known to the person skilled in the art. Compounds of the invention may be prepared, for example, by two different general schemes:

Scheme 1: Synthesis of Compounds of Formula (I)
Method A:

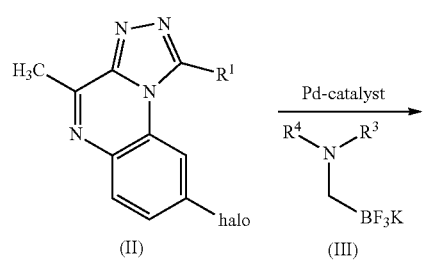

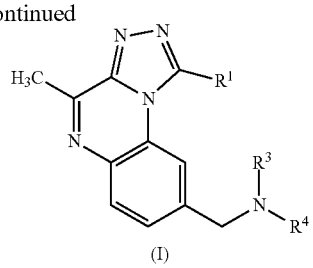

A compound of Formula (II) can react with a compound of Formula (III) in an inert solvent or mixture of solvents, such as, for example, a mixture of tetrahydrofuran and water in presence of a complexing agent such as 2-dichlorohexylphosphino-2',4',6'-triisopropylbiphenyl (XPhos), a palladium catalyst, such as Palladium (II) acetate, and a base such as for example caesium carbonate stirring the reaction mixture at a suitable temperature, such as 110-120° C., using conventional heating or microwave irradiation, for the required time to achieve completion of the reaction, typically 45 minutes for conventional heating. Compounds of Formula (III) can be either commercially available or can be prepared by methods described in chemical literature well known to the skilled person.

Method B:

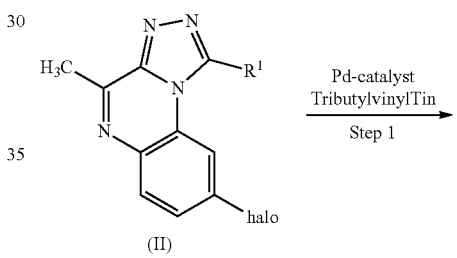

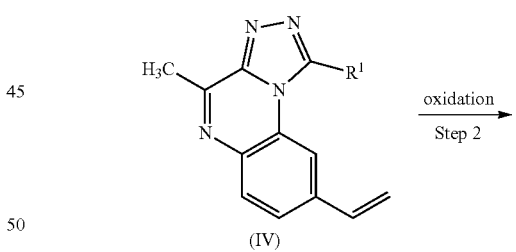

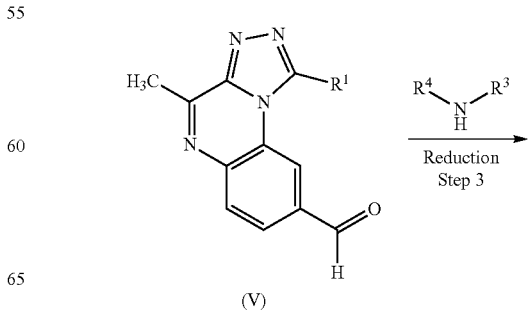

-continued

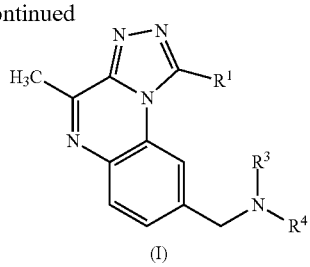

(I)

Step 1: A compound of Formula (II) can react with tributylvinyl tin, in an inert solvent such as, for example, toluene in presence of a palladium catalyst, such as (triphenylphosphine)tetrakis Palladium(0), and a salt such as, for example, lithium chloride stirring the reaction mixture at a suitable temperature, such as 120-130° C., using conventional heating or microwave irradiation, for the required time to achieve completion of the reaction, typically 1 hour for conventional heating. This reaction step affords a compound of Formula (IV).

Step 2: A compound of Formula (IV) can be oxidized by standard procedures well known to the person skilled in the art, such as, for example, by ozonolysis or by reaction with a mixture of osmium tetroxide and sodium periodate yielding a compound of Formula (V).

Step 3: A compound of Formula (V) can react with an amine of formula $NHR^3R^4$, wherein $R^3$ and $R^4$ are as previously defined, in a conventional reductive amination reaction, which is well known to the skilled person. Thus, a compound of Formula (V) can react with an amine of formula $NHR^3R^4$ as previously defined in an inert solvent, such as for example, 1,2-dichloroetane, stirring the reaction mixture at a suitable temperature, typically at 80-120° C. for 10-20 minutes under microwave irradiation, in the presence of a reducing agent, such as tributoxy cyanoborohydride or sodium borohydride. After the addition of the reducing agent the reaction can be stirred either at room temperature or by microwave heating for the required time to achieve completion of the reaction, typically 20 min at 80° C. for microwave heating. This reaction step yields a final compound of Formula (I).

Scheme 2: Synthesis of Compounds of Formula (II)
Method A:

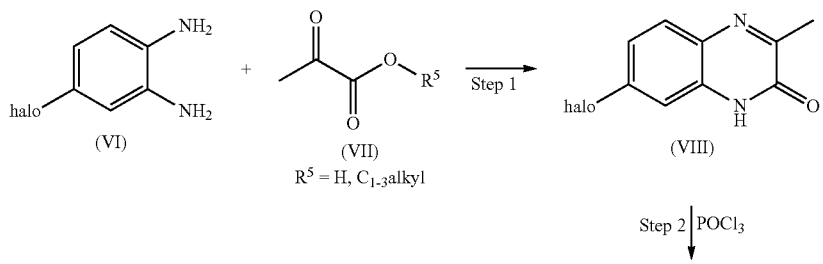

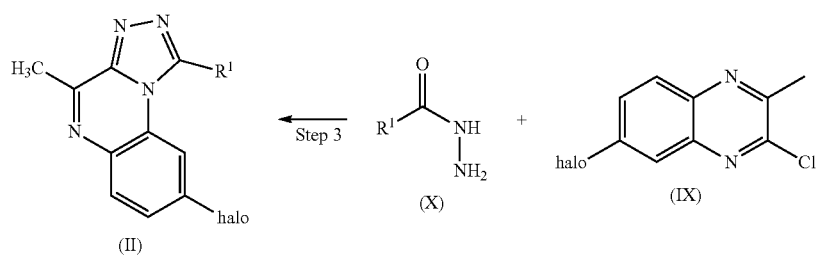

Step 1: An intermediate compound of Formula (VI) can be reacted with a commercially available compound of Formula (VII), wherein $R^5$ is $C_{1-3}$-alkyl such as for example methyl or ethyl in an inert solvent such as, for example, toluene, stirring the reaction mixture at a suitable temperature, typically at 100-130° C., using conventional heating or under microwave irradiation, for the required time to achieve completion of the reaction, typically 3 hours for conventional heating. When $R^5$ is hydrogen the reaction is performed in a mixture of acetic acid and water and the stirring is performed at room temperature overnight. This reaction usually affords a mixture of the two possible regioisomers, which can be separated at this step (to give a regioisomer of Formula (VIII)) or in one of the following steps by chromatographic methods, either by column chromatography or HPLC. Compounds of Formula (VI) are either commercially available or described in chemical literature and can be prepared by simple standard synthetic procedures well known to the skilled person.

Step 2: Intermediate compounds of Formula (VIII) can react, in presence or absence of a solvent such as for example 1,2-dichloroethane, with phosphorous oxychloride, stirring the reaction mixture at a suitable temperature, typically at 100-120° C., using conventional heating or under microwave irradiation, for the required time to achieve completion of the reaction, typically 2-4 hours for conventional heating. This reaction step affords intermediate compounds of Formula (IX).

Step 3: An intermediate compound of Formula (IX) can react with an intermediate compound of Formula (X) in a solvent, such as, for example, ethanol, n-butanol or tetrahydrofuran stirring the reaction mixture at a suitable temperature, typically at 100-160° C., using conventional heating or under microwave irradiation, for the required time to achieve completion of the reaction, typically 15-20 minutes at 160° C. for microwave heating, affording compounds of Formula (II). The intermediate compounds of Formula (X) can be either commercially available or are described in chemical literature and can be prepared by simple standard synthetic procedures well known to the skilled person.

Method B:

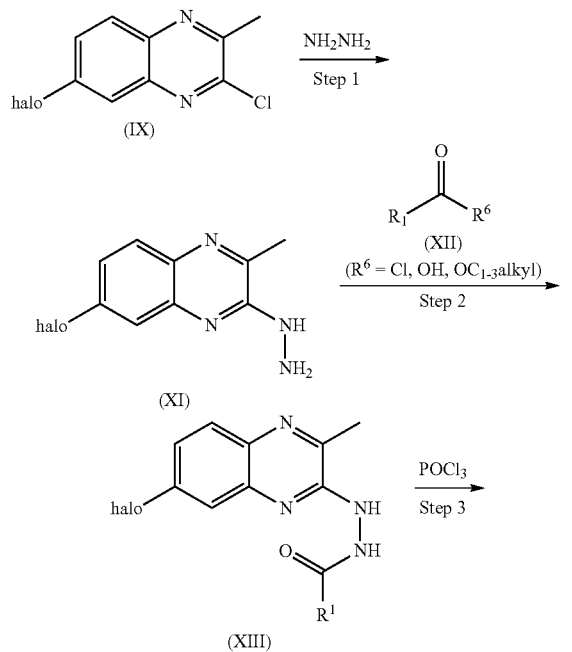

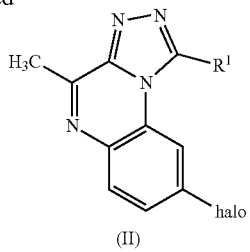

Step 1: Intermediate compounds of Formula (IX) can be treated with hydrazine hydrate in an inert solvent, such as methanol or ethanol, following simple standard synthetic procedures well known to the skilled person yielding intermediate compounds of Formula (XI).

Step 2: Intermediate compounds of Formula (XI) can react with intermediate compounds of Formula (XII) following simple standard synthetic procedures well known to the skilled person to give intermediate compounds of Formula (XIII). Intermediate compounds of Formula (XII) can be either commercially available or synthesized following literature precedents.

Step 3: Intermediate compounds of Formula (XIII) can react, in presence or absence of a solvent such as for example 1,2-dichloroethane, with phosphorous oxychloride, stirring the reaction mixture at a suitable temperature, typically at 80-100° C., using conventional heating or under microwave irradiation, for the required time to achieve completion of the reaction, typically 16 hours for conventional heating. This reaction step affords compounds of Formula (II).

Preparation of Radiolabelled Final Compounds

Scheme 3: Synthesis of Compounds of Formula (I) where $R^2={}^3H$-Radiolabelled —$CH_2$—$NR^3R^4$

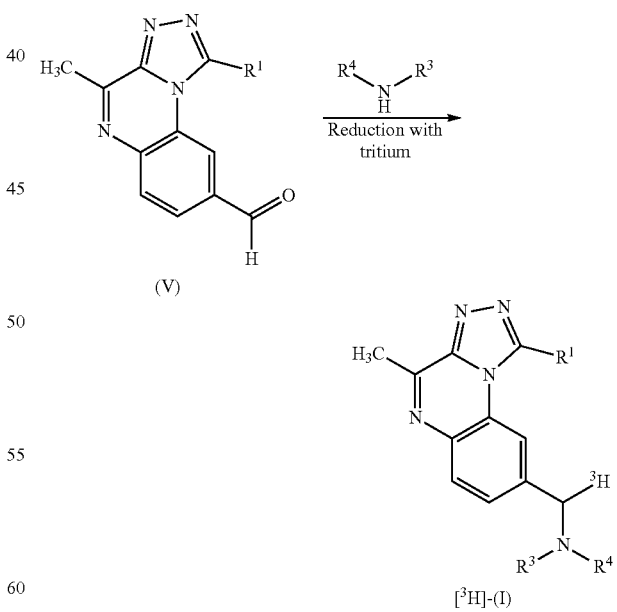

Tritiated compounds of Formula (I), referred to herein as [$^3H$]-(I) may be prepared from compounds of formula (V) by reaction with an amine of formula $NHR^3R^4$, wherein $R^3$ and $R^4$ are as previously defined, in a reductive amination reaction using tritium in the presence of a catalyst, under conditions known to the skilled person, in two steps. Thus, a compound of formula (V) can react in a first step with an amine of formula NHR³R⁴ as previously defined in an inert solvent, such as for example, dichloromethane, optionally in the presence of a dehydrating agent such as titanium tetra (isopropoxide) stirring the reaction mixture at a suitable temperature, typically at room temperature under an inert atmosphere. After removal of the solvent the second step involves the addition of another inert aprotic solvent, such as for example, tetrahydrofuran, and reacting the intermediate imine in the presence of a reducing agent, such as tritium, and in the presence of a catalyst, such as Pt on carbon. After the addition of the reducing agent the reaction can be stirred at room temperature for the required time to achieve completion of the reaction, typically 60 min at room temperature. This reaction step yields a final compound of Formula [$^3$H]-(I).

Scheme 4: Synthesis of Compounds of Formula (I) where R$^1$=$^8$F-Radiolabelled Phenyl or Pyridinyl

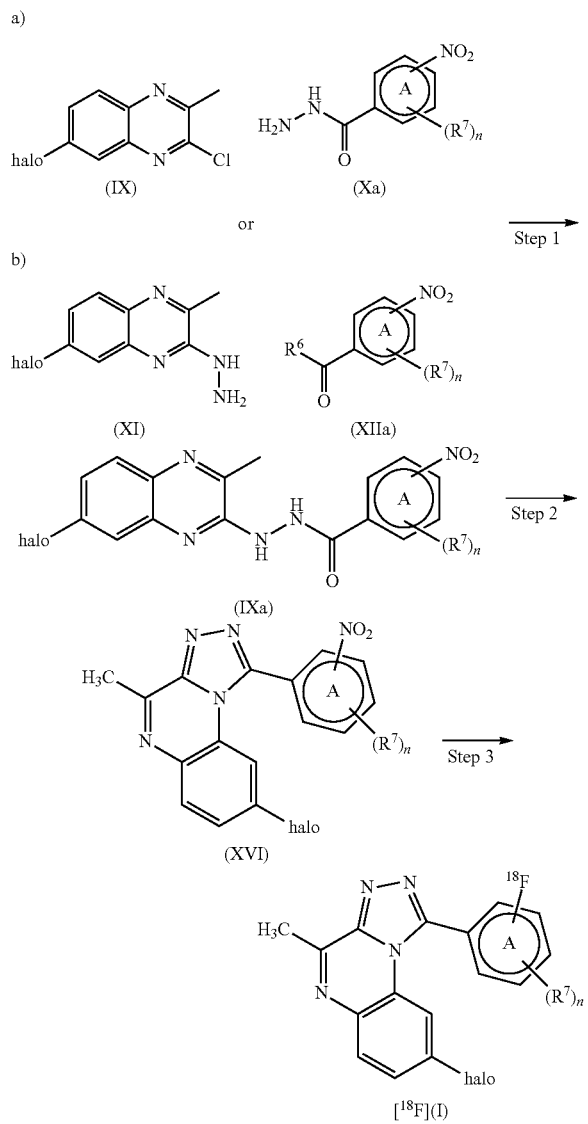

Compounds of formula (I), wherein R$^1$ is a $^{18}$F-radiolabelled phenyl or pyridinyl group, wherein ring A is phenyl or pyridinyl, R$^7$ is halo or trifluoromethyl, n is 0 or 1 and R$^2$ is as previously defined, hereby referred to as a compound of Formula (I-u) can be prepared by synthesis methods well known to the person skilled in the art. For example, by general scheme 10:

Step 1: (a) A compound of Formula (IX) can be reacted with a compound of Formula (Xa) wherein ring A is phenyl or pyridinyl, R$^7$ is halo or trifluoromethyl, n is 0 or 1 and R$^2$ is as previously defined for compounds of Formula (I), according to the conditions described under Scheme 1, Method A, Step 3.

Step 1: (b) A compound of Formula (XI) can be reacted with a compound of formula (XIIa) wherein ring A is phenyl or pyridinyl, R$^7$ is halo or trifluoromethyl, n is 0 or 1 and R$^2$ is as previously defined for compounds of Formula (I), according to the conditions described under Scheme 1, Method B, Step 2.

Step 2: Intermediate compound of Formula (IXa) can react, in presence or absence of a solvent such as for example 1,2-dichloroethane, with phosphorous oxychloride, stirring the reaction mixture at a suitable temperature, typically at 80-100° C., using conventional heating or under microwave irradiation, for the required time to achieve completion of the reaction, typically 16 hours for conventional heating.

Step 3: Intermediate compound of Formula (XVI) can undergo a nucleophilic aromatic substitution reaction with a source of [$^{18}$F]fluoride ([$^{18}$F]F$^-$) such as for example [$^{18}$F] F$^-$/K$_2$CO$_3$/Kryptofix® 222 complex, or [$^{18}$F]KF.K$_{222}$ (wherein Kryptofix® 222 and K$_{222}$ mean 4,7,13,16,21,24-hexaoxa-1,10-diazabicyclo[8.8.8]hexacosane; also known as K 2.2.2) in an inert solvent such as for example anhydrous DMF under appropriate reaction conditions, such as heating in a microwave, for example at 140° C. or conditions known to the skilled person (for a review, see for example P. W. Miller et al. Angew. Chem. Int. Ed. 2008, 47, 8998-9033).

Some compounds according to the invention were isolated as acid addition salt forms or isolated as free base and then converted to the acid addition salt forms. In order to obtain the acid addition salt forms of the compounds according to the invention, for example the HCl salt forms unless otherwise described, several procedures known to those skilled in the art can be used. In a typical procedure, for example, the free base can be dissolved in isopropanol, diisopropylether, diethyl ether and/or dichloromethane and subsequently, 1 to 2 equivalents of the appropriate acid, for example a 6N HCl solution in 2-propanol or a 2N HCl solution in diethyl ether, can be added dropwise. The mixture typically is stirred for 10 min or longer after which the product can be filtered off. The HCl salt is usually dried in vacuo. The values of salt stoichiometry as provided hereinbefore and hereinafter, are those obtained experimentally and may vary when using different analytical methods. When the stoichiometry of the salt is unknown the expression ".x" is used; for example, a hydrochloride salt for which the stoichiometry is unknown is referred to as ".x HCl".

Pharmacology

The compounds of formula (I) and pharmaceutically acceptable salts and solvates thereof according to the invention inhibit PDE2 enzyme activity, in particular PDE2A, and to a lesser extent they inhibit PDE10 enzyme activity, in particular PDE10A, and hence raise the levels of cAMP or cGMP within cells that express PDE2. PDE10 inhibitors can be used to raise levels of cAMP and/or cGMP within cells that express the PDE10 enzyme. It has now been found that PDE2 inhibitors, in particular, the compounds of formula (I), and pharmaceutically acceptable salts and solvates thereof can potentiate the effect of PDE10 inhibitors, in particular, those selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, and one or more PDE10 inhibitor(s) in particular those selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, can dose-dependently potentiate the in vivo binding of a radioligand binding selectively to the catalytic domain of the PDE2 enzyme. In view of the above-mentioned activity and observed effects, it is envisioned that the combinations comprising a PDE2 inhibitor, in particular, a compound of formula (I) as described herein and one or more PDE10 inhibitor(s), in particular those selected from the group of MP-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as described herein or pharmaceutical compositions comprising said combinations, may be useful in the treatment of neurological or psychiatric disorders, or endocrinological or metabolic disorders.

Hence, the present invention relates to a combination of a PDE2 inhibitor, in particular a compound of formula (I), or a pharmaceutically acceptable salt or a solvate thereof and one or more PDE10 inhibitor(s), in particular those selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the present invention, for use as a medicine, as well as to the use of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention or a pharmaceutical composition according to the invention for the manufacture of a medicament. The present invention also relates to a PDE2 inhibitor, in particular a compound of formula (I) or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the present invention or a pharmaceutical composition according to the invention for use in the treatment or prevention of, in particular treatment of, a condition in a mammal, including a human, wherein the condition is selected from neurological or psychiatric disorders, or endocrinological or metabolic disorders. The present invention also relates to the use of a PDE2 inhibitor, in particular a compound of formula (I) or a pharmaceutically acceptable salt or a solvate thereof and one or more PDE10 inhibitors, in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the present invention or a pharmaceutical composition according to the invention for the manufacture of a medicament for the treatment or prevention of, in particular treatment of, a condition in a mammal, including a human, wherein the condition is selected from neurological or psychiatric disorders, or endocrinological or metabolic disorders.

The present invention also relates to a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention, or a pharmaceutical composition according to the invention for use in the treatment, prevention, amelioration, control or reduction of the risk of neurological or psychiatric disorders, or endocrinological or metabolic disorders.

Also, the present invention relates to the use of a PDE2 inhibitor, in particular a compound of formula (I) or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention or a pharmaceutical composition according to the invention for the manufacture of a medicament for treating, preventing, ameliorating, controlling or reducing the risk of various neurological or psychiatric disorders, or endocrinological or metabolic disorders.

Where the invention is said to relate to the use of a PDE2 inhibitor, in particular a compound of formula (I) or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, or composition according to the invention for the manufacture of a medicament for e.g. the treatment of a subject, e.g. a mammal, it is understood that such use is to be interpreted in certain jurisdictions as a method of e.g. treatment of a subject, comprising administering to a subject in need of such e.g. treatment, a therapeutically effective amount of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, or composition according to the invention.

In particular, the indications that may be treated with the combinations of a PDE2 inhibitor, in particular a compound of formula (I), or a pharmaceutically acceptable salt or a solvate thereof and one or more PDE10 inhibitor(s) in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; pain; autistic disorder or autism; and metabolic disorders.

In particular, the psychotic disorders and conditions associated with PDE2 or with PDE2 and PDE10 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder; treatment-resistant depression; and substance-induced mood disorder.

In particular, neurodegenerative disorders include Parkinson's disease; Huntington's disease; dementia such as for example Alzheimer's disease; multi-infarct dementia; AIDS-related dementia or fronto temporal dementia. The neurodegenerative disorder or condition comprises dysfunction of striatal medium spiny neurons responses.

In particular, disorders or conditions comprising as a symptom a deficiency in attention and/or cognition, or cognitive disorders, include dementia, such as Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; other diseases include delirium; amnestic disorder; post-traumatic stress disorder; stroke; progressive supranuclear palsy; mental retardation; a learning disorder; attention-deficit/hyperactivity disorder (ADHD); mild cognitive impairment; Asperger's syndrome; and age-related cognitive impairment.

In particular, pain includes acute and chronic states, severe pain, intractable pain, neuropathic pain and post-traumatic pain, cancer pain, non-cancer pain, pain disorder associated with psychological factors, pain disorder associated with a general medical condition or pain disorder associated with both psychological factors and a general medical condition.

In particular, metabolic disorders include diabetes, in particular type 1 or type 2 diabetes, and related disorders such as obesity. Additional related disorders include syndrome X, impaired glucose tolerance, impaired fasting glucose, gestational diabetes, maturity-onset diabetes of the young (MODY), latent autoimmune diabetes adult (LADA), associated diabetic dyslipidemia, hyperglycemia, hyperinsulinemia, dyslipidemia, hypertriglyceridemia, and insulin resistance.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder; treatment-resistant depression; and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by PDE2 inhibitors, in particular the compounds of formula (I), or a salt or a solvate thereof of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; pain; autism; diabetes and obesity.

Preferably, the disorders treated by PDE2 inhibitors, in particular the compounds of formula (I), or a salt or a solvate thereof of the present invention are schizophrenia, including positive and negative symptoms thereof, and cognitive deficits, such as impaired attention or memory.

Of the disorders mentioned above, the treatment of anxiety, obsessive-compulsive disorder, post-traumatic stress disorder; generalized anxiety disorder, schizophrenia, depression, attention-deficit/hyperactivity disorder, Alzheimer's disease, dementia due to Huntington's disease, dementia due to Parkinson's disease, dementia of the Alzheimer's type, substance-induced persisting dementia and mild cognitive impairment are of particular importance.

Of the disorders mentioned above, the treatment of anxiety, obsessive-compulsive disorder, schizophrenia, depression, attention-deficit/hyperactivity disorder, and Alzheimer's disease are of particular importance.

Other central nervous system disorders include schizo-anxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention, for use in the treatment of any one of the diseases mentioned hereinbefore.

The invention also relates to a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention for use in treating any one of the diseases mentioned hereinbefore.

The invention also relates to a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention, for the treatment or prevention, in particular treatment, of any one of the diseases mentioned hereinbefore.

The invention also relates to the use of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention, for the manufacture of a medicament for the treatment or prevention of any one of the disease conditions mentioned hereinbefore.

The invention also relates to the use of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention for the manufacture of a medicament for the treatment of any one of the disease conditions mentioned hereinbefore.

The PDE2 inhibitors, in particular the compounds of formula (I), or a pharmaceutically acceptable salt or a solvate thereof and one or more PDE10 inhibitors in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, of the present invention can be administered to mammals, preferably humans, for the treatment or prevention of any one of the diseases mentioned hereinbefore.

In view of the utility of PDE2 inhibitors, in particular the compounds of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention, there is provided a method of treating a disorder or disease mentioned hereinbefore, comprising administering to a subject in need thereof, a therapeutically effective amount of a PDE2 inhibitor, in particular any of the compounds of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, or a therapeutically effective amount of pharmaceutical compositions described herein.

Said methods comprise the administration, i.e. the systemic or topical administration, preferably oral administration, of a therapeutically effective amount of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention to warm-blooded animals, including humans.

Therefore, the invention also relates to a method for the prevention and/or treatment of any one of the diseases mentioned hereinbefore comprising administering a therapeutically effective amount of a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the invention to a patient in need thereof.

The PDE2 inhibitors, in particular the compounds of formula (I), and pharmaceutically acceptable salts and solvates thereof and PDE10 inhibitors described herein can be in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic a-7 agonists, PDE4 inhibitors, other PDE2 inhibitors, other PDE10 inhibitors, other PDE2 and 10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, and cholinesterase inhibitors (e.g. donepezil, rivastigmine, and galantamine). In such combinations, the PDE2 inhibitors, in particular the compounds of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, of the present invention may be utilized in combination with one or more other drugs in the treatment, prevention, control, amelioration, or reduction of risk of diseases or conditions for which PDE2 inhibitors, in particular compounds of Formula (I), and pharmaceutically acceptable salts and solvates thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, or the other drugs may have utility, where the combination of the drugs together are safer or more effective than either drug alone.

One skilled in the art will recognize that a therapeutically effective amount of the PDE2 inhibitors, in particular the compounds of formula (I), and pharmaceutically acceptable salts and solvates thereof and of one or more PDE10 inhibitor(s) of the present invention is the amount sufficient to inhibit the PDE2 enzyme or both PDE2 and PDE10 enzymes and that this amount varies inter alia, depending on the type of disease, the concentration of the compound in the therapeutic formulation, and the condition of the patient. Generally, an amount of PDE2 inhibitor, in particular of compound of formula (I), or pharmaceutically acceptable salt or solvate thereof and one or more PDE10 inhibitor(s) according the invention, to be administered as a therapeutic agent for treating conditions such as the disorders described herein, will be determined on a case by case by an attending physician.

Generally, a suitable dose is one that results in a concentration of the PDE2 inhibitor, in particular of the compound of formula (I) or pharmaceutically acceptable salt or solvate thereof and one or more PDE10 inhibitor(s) according to the invention at the treatment site in the range of 0.5 nM to 200 µM, and more usually 5 nM to 50 µM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a PDE2 inhibitor, in particular of a compound of formula (I), or a pharmaceutically acceptable salt or a solvate thereof and of one or more PDE10 inhibitor(s) according to the present invention, also referred to here as the active ingredients, which is required to achieve a therapeutical effect will, of course vary on case-by-case basis, vary with the particular compound, the route of administration, the age and condition of the recipient, and the particular disorder or disease being treated. A method of treatment may also include administering the active ingredients on a regimen of between one and four intakes per day. In these methods of treatment the PDE2 inhibitors, in particular the compounds of formula (I), and the pharmaceutically acceptable salts and the solvates thereof and the one or more PDE10 inhibitor(s) according to the invention are preferably formulated prior to admission. As described herein below, suitable pharmaceutical formulations are prepared by known procedures using well known and readily available ingredients.

Pharmaceutical Compositions

The present invention also provides compositions for preventing or treating diseases such as neurological and psychiatric disorders, and endocrinological or metabolic diseases. Said compositions comprising a therapeutically effective amount of a PDE2 inhibitor, in particular of a compound according to formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, and a pharmaceutically acceptable carrier or diluent.

While it is possible for the active ingredients to be administered alone, it is preferable to present them as a pharmaceutical composition. Accordingly, the present invention further provides a pharmaceutical composition comprising a PDE2 inhibitor, in particular a compound of formula (I), or a pharmaceutically acceptable salt or a solvate thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compounds, in base form or addition salt form, as the active ingredients is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Depending on the mode of administration, the pharmaceutical composition will comprise from 0.05 to 99% by weight, preferably from 0.1 to 70% by weight, more preferably from 0.1 to 50% by weight of the active ingredients, and, from 1 to 99.95% by weight, preferably from 30 to 99.9% by weight, more preferably from 50 to 99.9% by weight of a pharmaceutically acceptable carrier, all percentages being based on the total weight of the composition.

The present combinations of compounds can be used for systemic administration such as oral, percutaneous or parenteral administration; or topical administration such as via inhalation, a nose spray, eye drops or via a cream, gel, shampoo or the like. The compounds are preferably orally administered.

The exact dosage and frequency of administration depends on the particular PDE2 inhibitor, such as the compound according to formula (I), or pharmaceutically acceptable salt or solvate thereof and the one or more PDE10 inhibitor(s) selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the PDE2 inhibitors, in particular the compounds of formula (I), and pharmaceutically acceptable salts and solvates thereof and one or more PDE10 inhibitor(s), in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, of the instant invention.

The amount of PDE2 inhibitor, in particular of a compound of Formula (I), or pharmaceutically acceptable salt or solvate thereof and one or more PDE10 inhibitor(s) in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, that can be combined with a carrier material to produce a single dosage form will vary depending upon the disease treated, the mammalian species, and the particular mode of administration. However, as a general guide, suitable unit doses for the PDE2 inhibitors, in particular the compounds of formula (I), and pharmaceutically acceptable salts and solvates thereof and one or more PDE10 inhibitor(s) in particular selected from the group of MP-10, PQ-10, TP-10, papaverine, a compound of Formula (II) or a stereoisomeric form thereof or a pharmaceutically acceptable salt or a solvate thereof as defined herein, and a compound of Formula (III) or a stereoisomeric form thereof or a pharmaceutically acceptable salt or a solvate thereof as defined herein, of the present invention can, for example, preferably contain between 0.1 mg to about 1000 mg of the active compounds. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compounds employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredients. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXPERIMENTAL PART

I. Chemistry

As used herein, the term "LCMS" means liquid chromatography/mass spectrometry, "GCMS" means gas chromatography/mass spectrometry, "HPLC" means high-performance liquid chromatography, "RP HPLC" means reverse phase high-performance liquid chromatography, "aq." means aqueous, "Boc" means tert-butoxycarbonyl, "nBuLi" means n-butyllithium, "BuOH" means 1-butanol, "DCE" means 1,2-dichloroethane, "DCM" means dichloromethane, "DIPE" means diisopropyl ether, "DIPEA" means diisopropylethyl amine, "DMF" means N,N-dimethylformamide, "EtOH" means ethanol, "EtOAc" means ethyl acetate, "Et$_3$N" means triethylamine, "Pd(AcO)$_2$" means palladium (II) acetate, "XantPhos" means 4,5-bis(diphenyl-phosphino)-9,9-dimethylxanthene, "Pd—C" means Palladium on carbon, "THF" means tetrahydrofuran, "min" means minutes, "h" means hours, "MeOH" means methanol, "iPrOH" means 2-propanol, "r.m." means reaction mixture, "r.t." means room temperature, "R$_t$" means retention time (in minutes), "Tf" means trifluoromethanesulfonate, "TFA" means trifluoroacetic acid, "quant." means quantitative, "sat." means saturated, "sol." means solution, "[M+H]$^+$" means the protonated mass of the free base of the compound, "[M-H]$^-$" means the deprotonated mass of the free base of the compound, 'm.p." means melting point, "q.s." means quantum sufficit.

Microwave assisted reactions were performed in a single-mode reactor: Biotage Initiator™ Sixty microwave reactor (Biotage) or in a multimode reactor: MicroSYNTH Labstation (Milestone, Inc.).

Hydrogenation reactions were performed in a continuous flow hydrogenator H-CUBE® from ThalesNano Nanotechnology Inc.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques. Automated flash column chromatography was performed using ready-to-connect cartridges from Merck, on irregular silica gel, particle size 15-40 μm (normal phase disposable flash columns) on an SPOT or LAFLASH system from Armen Instrument.

Several methods for preparing the compounds of this invention are illustrated in the following examples, which are intended to illustrate but not to limit the scope of the present invention. Unless otherwise noted, all starting materials were obtained from commercial suppliers and used without further purification.

A. Synthesis of Intermediates and Precursors

Intermediates 1-a and 1-b ((I-1a) and (I-1b))

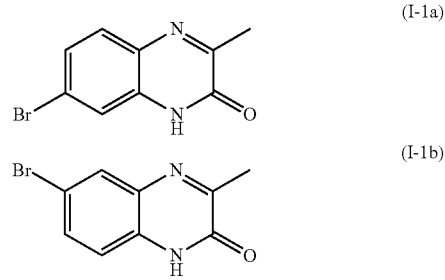

Methyl pyruvate (8.69 mL, 96.24 mmol) was added to a solution of 4-bromo-1,2-diaminobenzene (15 g, 80 mmol) dissolved in toluene (120 mL) in a round flask, equipped with a Dean-Stark apparatus. Then the r.m. was heated under reflux for 3 h. When the reaction was finished, the solvent was removed in vacuo and the crude product was washed with diethyl ether to give a mixture of intermediates (I-1a) and (I-1b) as a pale gray solid that was used as such in the next step (16 g, 83%). C$_9$H$_7$BrN$_2$O, LCMS: Rt 1.07 (first isomer), 1.15 (second isomer), m/z 239 [M+H]$^+$ (method 2).

A batch of the regioisomeric mixture was separated by suspending the mixture in methanol and ammonium hydroxide (q.s.), warming up to reflux and cooling down to room temperature. The precipitate that formed was filtered, water was added to the filtrate and the precipitate that formed was also recovered by filtration. Two additional cycles were repeated to obtain a precipitate containing a 94:6 mixture of I-1a:I-1b.

Intermediates 2-a and 2-b ((I-2a) and (I-2b))

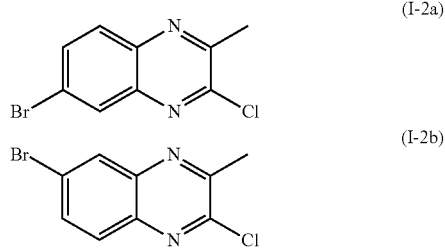

The mixture of intermediates (I-1a) and (I-1b) (16 g, 66.95 mmol) was dissolved in POCl$_3$ (78 mL), and the r.m. was stirred for 2 h at 120° C. The solvent was then evaporated and the mixture was cooled down in an ice bath and gently NH$_4$OH was added dropwise until it reached a basic pH. Once the addition was completed, the formed precipitate was filtered off, washed with H$_2$O and then washed several times with DCM. The organic solvent was dried (Na$_2$SO$_4$), filtered, and concentrated in vacuo. The crude product was purified by open column chromatography (silica, DCM in heptane 20/80 to 80/20), the desired fractions were collected and concentrated in vacuo to give a mixture of intermediates (I-2a) and (I-2b) as white solid (12 g, 69%). C$_9$H$_6$BrClN$_2$, LCMS: Rt 2.95 (co-elution of the two peaks), m/z 257 [M+H]$^+$ (method 8).

Intermediate 3 (I-3)

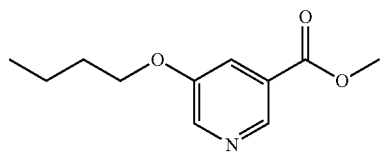

To a stirred solution of 5-hydroxynicotinic acid methyl ester (0.8 g, 5.22 mmol) and di-tert-butylazadicarboxylate (1.8 g, 7.83 mmol) in THF (6 mL), triphenylphosphine (2.05 g, 7.83 mmol) was added portionwise at r.t. The mixture was stirred at this temperature for 5 min and then BuOH (2 mL) was added and the stirring was continued at r.t. for 30 min. Then the solvent was evaporated and the crude compound purified by chromatography (silica, EtOAc in heptane 0/100 to 20/80) the desired fractions were collected and evaporated in vacuo to give intermediate I-3 as colorless oil (0.55 g, 50.3%). C$_{11}$H$_{15}$NO$_3$, LCMS: Rt 2.71, m/z 210 [M+H]$^+$ (method 5).

Intermediate 4 (I-4)

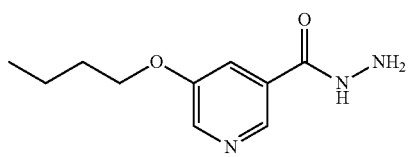

Hydrazine hydrate (60% in H$_2$O, 0.216 mL, 2.86 mmol) was added dropwise to a stirred solution of intermediate I-3 (0.5 g, 2.39 mmol) in MeOH (4 mL) at r.t. and the mixture was stirred at this temperature for 72 h. The solvent was then evaporated in vacuo to give intermediate I-4 as white solid (0.48 g, 96%) that was used as such in the next reaction step. C$_{10}$H$_{15}$N3O$_2$, LCMS: Rt 1.86, m/z 210 [M+H]$^+$ (method 8).

Intermediate 5 (I-5)

8-Bromo-1-(5-butoxypyridin-3-yl)-4-methyl[1,2,4]triazolo[4,3-a]quinoxaline (I-5)

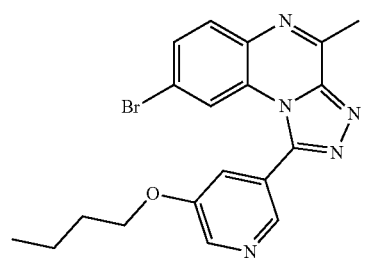 [SMILES: CCCCOc1cncc(-c2nnc3c(C)nc4ccc(Br)cc4n23)c1]

To a solution of intermediate I-2a (5 g, 19.4 mmol) in BuOH (40 ml) intermediate I-4 (4.06 g, 19.4 mmol) was added. The r.m. was heated in a sealed reactor at 160° C. for 30 min. The mixture was then evaporated till dryness and the residue taken up in EtOAc. The organic layer was washed with NaHCO$_3$ (sat. sol.), then separated, dried (MgSO$_4$), filtered and the solvent evaporated in vacuo. The crude mixture was purified by chromatography (silica, EtOAc in DCM 5/95 to 25/75), the desired fractions were collected and evaporated, and the solid compound obtained was further triturated with heptane to give intermediate I-5 (3.3 g, 41%). $^1$H NMR (300 MHz, DMSO-d$_6$) δ ppm 0.93 (t, J=7.4 Hz, 3H), 1.45 (sxt, J=7.5 Hz, 2H), 1.75 (quin, J=6.3 Hz, 2H), 2.92 (s, 3H), 4.13 (t, J=6.3 Hz, 2H), 7.48 (d, J=1.6 Hz, 1H), 7.82 (dd, J=8.7, 1.8 Hz, 1H), 7.91 (br. s., 1H), 7.99 (d, J=8.7 Hz, 1H), 8.55 (br. s, 1H), 8.65 (d, J=2.6 Hz, 1H).

Intermediate 6 (I-6)

8-Bromo-1-(2-chlorophenyl)-4-methyl[1,2,4]triazolo[4,3-a]quinoxaline (I-6a) and 7-Bromo-1-(2-chlorophenyl)-4-methyl[1,2,4]triazolo[4,3-a]quinoxaline (I-6b)

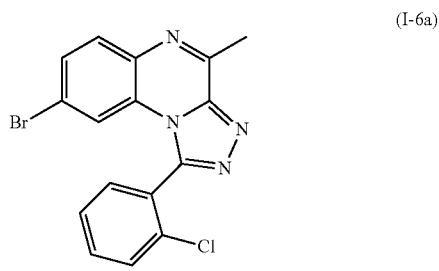

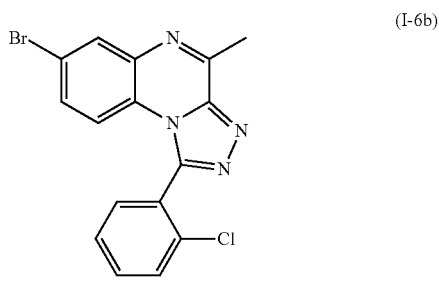

A mixture of intermediates I-2a and I-2b (0.3 g, 1.16 mmol), and 2-chlorobenzoic hydrazide ([CAS 5814-05-1], 238.97 mg, 1.40 mmol) was dissolved in EtOH (5 mL). The reaction mixture was heated in a microwave oven at 160° C. for 15 min, then heated again at 170° C. for 10 min. Then the solvent was evaporated till dryness and the residue taken up in DCM. The organic layer was washed with K$_2$CO$_3$ (sat. sol.), then dried over Na$_2$SO$_4$ and evaporated under vacuum. The crude compound was purified by chromatography (SiO$_2$, 30 g, CH$_2$Cl$_2$:EtOAc from 100:0 to 85:15) to give intermediate compound I-6a (0.13 g, 29.8%) and intermediate compound I-6b (0.11 g, 25.2%) which were obtained as pure isomers (both as solid compounds). $^1$H NMR (500 MHz, CDCl$_3$) δ ppm 3.07 (s, 3H), 7.32 (d, J=2.0 Hz, 1H), 7.56-7.62 (m, 1H), 7.65-7.72 (m, 4H), 7.92 (d, J=8.7 Hz, 1H) (for I-6a). $^1$H NMR (500 MHz, CDCl$_3$) δ ppm 3.09 (s, 3H), 7.10 (d, J=9.0 Hz, 1H), 7.46 (dd, J=9.0, 2.3 Hz, 1H), 7.54-7.58 (m, 1H), 7.63-7.71 (m, 3H), 8.22 (d, J=2.0 Hz, 1H) (for I-6b).

Intermediate 7 (I-7)

1-(2-Chlorophenyl)-8-ethenyl-4-methyl[1,2,4]triazolo[4,3-a]quinoxaline (I-7)

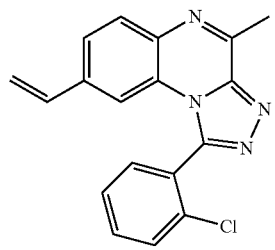 [SMILES: C=Cc1ccc2nc(C)c3nnc(-c4ccccc4Cl)n3c2c1]

A mixture of intermediate compound I-6a (0.65 g, 1.74), (tetrakis)triphenylphosphine palladium(0) (0.080 g, 0.07 mmol) and LiCl (0.221 g, 5.21 mmol) in toluene (30 mL) was treated with tributylvinyl tin (0.661 g, 2.088 mmol) and heated in a sealed tube at 120° C. for 1 h (the reaction was divided in two batches). After cooling to r.t. the mixture was partitioned between EtOAc and H$_2$O. The organic phase was washed with brine, separated, dried (Na$_2$SO$_4$), filtered, and the solvent concentrated in vacuo. The crude compound was purified by chromatography (silica EtOAc in DCM 10/90 to 50/50) giving a light yellow solid that was further washed with DIPE/diethyl ether to yield intermediate compound I-7 as white product (0.52 g, 93.1%). $^1$H NMR (400 MHz, CDCl$_3$) δ ppm 3.08 (s, 3H), 5.25 (d, J=10.9 Hz, 1H), 5.43 (d, J=17.6 Hz, 1H), 6.53 (dd, J=17.5, 11.0 Hz, 1H), 7.24 (d, J=1.6 Hz, 1H), 7.54-7.62 (m, 2H), 7.64-7.74 (m, 3H), 7.99 (d, J=8.3 Hz, 1H).

Intermediate 8 (I-8)

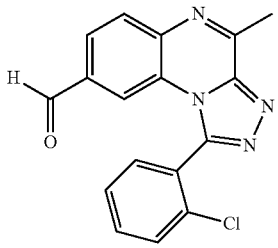 [SMILES: Cc1nc2ccc(C=O)cc2n2c(-c3ccccc3Cl)nnc12]

To a mixture of intermediate compound I-7 (3.3 g, 10.29 mmol) in 1,4-dioxane (110 mL), osmium tetraoxide (2.5% in t-BuOH, 5.33 mL, 0.411 mmol) and then sodium periodate (6.6 g, 30.86 mmol) in H$_2$O (30 mL) were added. The mixture was stirred at r.t. for 2 h. The organic solvent was evaporated, the crude mixture diluted with more H$_2$O and extracted with DCM. The organic layer was dried (Na$_2$SO$_4$), filtered and the solvent concentrated in vacuo. The crude product was purified by chromatography (Silica, EtOAC in DCM 30/70 to 70/30), the desired fractions were collected and concentrated in vacuo. The solid obtained was washed with diethylether to yield intermediate I-8 (2.5 g, 75%) as pale yellow solid. C$_{17}$H$_{11}$ClN$_4$O, LCMS: 1.78, m/z 323 [M+H]$^+$ (method 3).

Intermediate 9 (I-9)

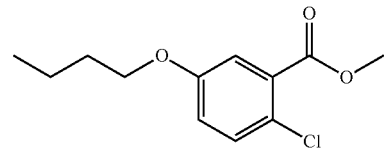 [SMILES: CCCCOc1ccc(Cl)c(C(=O)OC)c1]

Sodium hydride (60% in mineral oil, 0.16 g, 4.02 mmol) was added at r.t. to a stirred solution of methyl 2-chloro-5-hydroxybenzoate [(C.A.S. 247092-10-0), 0.5 g, 2.68 mmol] dissolved in THF (4 mL). The mixture was stirred at this temperature for 15 min and then bromobutane (0.575 mL, 5.36 mmol) was added. The stirring was continued at the same temperature overnight and then the r.m. was heated at 120° C. for 40 min under microwave irradiation. The mixture was then quenched with H$_2$O and extracted with EtOAc, the organic layer was separated, dried (Na$_2$SO$_4$), filtered and concentrated in vacuo to give intermediate I-9 (0.25 g, 38.4%) as orange oil that was used as such in the next reaction step. C$_{12}$H$_{15}$ClO$_3$, GCMS: 5.78, m/z 242 [M$^+$] (method 1).

Intermediate 10 (I-10)

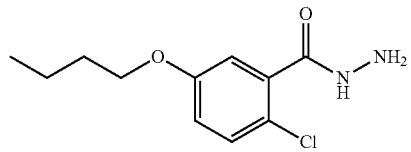 [SMILES: CCCCOc1ccc(Cl)c(C(=O)NN)c1]

Hydrazine hydrate (65% in H$_2$O, 0.118 g, 1.54 mmol) was added dropwise to a stirred solution of intermediate I-9 (0.25 g, 1.03 mmol) in EtOH (2 mL) at r.t. and the mixture was stirred at 120° C. for 20 min under microwave irradiation. Then the solvent was evaporated under vacuum to give intermediate I-10 around 70% pure (0.32 g, 89.5%) as white solid, which was used as such in the next reaction step. C$_{11}$H$_{15}$ClN$_2$O$_2$, LCMS: Rt 2.34, m/z 243 [M+H]$^+$ (method 8).

Intermediate 11-a and 11-b (I-11a) and (I-11b)

8-Bromo-1-(5-butoxy-2-chlorophenyl)-4-methyl[1,2,4]triazolo[4,3-a]quinoxaline (I-11a) and 7-Bromo-1-(5-butoxy-2-chlorophenyl)-4-methyl[1,2,4]triazolo[4,3-a]quinoxaline (I-11b)

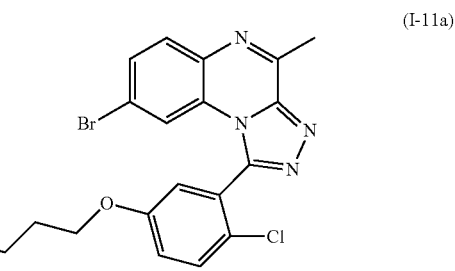
(I-11a)

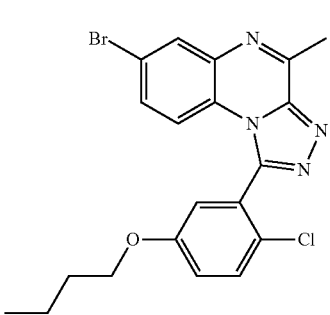

(I-11b)

Intermediate compounds I-11a and I-11b were synthesized following the same procedure described for the synthesis of Intermediates I-6a and I-6b. Starting from a mixture of intermediates I-2a and I-2b (0.2 g, 0.77 mmol) and intermediate I-10, intermediate compound I-11a (0.05 g, 14.4%) and intermediate compound I-11b (0.075 g, 21.6%) as pure isomers (both as off-white solids) were obtained. $^1$H NMR (500 MHz, CDCl$_3$) δ ppm 0.98 (t, J=7.4 Hz, 3H), 1.50 (sxt, J=7.5 Hz, 2H), 1.76-1.84 (m, 2H), 3.06 (s, 3H), 3.93-4.10 (m, 2H), 7.16-7.21 (m, 2H), 7.44 (d, J=1.7 Hz, 1H), 7.50-7.58 (m, 1H), 7.68 (dd, J=8.7, 2.0 Hz, 1H), 7.91 (d, J=8.7 Hz, 1H) (for I-11a). $^1$H NMR (500 MHz, CDCl$_3$) δ ppm 0.97 (t, J=7.4 Hz, 3H), 1.49 (sxt, J=7.5 Hz, 2H), 1.74-1.84 (m, 2H), 3.08 (s, 3H), 3.93-4.08 (m, 2H), 7.14-7.21 (m, 3H), 7.45-7.54 (m, 2H), 8.22 (d, J=2.0 Hz, 1H) (for I-11b).

Intermediate 12 (I-12)

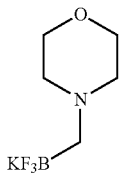

To a solution of morpholine (0.876 mL, 9.96 mmol) in CH$_3$CN (12 mL) potassium (bromomethyl)trifluoroborate (1 g, 4.97 mmol) was added and then the r.m. was heated at 80° C. for 30 min. Then the solvent was evaporated under vacuum and the crude material re-dissolved in a solution of KHCO$_3$ (0.5 g, 4.97 mmol) in dry acetone (16 mL). The mixture was further stirred at r.t. for 20 min. Then the insoluble salts were filtered off, and the solvent concentrated again. The crude material was finally purified by dissolving it in a minimal amount of dry acetone and precipitating it with diethylether to obtain intermediate I-12 as pure product (0.66 g, 64%).

Intermediate 13-a and 13-b (I-13a) and (I-13b)

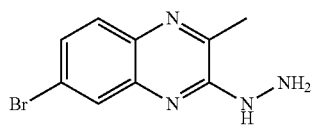

(I-13a)

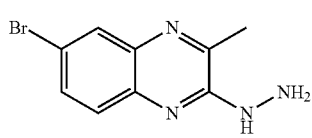

(I-13b)

Hydrazine hydrate (60% in H$_2$O, 0.52 mL, 9.7 mmol) was added to a mixture of Intermediate (I-2a) and Intermediate (I-2b) (1 g, 3.88 mmol) in MeOH (15 mL) at r.t. The r.m. was then heated at 50° C. for 30 min, after that it was diluted with H$_2$O (5 mL) and extracted with DCM (20 mL). The organic layers were separated, dried (MgSO4), filtered and concentrated in vacuo to give a mixture of intermediates (I-13a) and (I-13b) (0.92 g, 96%) that was used as such in the next reaction step. C$_9$H$_9$BrN$_4$, LCMS: 4.29 (co-elution of the two peaks), m/z 253 [M+H]$^+$ (method 7).

Intermediate 14-a and 14-b (I-14a) and (I-14)

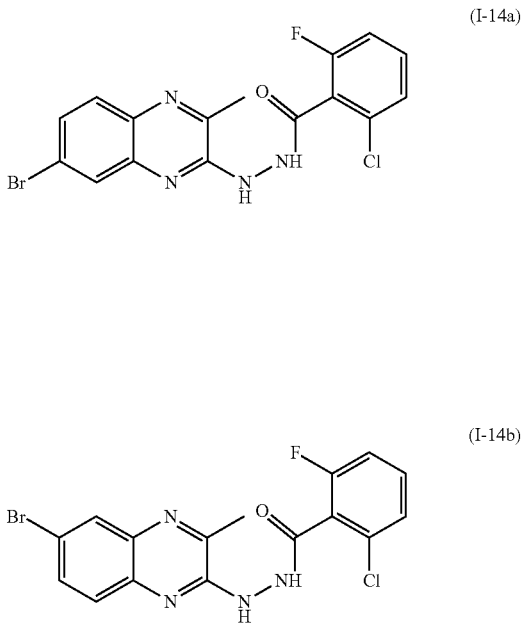

2-Chloro-6-fluorobenzoic acid (0.698 g, 4 mmol) in DMF (20 mL) and DIPEA (1.072 mL, 6.22 mmol) was treated with HBTU (1.52 g, 4 mmol) and the r.m. was stirred for 15 min at r.t. Then a mixture of intermediates (I-13a) and (I-13b) (0.9 g, 3.56 mmol) in DMF (20 mL) was added and the stirring was prolonged for further 16 h at the same temperature. The r.m. was then poured onto ice/H$_2$O (0.5 L) and the solid thus obtained was collected by filtration. The solid was then diluted with DCM (0.1 L) and treated with 1 M NaOH aq. solution (20 mL). The organic layers were separated, washed with IM HCl (20 mL), then with IM NaOH (20 mL), dried (MgSO4), filtered and the solvent concentrated in vacuo. The crude mixture was purified by column chromatography (silica; MeOH in DCM 0:100 to 5:95) to give an off white solid which was recrystallized from Heptane/EtOAc (~15 mL/~5 mL) yielding finally a mixture of intermediates (I-14a) and (I-14b) as off white solid (0.75 g, 51%). C$_{16}$H$_{11}$BrClFN$_4$O, LCMS: 5.18 (co-elution of the two peaks), m/z 409 [M+H]$^+$ (method 7).

Intermediate 15-a and 15b (I-15a) and (I-15b)

8-Bromo-1-(2-chloro-6-fluorophenyl)-4-methyl[1,2,4]triazolo[4,3-a]quinoxaline

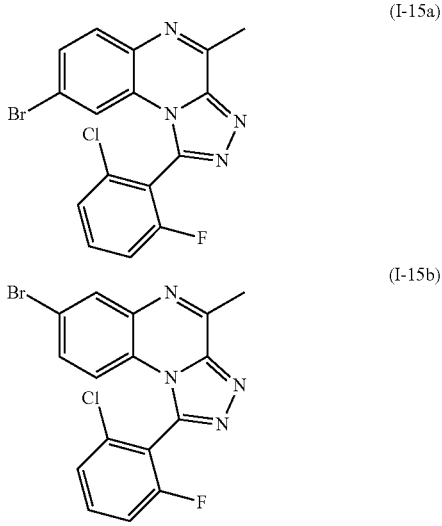

(I-15a)

(I-15b)

A mixture of intermediates (I-14a) and (I-14b) (1 g, 2.44 mmol) in DCE (20 mL) was treated with POCl$_3$ (0.6 mL, 6.5 mmol) and the r.m. was heated at 70° C. for 16 h. Then, additional POCl$_3$ (0.6 mL, 6.5 mmol) was added and the mixture heated at the same temperature as before further for 5 h. After this time, again more POCl$_3$ (1.2 mL, 13 mmol) was added and the mixture heated as before for further 16 h. The r.m. was cooled and poured onto ice/aq. NH$_4$OH (150 mL/150 mL) and the layers separated. The organic phase was dried (MgSO$_4$), filtered and concentrated in vacuo. The crude compound was purified by chromatography (silica; MeOH in DCM 0/100 to 2/98) to give a mixture of intermediate (I-15a) together with its regioisomer (I-15b) (0.7 g, 75%).

A batch of the regioisomeric mixture was separated by column chromatography (silica, EtOAC in CH$_2$Cl$_2$, 0/100 to 25/75) to give intermediate (I-15a) as pure isomer. C$_{16}$H$_9$BrClFN$_4$, LCMS: 2.58, m/z 391 [M+H]$^+$ (method 3).

Intermediate 16 (I-16)

1-(2-Chloro-6-fluorophenyl)-8-ethenyl-4-methyl[1,2,4]triazolo[4,3-a]quinoxaline (I-16)

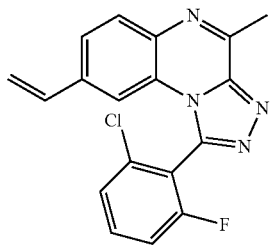 [SMILES: C=Cc1ccc2nc(C)c3nnc(-c4c(F)cccc4Cl)n3c2c1]

Tributylvinyl tin (0.18 mL, 0.61 mmol) was added to a stirred solution of intermediate (I-15a) (0.2 g, 0.511 mmol), LiCl (0.065 g, 1.53 mmol) and (tetrakis)triphenylphosphine palladium(0) (0.023 g, 0.02 mmol) in toluene (7 mL). The mixture was heated at 120° C. for 1.5 h. After cooling to r.t. the r.m. was partitioned between EtOAc and H$_2$O. The organic layer was washed with brine, separated, dried (Na$_2$SO$_4$) and concentrated in vacuo. The crude product was purified by chromatography (silica, EtOAc in DCM 10/90 to 50/50), the desired fractions were collected and concentrated in vacuo, to yield intermediate compound (I-16) as pale yellow solid (0.14 g, 81%). C$_{18}$H$_{12}$ClFN$_4$, LCMS: 2.46, m/z 339 [M+H]$^+$ (method 3).

Intermediate 17 (I-17)

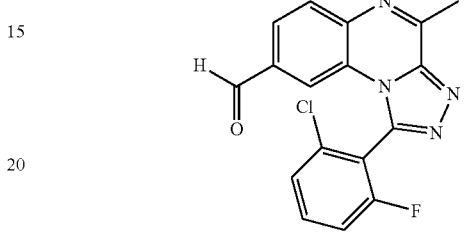

To a solution of intermediate (I-16) (0.14 g, 0.413 mmol) in 1,4-dioxane (5 mL), osmium tetraoxide (2.5% in t-BuOH, 0.214 mL, 0.016 mmol) and then sodium periodate (0.265 g, 1.24 mmol) in H$_2$O (3 mL), were added. The mixture was stirred at r.t. for 2.5 h. The organic solvent was evaporated, the crude mixture diluted with more H$_2$O and extracted with DCM. The organic layer was separated, dried (Na$_2$SO$_4$) and concentrated in vacuo. The crude product was purified by chromatography (Silica, EtOAc in DCM 30/70 to 70/30), the desired fractions were collected and concentrated in vacuo yielding intermediate (I-17) as pale yellow solid (0.1 g, 71%). C$_{17}$H$_{10}$ClFN$_4$O, LCMS: 1.82, m/z 341 [M+H]$^+$ (method 3).

Intermediate 18 (I-18)

1-(5-Butoxypyridin-3-yl)-8-ethenyl-4-methyl[1,2,4]triazolo[4,3-a]quinoxaline (I-18)

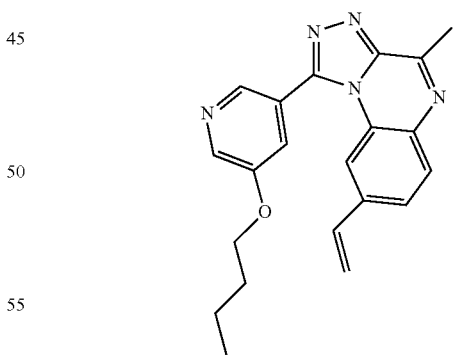

To a stirred solution of I-5 (2.35 g, 5.7 mmol) in toluene (17 mL), were added LiCl (0.719 g, 17.1 mmol), (tetrakis)triphenylphosphine palladium(0) (0.263 g, 0.23 mmol) and tributylvinyl tin (1.84 mL, 6.27 mmol) and the mixture was heated at 120° C. for 2 h. After cooling to r.t. the r.m. was partitioned between EtOAc and H$_2$O. The organic layer was washed with brine, separated, dried (Na$_2$SO$_4$) and concentrated in vacuo. The crude product was purified by chromatography (silica, EtOAc in heptane 0/100 to 100/0), the desired fractions were collected and concentrated in vacuo, to yield intermediate 18 (I-18) (1.9 g, 92%).

Intermediate 19 (I-19)

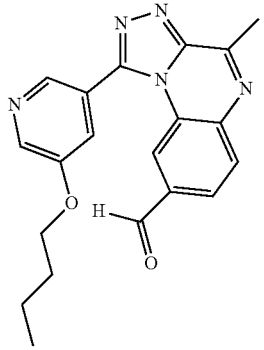 [SMILES: CCCCOc1cncc(-c2nnc3c(C)nc4ccc(C=O)cc4n23)c1]

To a solution of intermediate I-18 (0.159 g, 0.44 mmol) in 1,4-dioxane (4.4 mL), osmium tetraoxide (2.5% in t-BuOH, 0.23 mL, 0.018 mmol) and then sodium periodate (0.282 g, 1.32 mmol) in H$_2$O (1.32 mL), were added. The mixture was stirred at r.t. for 2 h. The organic solvent was evaporated, the crude mixture diluted with more H$_2$O and extracted with DCM. The organic layer was separated, dried (Na$_2$SO$_4$) and concentrated in vacuo. The crude product was purified by chromatography (silica, EtOAc in DCM 0/1 to 1/1), the desired fractions were collected and concentrated in vacuo yielding intermediate (I-19) (0.108 g, 68%).

Intermediate 20 (I-20)

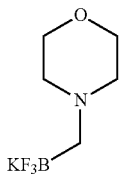

To a solution of morpholine (0.876 mL, 9.96 mmol) in CH$_3$CN (12 mL) potassium (bromomethyl)trifluoroborate (1 g, 4.97 mmol) was added and then the r.m. was heated at 80° C. for 30 min. Then the solvent was evaporated under vacuum and the crude material re-dissolved in a solution of KHCO$_3$ (0.5 g, 4.97 mmol) in dry acetone (16 mL). The mixture was further stirred at r.t. for 20 min. Then the insoluble salts were filtered off, and the solvent concentrated again. The crude material was finally purified by dissolving it in a minimal amount of dry acetone and precipitating it with diethylether to obtain intermediate I-20 as pure product (0.66 g, 64%).

Intermediates 21a and 21b (I-21a) and (I-21b)

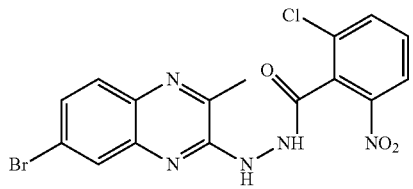

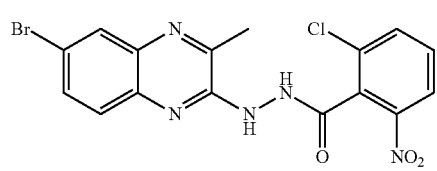

DMF (0.182 mL, 2.34 mmol) was added to a mixture of 2-chloro-6-nitrobenzoic acid (0.473 g, 2.34 mmol) and oxalyl chloride (0.201 mL, 2.34 mmol) in dichloromethane (5 mL). The mixture was stirred for 15 min at RT, then this solution was added dropwise to a stirred mixture of triethylamine (0.544 mL, 1.95 mmol) and intermediate compounds I-13a and I-13b (0.495 g, 1.95 mmol) dissolved in dichloromethane (5 mL) at 0° C. The mixture was then allowed to RT and stirred for further 15 min. Then it was quenched with NaHCO$_3$ (sat. sol. in water), the organic layer was quickly separated and the solvent evaporated. The residue was treated with ethyl ether to yield a mixture of (I-21a) and (I-21b) as a brown solid (0.814 g, 95%) that was used as such in the next reaction step.

Intermediates 22a and 22b (I-22a) and (I-22b)

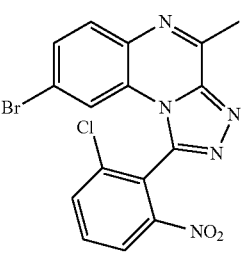

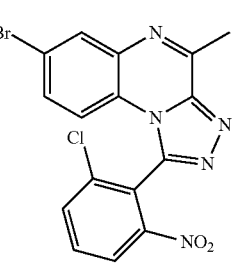

A mixture of intermediate compounds I-21a and I-21b (0.402 g, 0.92 mmol) in DCE (5 mL) was treated with POCl$_3$ (0.343 mL, 3.68 mmol) and the r.m. was heated at 160° C. for 10 min under microwave irradiation. The solvent was then evaporated and the crude compound purified by chromatography (silica, EtOAc in heptanes 20/80 to 60/40). The desired fractions were collected, the solvent evaporated under vacuum to give I-22a (0.053 g, 13.7%) and I-22b (0.112 g, 29%) as pure isomers.

Intermediate 23 (I-23)

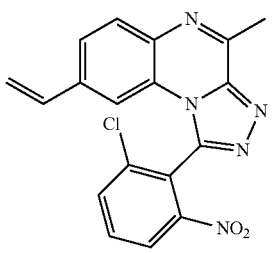 [SMILES: C=Cc1ccc2nc(C)c3nnc(-c4c(Cl)cccc4[N+](=O)[O-])n3c2c1]

Intermediate I-23 was synthesized following a similar approach described for compound I-7. Starting from I-22a (0.053 g, 0.127 mmol) intermediate I-23 was obtained as pale yellow solid (0.046 g, quant.).

Intermediate 24 (I-24)

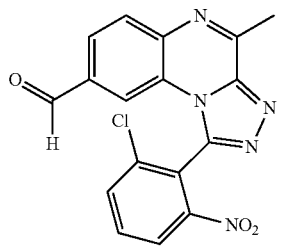 [SMILES: Cc1nc2ccc(C=O)cc2n2c(-c3c(Cl)cccc3[N+](=O)[O-])nnc12]

Intermediate I-24 was synthesized following a similar approach described for intermediate I-8. Starting from I-23 (0.046 g, 0.127 mmol) intermediate I-24 was obtained as pale yellow solid (0.031 g, 66.5%).

Intermediate 25 (I-25)

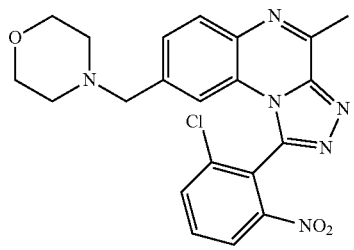 [SMILES: Cc1nc2ccc(CN3CCOCC3)cc2n2c(-c3c(Cl)cccc3[N+](=O)[O-])nnc12]

Intermediate I-25 was synthesized following a similar approach described for compound B-3. Starting from I-24 (0.035 g, 0.095 mmol) intermediate compound I-25 was obtained (0.011 g, 27%).

B. Synthesis of Final Compounds

Example 1a and 1b 1-(5-Butoxypyridin-3-yl)-4-methyl-8-(morpholin-4-ylmethyl) [1,2,4]triazolo[4,3-a]quinoxaline hydrochloride (B-1a) and oxalate (B-1b)

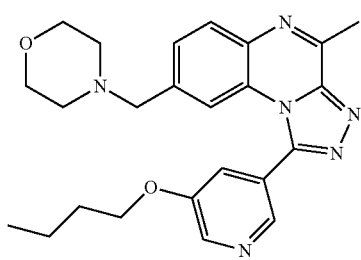

.2 HCl (B-1a) or x C$_2$H$_2$O$_4$ (B-1b)

Formation of B-1a

To a solution of intermediate compound I-5 (7.5 g, 18.19 mmol) in THF/H$_2$O (10:1, 180 mL), Pd(AcO)$_2$ (0.12 g, 0.54 mmol), XantPhos (0.52 g, 1.09 mmol), Cs$_2$CO$_3$ (23.88 g, 72.76 mmol) and intermediate compound I-20 (4.51 g, 21.82 mmol) were added. The r.m. was closed in a sealed tube and stirred at r.t. for 10 min and then at 114° C. for 45 min. Then, the crude mixture was diluted with EtOAc and H$_2$O, the organic layer separated, dried (MgSO$_4$), filtered and the solvent concentrated in vacuo. The crude mixture was purified by chromatography (silica, MeOH in DCM 0/100 to 2/98) the desired fractions were collected and the solvent concentrated in vacuo to give a pale red oil. This material was then dissolved in EtOAc (50 mL) and treated dropwise with HCl (4 M in dioxane, 1.2 eq, and 3.55 mL). The mixture was stirred at room temperature for 30 min and then evaporated under vacuum. The slurry was treated with 120 mL of DIPE and stirred again for additional 40 min. The formed precipitate was filtered off, washed with DIPE, dried under vacuum to yield final compound B-1a as a hydrochloride salt (5.2 g, 61%) $^1$H NMR (400 MHz, DMSO-d$_6$) δ ppm 0.94 (t, J=7.5 Hz, 3H), 1.46 (sxt, J=7.4 Hz, 2H), 1.69-1.82 (m, 2H), 2.88-3.04 (m, 2H), 2.96 (s, 3H), 3.19 (br. d, J=12.5 Hz, 2H), 3.75-3.98 (m, 4H), 4.18 (t, J=6.5 Hz, 2H), 4.34 (br. s., 2H), 7.68 (d, J=1.2 Hz, 1H), 8.00 (dd, J=8.5, 1.6 Hz, 1H), 8.09 (dd, J=2.4, 1.6 Hz, 1H), 8.13 (d, J=8.1 Hz, 1H), 8.70 (d, J=1.6 Hz, 1H), 8.75 (d, J=2.8 Hz, 1H), 12.03 (br. s., 1H).

Formation of B-1b

To a stirred solution of intermediate I-19 (0.108 g, 0.3 mmol), morpholine (0.03 mL, 0.33 mmol) and acetic acid (0.017 mL, 0.3 mmol) in DCE (5 mL) was added triacetoxy sodium borohydride (0.076 g, 0.3 mmol) and the mixture was stirred at room temperature overnight. Water and ethyl acetate were added, and the organic phase was separated, dried (MgSO$_4$), filtered and concentrated in vacuo. The crude mixture was purified by chromatography (silica, MeOH in DCM 0/100 to 10/90), the desired fractions were collected and concentrated in vacuo. The product was dissolved in dioxane (2 mL), oxalic acid was added (0.024 g, 0.27 mmol), the mixture was stirred for 45 min, concentrated in vacuo and recrystallized from diethyl ether to yield final compound B-1b as an oxalate salt (0.084 g, 54%).

(Spectrum of the free base) $^1$H NMR (300 MHz, DMSO-d$_6$) δ ppm 0.93 (t, J=7.4 Hz, 3H), 1.45 (sxt, J=7.4 Hz, 2H), 1.67-1.82 (m, 2H), 2.37 (br. s., 4H), 2.93 (s, 3H), 3.50 (br. s., 4H), 3.60 (s, 2H), 4.11 (t, J=6.5 Hz, 2H), 7.54 (s, 1H), 7.55 (d, J=8.8 Hz, 1H), 7.88 (br. s, 1H), 8.01 (d, J=8.1 Hz, 1H), 8.54 (s, 1H), 8.66 (d, J=2.5 Hz, 1H).

Example 2

1-(5-Butoxy-2-chlorophenyl)-4-methyl-8-(morpholin-4-ylmethyl) [1,2,4]triazolo-[4,3-a]quinoxaline hydrochloride (B-2)

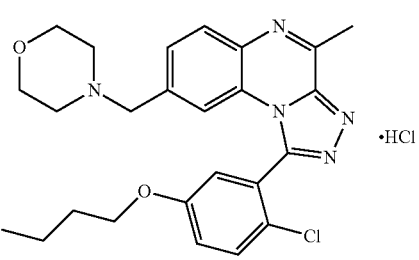 [SMILES: CCCCOc1ccc(Cl)c(-c2nnc3c(C)nc4ccc(CN5CCOCC5)cc4n23)c1 ; Cl]

B-2 was synthesized as previously described for the synthesis of final compound B-1a. Starting from I-11a (0.2 g, 0.45 mmol) and intermediate compound I-20, final compound B-2 was obtained (0.03 g, 14%). $^1$H NMR (300 MHz, DMSO-$d_6$) δ ppm 0.93 (t, J=7.4 Hz, 3H), 1.44 (sxt, J=7.3 Hz, 2H), 1.73 (quin, J=6.9 Hz, 2H), 2.93 (br. s., 1H), 2.97 (s, 3H), 3.19 (br. s., 1H), 3.77 (br. s., 2H), 3.92 (br. s., 2H), 3.98-4.14 (m, 2H), 4.31 (br. s., 2H), 5.76 (s, 2H), 7.25 (br. s., 1H), 7.33-7.50 (m, 2H), 7.73 (d, J=8.8 Hz, 1H), 7.96 (br. s., 1H), 8.16 (d, J=8.1 Hz, 1H), 11.31 (br. s., 1H).

Example 3

1-(2-Chlorophenyl)-4-methyl-8-(morpholin-4-ylmethyl)[1,2,4]triazolo[4,3-a]-quinoxaline (B-3)

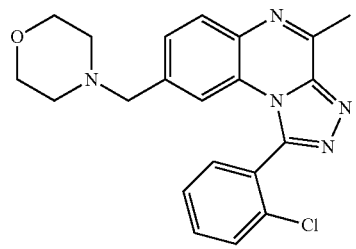 [SMILES: Cc1nc2ccc(CN3CCOCC3)cc2n2c(-c3ccccc3Cl)nnc12]

Morpholine (1.37 mL, 15.67 mmol) was added to a stirred solution of intermediate I-8 (2.3 g, 7.12 mmol) dissolved in DCE (50 mL) and the mixture was heated at 80° C. for 15 min under microwave irradiation (the reaction was divided in three batches). Then triacetoxy sodium borohydride (1.81 g, 8.55 mmol) was added portionwise and the mixture was heated again at the same conditions as before for 20 min. The mixture was then quenched with H$_2$O and extracted with DCM. The organic layer was separated, dried (Na$_2$SO$_4$), filtered and the solvent evaporated in vacuo. The crude compound was purified by chromatography (silica, MeOH in EtOAC 2/98 to 10/90) the desired fractions were collected and the solvent evaporated to yield final compound B-3 as pale yellow solid that was further washed with diethyl ether/DIPE (1.6 g, 57%). $^1$H NMR (400 MHz, CDCl$_3$) δ ppm 2.24-2.41 (m, 4H), 3.08 (s, 3H), 3.42 (s, 2H), 3.53-3.69 (m, 4H), 7.37 (d, J=1.2 Hz, 1H), 7.49 (dd, J=8.3, 1.6 Hz, 1H), 7.54-7.62 (m, 1H), 7.64-7.75 (m, 3H), 7.99 (d, J=8.3 Hz, 1H).

Example 4

N-{[1-(2-Chlorophenyl)-4-methyl[1,2,4]triazolo[4,3-a]quinoxalin-8-yl]methyl}-ethanamine (B-4)

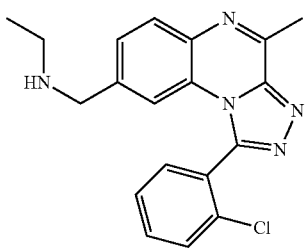 [SMILES: CCNCc1ccc2nc(C)c3nnc(-c4ccccc4Cl)n3c2c1]

Intermediate I-8 (0.300 g, 0.93 mmol), ethylamine hydrochloride (0.227 mL, 2.78 mmol) and Et$_3$N (0.388 mL, 2.78 mmol) were dissolved in DCE (11 mL). To this mixture 300 mg of MgSO$_4$ was added and everything was stirred at r.t. for 1.3 h. The solid was filtered off, and then MeOH (3 mL) followed by NaBH$_4$ (0.07 g, 1.85 mmol) were added to the filtrate and the solution was stirred at r.t. for additional 15 min. The r.m. was quenched with H$_2$O and extracted with DCM. The organic layers were separated, dried (MgSO$_4$), filtered and the solvent concentrated in vacuo. The crude mixture was purified by chromatography (silica; MeOH in DCM 0/100 to 10/90) yielding final compound B-4 as solid material (0.186 g, 57%). $^1$H NMR (500 MHz, CDCl$_3$) δ ppm 1.03 (t, J=7.1 Hz, 3H), 2.45-2.57 (m, 2H), 3.08 (s, 3H), 3.69-3.79 (m, 2H), 7.27 (br. s., 1H), 7.50 (d, J=8.4 Hz, 1H), 7.53-7.59 (m, 1H), 7.61-7.68 (m, 2H), 7.70 (d, J=6.9 Hz, 1H), 7.99 (d, J=8.1 Hz, 1H).

Example 5

1-(2-Chloro-6-fluorophenyl)-4-methyl-8-(morpholin-4-ylmethyl) [1,2,4]triazolo[4,3-a]quinoxaline (B-5)

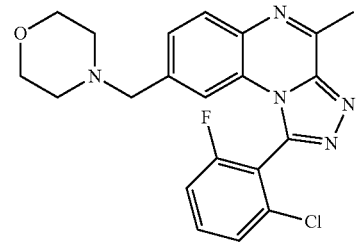 [SMILES: Cc1nc2ccc(CN3CCOCC3)cc2n2c(-c3c(F)cccc3Cl)nnc12]

Morpholine (0.056 mL, 0.64 mmol) was added to a stirred solution of intermediate I-17 (0.1 g, 0.29 mmol) dissolved in DCE (5 mL) and the mixture was heated at 120° C. for 15 min under microwave irradiation. Then sodium triacetoxy borohydride (0.075 g, 0.35 mmol) was added portionwise and the mixture was heated again at 80° C. for 20 min under microwave irradiation. The r.m. was then quenched with H$_2$O and extracted with DCM. The organic layer was separated, dried (Na$_2$SO$_4$), filtered and the solvent evaporated in vacuo. The crude compound was purified by chromatography (silica, MeOH in EtOAc 2/98 to 10/90) the desired fractions were collected and the solvent evaporated to yield final compound B-5 as pale yellow solid that was further washed with diethyl ether/DIPE (0.045 g, 37%). $^1$H NMR (400 MHz, CHLOROFORM-d) δ ppm 2.25-2.41 (m, 4H) 3.09 (s, 3H) 3.39-3.52 (m, 2H) 3.54-3.68 (m, 4H) 7.32 (t, J=8.3 Hz, 1H) 7.41 (br. s, 1H) 7.47-7.51 (m, 1H) 7.52 (d, J=8.3 Hz, 1H) 7.68 (td, J=8.3, 5.8 Hz, 1H) 8.01 (d, J=8.3 Hz, 1H).

Example 6

1-(5-Butoxypyridin-3-yl)-4-methyl-8-(morpholin-4-yl-[$^3$H]methyl)[1,2,4]triazolo[4,3-a]quinoxaline ([$^3$H]B-1a)

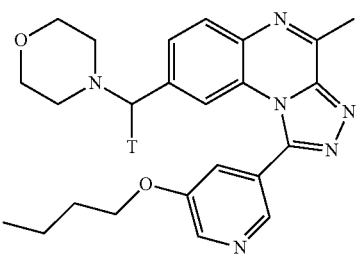

Intermediate compound I-19 (0.002 g, 5.53 mol) was dissolved in dichloromethane (0.1 mL) in a dry wheaton vial. Morpholine (0.271 mL, 27.67 mol) and titanium tetra (isopropoxide) (0.82 mL, 27.67 mol) were added under argon atmosphere and stirred overnight at room temperature. The reaction mixture was transferred to a tritiation ampoule and attached to a tritium manifold (RC Tritec). Dichloromethane was lyophilized of and replaced by dry THF (0.2 mL). The mixture was lyophilized again and Platinum on carbon (4 mg, 5%) was added together with dry THF (0.2 mL). The reaction mixture was degassed (3×) and placed under tritium atmosphere (750 mbar at room temperature) for 60 minutes at room temperature. The tritium atmosphere was removed and the volatile components lyophilized to a waste ampoule. The crude mixture was rinsed and lyophilized with MeOH (3×0.15 mL), filtered over an Acrodisk® and dissolved in ethanol (10 mL). This stock solution was purified over prep-HPLC and resulted in 230 MBq with a radiochemical purity of >98% and specific activity of 726 GBq/mmol.

Example 7

Radiosynthesis Production of [$^{18}$F]fluoride and of 1-(2-Chloro-6-[$^{18}$F]fluorophenyl)-4-methyl-8-(morpholin-4-ylmethyl) [1,2,4]triazolo[4,3-a]quinoxaline ([$^{18}$F]B-5)

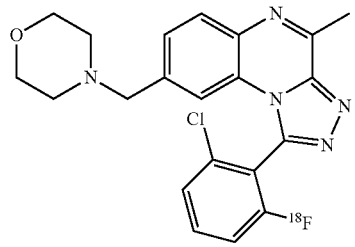 [SMILES: Cc1nc2ccc(CN3CCOCC3)cc2n2c(-c3c([18F])cccc3Cl)nnc12]

[$^{18}$F]fluoride ([$^{18}$F]F) was produced by an [$^{18}$O(p,n)$^{18}$F] reaction by irradiation of 2 mL of 97% enriched [$^{18}$O]H$_2$O (Rotem HYOX18, Rotem Industries, Beer Sheva, Israel) in a niobium target using 18-MeV protons from a Cyclone 18/9 cyclotron (Ion Beam Applications, Louvain-la-Neuve, Belgium). After irradiation, the resultant [$^{18}$F]F$^-$ was separated from [$^{18}$O]H$_2$O using a SepPak™ Light Accell plus QMA anion exchange cartridge (Waters, CO$_3^{2-}$ form). [$^{18}$F]F$^-$ was eluted from the cartridge using a mixture of 0.38 mL of a solution containing K$_2$CO$_3$ (0.00247 g) and Kryptofix 222 (0.00279 g) dissolved in H$_2$O/MeCN (0.75 mL; 5:95 v/v) and 0.38 mL MeCN. The solution was evaporated under a stream of helium at 80° C. and 35 watt by applying microwave heating and further dried by azeotropic distillation using MeCN (1 mL) at a temperature of 80° C. and a power of 35 watt in the microwave cavity. The precursor for the radiolabeling, I-25 (0.0013 g, 0.0029 mmol) was dissolved in anhydrous DMF (0.35 mL), this solution was added to the dried [$^{18}$F]F$^-$/K$_2$CO$_3$/Kryptofix® 222 complex, and the nucleophilic substitution reaction was carried out using microwave heating at 140° C. and 50 watt for 6 min. Next, the crude mixture was diluted with 0.05 M NaOAc buffer pH 5.5 (0.6 mL) and injected onto the HPLC system consisting of a semi-preparative XBridge™ column (C$_{18}$, 5 μm, 4.6 mm×150 mm; Waters) that was eluted with a mixture of 0.05 M NaOAc buffer pH 5.5 and EtOH (73:27 v/v) at a flow rate of 1 mL/min. UV detection of the HPLC eluate was performed at 254 nm. The radiolabeled product [$^{18}$F]B-5 was collected after about 25 min. The collected peak corresponding to [18F]B-5 was then diluted with saline (Mini Plasco®, Braun, Melsungen, Germany) to obtain a final EtOH concentration of <10% and the solution was sterile filtered through a 0.22 m membrane filter (Millex®-GV, Millipore). The purity of the radiotracer was analyzed using an HPLC system consisting of an XBridge™ column (C$_{18}$, 5 μm, 4.6 mm×150 mm; Waters) eluted with a mixture of 0.05 M NaOAc buffer pH 5.5 and EtOH (65:35 v/v) at a flow rate of 1 mL/min (Rt=7.5 min). UV detection of the HPLC eluate was performed at 254 nm. [$^{18}$F]B-5 was synthesized in 45% radiochemical yield (relative to starting radioactivity [$^{18}$F]F$^-$, decay corrected, n=6). The radiochemical purity as examined using the above described analytical HPLC system was >99% and the average specific radioactivity was found to be 215 GBq/μmol at EOS (n=6).

TABLE 1

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

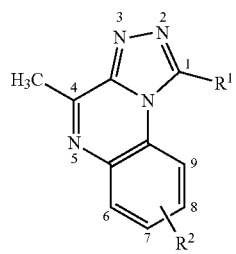

| Co. no. | Ex. no. | $R^1$ | $R^2$ | Salt form |
|---|---|---|---|---|
| B-1a | E1a* | 5-(BuO)pyridin-3-yl | (8)-morpholin-4-ylmethyl | •2HCl |
| [³H]B-1a | [³H]B-1a* | 5-(BuO)pyridin-3-yl | (8)-(T)(morpholin-4-yl)methyl | |
| B-1b | E1b* | 5-(BuO)pyridin-3-yl | (8)-morpholin-4-ylmethyl | •xC$_2$H$_2$O$_4$ |
| B-2 | E2* | 2-Cl-4-(BuO)phenyl | (8)-morpholin-4-ylmethyl | •HCl |
| B-3 | E3* | 2-Cl-phenyl | (8)-morpholin-4-ylmethyl | |
| B-4 | E4* | 2-Cl-phenyl | (8)-ethylaminomethyl | |
| B-5 | E5* | 2-Cl-6-F-phenyl | (8)-morpholin-4-ylmethyl | |

TABLE 1-continued

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

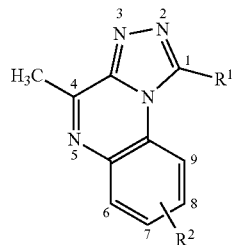

| Co. no. | Ex. no. | R¹ | R² | Salt form |
|---|---|---|---|---|
| [¹⁸F]B-5 | [¹⁸F]B-5* | 2-Cl, 6-¹⁸F-phenyl | (8)-CH₂-morpholine | |
| B-6 | E1b | 2-Cl, 5-iPrO-phenyl | (8)-CH₂-morpholine | •HCl |
| B-7 | E1b | 2-Cl, 5-EtO-phenyl | (8)-CH₂-morpholine | •HCl |
| B-8 | E1b | 2-Cl, 5-PrO-phenyl | (8)-CH₂-morpholine | •HCl |
| B-9 | E3 | 2-Cl, 5-F-phenyl | (8)-CH₂-morpholine | |
| B-10 | E1a | 2-Cl, 5-MeO-phenyl | (8)-CH₂-morpholine | |
| B-11 | E3 | 2-Cl, 5-BuO-phenyl | (8)-CH₂-N(CH₃)₂ | |

TABLE 1-continued

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

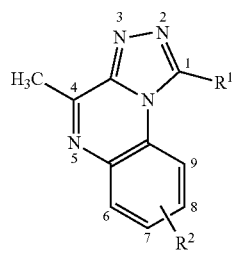

| Co. no. | Ex. no. | R$^1$ | R$^2$ | Salt form |
|---|---|---|---|---|
| B-12 | E3 | 5-methoxypyridin-3-yl | (8)-CH$_2$-morpholino | |
| B-13 | E3 | 2-chlorophenyl | (8)-CH$_2$-N(CH$_3$)$_2$ | |
| B-14 | E4 | 2-chloro-4-propoxyphenyl | (8)-CH$_2$-NHEt | |
| B-15 | E1b | 2-chloro-4-propoxyphenyl | (8)-CH$_2$-N(CH$_3$)$_2$ | •0.4HCl |
| B-16 | E1b | 5-propoxypyridin-3-yl | (8)-CH$_2$-morpholino | •HCl |
| B-17 | E3 | 2-chloro-4-isopropoxyphenyl | (8)-CH$_2$-N(CH$_3$)$_2$ | |
| B-18 | E3 | 2-chloro-4-ethoxyphenyl | (8)-CH$_2$-N(CH$_3$)$_2$ | |

TABLE 1-continued

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

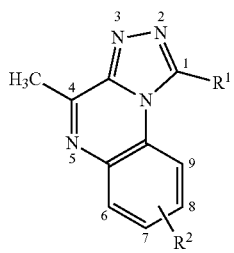

| Co. no. | Ex. no. | R¹ | R² | Salt form |
|---|---|---|---|---|
| B-19 | E4 | 2-chloro-5-isopropoxyphenyl | (8)-NH-ethyl | •HCl |
| B-20 | E4 | 2-chloro-4-butoxyphenyl | (8)-NH-isopropyl | |
| B-21 | E4 | 5-butoxypyridin-3-yl | (8)-NH-ethyl | •1.4HCl |
| B-22 | E4 | 2-chloro-4-ethoxyphenyl | (8)-NH-ethyl | |
| B-22a | E4 | 2-chloro-4-ethoxyphenyl | (8)-NH-ethyl | •HCl |
| B-23 | E4 | 5-butoxypyridin-3-yl | (8)-NH-isopropyl | •0.6HCl |
| B-24 | E4 | 5-propoxypyridin-3-yl | (8)-NH-ethyl | •HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

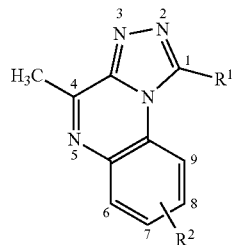

| Co. no. | Ex. no. | R¹ | R² | Salt form |
|---|---|---|---|---|
| B-25 | E4 | 4-Cl, 5-BuO-phenyl | (8) CH₂NHMe | 2HCl |
| B-26 | E1b | 5-(cyclopropylmethoxy)pyridin-3-yl | (8) CH₂-morpholinyl | HCl |
| B-27 | E1b | 5-BuO-pyridin-3-yl | (8) CH₂NMe₂ | 2HCl |
| B-28 | E4 | 5-BuO-pyridin-3-yl | (8) CH₂NHMe | 1.7HCl |
| B-29 | E3 | 2-Cl, 5-BuO-pyridin-3-yl | (8) CH₂-morpholinyl | — |
| B-30 | E1b | 5-(cyclopropylmethoxy)pyridin-3-yl | (8) CH₂NMe₂ | 1.5HCl |
| B-31 | E4 | 5-(cyclopropylmethoxy)pyridin-3-yl | (8) CH₂NHiPr | 1.7HCl |

TABLE 1-continued

The following compounds were prepared following the methods exemplified in the Experimental Part (Ex. No.). Compounds exemplified and described in the experimental part are marked with an asterisk *. Bu means 1-butyl. Compound 22 was isolated as the free base and also converted to a hydrochloride salt (compound 22a).

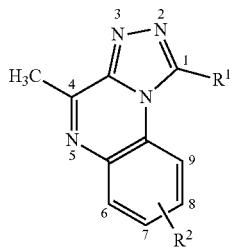

| Co. no. | Ex. no. | R¹ | R² | Salt form |
|---|---|---|---|---|
| B-32 | E4 |  | (8)- | HCl |

Analytical Part
LCMS

For LC-MS characterization of the compounds of the present invention, the following methods were used.

General Procedure A

The HPLC measurement was performed using an HP 1100 (Agilent Technologies) system comprising a pump (quaternary or binary) with degasser, an autosampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure B

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure D

The HPLC measurement was performed using an Agilent 1100 module comprising a pump, a diode-array detector (DAD) (Agilent 1200) (wavelength used 254 nm), a column heater and a column as specified in the respective methods below. Flow from the column was split to a Agilent MSD Serie G1956A. MS detector was configured with API-ES (atmospheric pressure electrospray ionization). Mass spectra were acquired by scanning from 105 to 1400. The capillary needle voltage was 3000 V for positive ionization mode. Fragmentation voltage was 70 V. Drying gas temperature was maintained at 350° C. at a flow of 12 l/min.

Method 1

In addition to the general procedure A: Reversed phase HPLC was carried out on a Sunfire-C18 column (2.5 µm, 2.1×30 mm) from Waters, with a flow rate of 1.0 ml/min, at 60° C. The gradient conditions used are: 95% A (0.5 g/l ammonium acetate solution+5% of acetonitrile), 2.5% B (acetonitrile), 2.5% C (methanol) to 50% B, 50% C in 6.5 minutes, kept till 7.0 minutes and equilibrated to initial conditions at 7.3 minutes until 9.0 minutes. Injection volume 2 µl. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 2

In addition to the general procedure B: Reversed phase UPLC was carried out on a BEH-C18 column (1.7 µm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 2.8 minutes, to 5% A, 95% B in 3.6 minutes, kept till 3.8 minutes and equilibrated to initial conditions at 4.0 minutes until 5.0 minutes. Injection volume 0.5 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 3

In addition to the general procedure B: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 4

In addition to the general procedure D: Reversed phase HPLC was carried out on a YMC pack ODS-AQ C18 column (3 μm, 50 mm×4.6 mm) with a flow rate of 2.6 mL/min, at 35° C. A gradient elution was performed from 95% ($H_2O$+0.1% HCOOH)/5% $CH_3CN$ to 5% ($H_2O$+0.1% HCOOH)/95% $CH_3CN$ in 4.8 min and held for 1.0 min; then to 95% ($H_2O$+0.1% HCOOH)/5% $CH_3CN$ in 0.2 min. The injection volume was 2 μL. Acquisition ranges were set to 190-400 nm for the UV-PDA detector and 100-1400 m/z for the MS detector.

Method 5

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 μl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

Method 6 same gradient as method 4; column used: RRHD Eclipse Plus-C18 (1.8 μm, 2.1×50 mm) from Agilent.

Method 7

In addition to the general procedure C: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute, 100% B for 1 minute and reequilibrate with 100% A for 1.5 minutes. An injection volume of 10 μl was used.

Cone voltage was 10 V for positive ionization mode and 20 V for negative ionization mode.

Method 8

In addition to the general procedure A: Reversed phase HPLC was carried out on an Eclipse Plus-C18 column (3.5 μm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), kept 0.2 minutes, to 100% B in 3.0 minutes, kept till 3.15 minutes and equilibrated to initial conditions at 3.30 minutes until 5.0 minutes. Injection volume 2 μl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V and 50 V for positive ionization mode and 30 V for negative ionization mode.

Method 9

In addition to the general procedure B: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 10

In addition to the general procedure C: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM $NH_4AcO$ in $H_2O$/$CH_3CN$ 95/5; mobile phase B: $CH_3CN$) were used to run a gradient condition from 95% A and 5% B to 5% A and 95% B in 1.3 minutes and hold for 0.7 minutes. An injection volume of 0.75 ml was used. Cone voltage was 10 V for positive ionization mode and 20 V for negative ionization mode.

GCMS

General Procedure for Agilent GC/MSD Instrument

The GC measurement was performed using a 6890 Series Gas Chromatograph (Agilent Technologies) system comprising a 7683 Series injector and autosampler, a column oven and a column as specified in the respective methods below, coupled to a 5973N MSD Mass Selective Detector (single quadrupole, Agilent Technologies). The MS detector was configured with an electronic impact ionization source/chemical ionization source (EI/CI). EI low-resolution mass spectra were acquired by scanning from 50 to 550 at a rate of 14.29 scans/s. The source temperature was maintained at 230° C. Helium was used as the nebulizer gas. Data acquisition was performed with Chemstation-Open Action software.

Method 1

In addition to the general procedure: GC was carried out on a J&W HP-5MS column (20 m×0.18 mm, 0.18 μm) from Agilent Technologies, with a flow rate of 0.7 ml/min. The temperature gradient applied was: initial temperature 50° C., hold for 2.0 min, then a 50° C./min ramp applied for 5.0 min until 300° C. and hold for 3.0 min in a 10 min run. Front inlet temperature was 250° C. Split injection mode was used, 0.2 μl injection volume, with a 50/1 ratio into the GC/MS system.

Melting Points

Values are either peak values or melt ranges, and are obtained with experimental uncertainties that are commonly associated with this analytical method.

Mettler FP62 Apparatus

For a number of compounds, melting points were determined in open capillary tubes on a Mettler FP62 apparatus. Melting points were measured with a temperature gradient of 1, 3, 5 or 10° C./minute. Maximum temperature was 300° C. The melting point was read from a digital display.

DSC823e Mettler-Toledo Apparatus

For a number of compounds, melting points were determined with a DSC823e Mettler-Toledo (indicated with DSC in table 2). Melting points were measured with a temperature gradient of 30° C./minute. Maximum temperature was 400° C.

Nuclear Magnetic Resonance (NMR)

$^1$H NMR spectra were recorded either on a Bruker Avance III, on a Bruker DPX-400 or on a Bruker AV-500 spectrometer with standard pulse sequences, operating at 300 MHz, 400 MHz and 500 MHz respectively. Chemical shifts (δ) are reported in parts per million (ppm) downfield from tetramethylsilane (TMS), which was used as internal standard.

TABLE 2

Analytical data-R$_t$ means retention time (in minutes), [M + H]$^+$ means the protonated mass of the compound, method refers to the method used for (LC)MS, dec means decomposition.

| Co. no. | mp (° C.) | [MH$^+$] | Rt | LCMS method |
|---|---|---|---|---|
| B-1a | 249.9 (DSC) | 433 | 0.92 | 10 |
| B-1b | 211.3 | 433 | 1.8 | 4 |
| B-2 | 221.7 (DSC) | 466 | 2.18 | 4 |
| B-3 | 160.4 | 394 | 1.89 | 3 |
| B-4 | 106.9 | 352 | 0.93 | 2 |
| B-5 | 159 | 412 | 1.98 | 3 |
| B-6 | 247.6 | 452 | 1.88 | 4 |
| B-7 | 225.8 | 438 | 1.74 | 4 |
| B-8 | 250.5 | 452 | 1.96 | 4 |
| B-9 | 176.7 | 412 | 2.02 | 3 |
| B-10 | 159.5 | 424 | 1.57 | 4 |
| B-11 | 83.4 | 424 | 1.97 | 4 |
| B-12 | 136.3 | 391 | 1.29 | 3 |
| B-13 | >300 (dec) | 352 | 1.35 | 2 |
| B-14 | 115 | 410 | 1.85 | 4 |
| B-15 | 256 (DSC) | 410 | 1.81 | 4 |
| B-16 | 213.8 | 419 | 2.06 | 6 |
| B-17 | 144.2 (DSC) | 410 | 1.73 | 4 |
| B-18 | 127.8 | 396 | 1.62 | 4 |
| B-19 | 235.3 | 410 | 1.79 | 4 |
| B-20 | 118 | 438 | 2.1 | 4 |
| B-21 | 228.8 | 391 | 1.71 | 6 |
| B-22 | 117.4 | 396 | 1.67 | 4 |
| B-22a | n.d. | 396 | 1.66 | 4 |
| B-23 | 249.3 | 405 | 2.01 | 6 |
| B-24 | 258 | 377 | 1.35 | 6 |
| B-25 | 203.5 | 410 | 1.97 | 4 |
| B-26 | 227.2 | 431 | 1.54 | 4 |
| B-27 | nd | 391 | 1.7 | 4 |
| B-28 | 197.7 | 377 | 1.66 | 4 |
| B-29 | nd | 467 | 1.28 | 9 |
| B-30 | 213.8 | 389 | 1.53 | 4 |

TABLE 2-continued

Analytical data-R$_t$ means retention time (in minutes), [M + H]$^+$ means the protonated mass of the compound, method refers to the method used for (LC)MS, dec means decomposition.

| Co. no. | mp (° C.) | [MH$^+$] | Rt | LCMS method |
|---|---|---|---|---|
| B-31 | 279.9 | 403 | 1.59 | 4 |
| B-32 | 244.9 | 389 | 1.49 | 4 |

Pharmacological Examples

The compounds of formula (I) and pharmaceutically acceptable salts and solvates thereof provided in the present invention are inhibitors of PDE2, particularly of PDE2A, and to a lesser extent of PDE10, particularly of PDE10A. The behaviour of the compounds according to formula (I) and the combinations according to the invention is shown in Tables 3-9 below.

In Vitro Assay PDE2A

Human recombinant PDE2A (hPDE2A) was expressed in Sf9 cells using a recombinant rPDE10A baculovirus construct. Cells were harvested after 48 h of infection and the hPDE2A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM MgCl$_2$, 1.7 mM EGTA). 10 μl of hPDE2A enzyme in incubation buffer was added and the reaction was started by addition of 10 μl substrate to a final concentration of 10 M cGMP and 0.01 μCi $^3$H-cGMP. The reaction was incubated for 45 minutes at room temperature. After incubation, the reaction was stopped with 20 μl of stop solution consisting of 17.8 mg/ml PDE SPA scintillation proximity assay) beads supplemented with 200 mM ZnCl$_2$. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blanc value versus compound concentration and the half maximal inhibitory concentration (IC$_{50}$) value is derived from this curve.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Compound dilutions (0.4 μl) were added in 384 well plates to 20 μl of incubation buffer (50 mM Tris pH 7.8, 8.3 mM MgCl$_2$, 1.7 mM EGTA). 10 μl of rPDE10A enzyme in incubation buffer was added and the reaction was started by addition of 10 μl substrate to a final concentration of 60 nM cAMP and 0.008 μCi $^3$H-cAMP. The reaction was incubated for 60 minutes at room temperature. After incubation, the reaction was stopped with 20 μl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value subtracted with blanc value versus compound concentration and the half maximal inhibitory concentration ($IC_{50}$) value is derived from this curve. The results of this test are shown in table 3 below.

TABLE 3

Pharmacological data for compounds according to the invention.

| Co. No. | $pIC_{50}$ PDE2 | $PIC_{50}$ PDE10 |
|---|---|---|
| B-1a | 7.9 | 5.32 |
| B-1b | 8.13 | 5.39 |
| B-2 | 8.11 | 5.79 |
| B-3 | 8.64 | 7.47 |
| B-4 | 7.69 | 6.8 |
| B-5 | 8.86 | 7.86 |
| B-6 | 8.32 | 5.73 |
| B-7 | 8.21 | 6.58 |
| B-8 | 8.19 | 6.49 |
| B-9 | 8.02 | 7.07 |
| B-10 | 7.98 | 6.98 |
| B-11 | 7.94 | 5.67 |
| B-12 | 7.92 | 6.57 |
| B-13 | 7.7 | 6.97 |
| B-14 | 7.68 | 5.75 |
| B-15 | 7.66 | 5.83 |
| B-16 | 7.52 | 5.21 |
| B-17 | 7.45 | 5.8 |
| B-18 | 7.44 | 6.5 |
| B-19 | 7.34 | 5.07 |
| B-20 | 7.35 | 5.38 |
| B-21 | 7.31 | <5 |
| B-22 | n.t. | n.t. |
| B-22a | 7.36 | 6.04 |
| B-23 | 7.28 | <5 |
| B-24 | 6.71 | <5 |
| B-25 | 7.74 | 5.04 |
| B-26 | 7.65 | 5.44 |
| B-27 | 7.13 | 5.03 |
| B-28 | 7.04 | <5 |
| B-29 | 6.93 | <5 |
| B-30 | 6.87 | <5 |
| B-31 | 6.48 | 5.84 |
| B-32 | 6.46 | <5 |

$pIC_{50}$ corresponds to the $-\log IC_{50}$ expressed in mol/L.
n.t. means not tested.

Effect of PDE-Inhibitors
Ex-Vivo Studies in Rat

Upon arrival, the animals (body weight 210-240 g) were housed in groups of 5 and fed normal chow ad libitum.

Compounds and/or solvent were administered either orally, subcutaneously or IV. Depending on the experimental setup, the animals were sacrificed by microwave irradiation (Muromachi, MMW-05) for 1.5 sec at 5 kW, either, 30, or 60, min after drug/solvent administration. After microwave, the rats were decapitated and the heads cooled immediately with ice cold physiological saline. The scalp was opened and the brain was removed and different brain regions (striatum, hippocampus, cortex and/or cerebellum) were dissected and transferred into pre-weighed homogenization tubes (Collection Microtubes, Qiagen) containing a steel ball (Stainless steel beads 5 mm, cat nr 69989, Qiagen), and kept on dry ice. 10 vol (w/v) of 0.1N HCl were added. The tissue was homogenized for 3 min at 30 Hz using a Tissuelyser (Qiagen).

The homogenate was transferred into an Eppendorf tube (1.5 ml) and after centrifugation for 15 min at 1600 g in a pre-cooled (4° C.) Eppendorf centrifuge, the supernatant was collected and stored at −80° C. until analysis.

Cyclic-GMP levels were determined on 1/4 (striatum, hippocampus, cortex) or 1/10 (cerebellum) diluted samples using the cGMP Complete EIA kit from Enzo Life Sciences.

Cyclic-AMP levels were determined on 1/10 and 1/25 diluted samples using the LANCE Ultra cAMP kit from Perkin Elmer (code TRF0263).

Results were calculated from a sigmoidal standard curve by non linear regression using GraphPadPrism software. The results of this test are shown in table 4 below.

The cAMP and cGMP levels were measured in the rat brain (hippocampus and striatum) to establish in vivo target engagement and central pharmacological effect of PDE2 inhibition, as well as to establish the combined effect of PDE2 and PDE10 inhibition. PDE2 inhibition results in a marked increase in brain cGMP levels. After combined administration of the PDE2 inhibitor B-1a, and of MP-10, the resulting increase in cGMP exceeded the calculated cumulative effect on cGMP levels after PDE2 and PDE10 inhibition separately, suggesting a synergism between PDE2 and PDE10 inhibition (Table 5). Without wishing to be bound by theory, this may be related to increased affinity of B1-a to PDE2 in conditions of high intracellular cGMP concentrations. The NO/cGMP signaling pathway has been shown to play an important role in the process underlying learning and memory, synaptic plasticity and neurogenesis, and in the regulation of corticostriatal synaptic transmission and motor behavior. The measured elevation of cGMP in brain tissue supports the further investigation of the use of PDE2 inhibitors in conditions with impaired NO/cGMP signaling such as cognitive dysfunction in psychiatric disorders, Alzheimer's disease (Mennitti, F. S. et al. Nature Rev. Drug Discovery 2006, 5, 660-669; Baratti, C. M., Boccia, M. M. Behav. Pharmacol. 1999; 10: 731-737; Prickaerts, J. et al. Neuroscience 2002; 113:349-359; Domek-Lopacińska K U, Strosznajder J B Mol Neurobiol. 2010; 41(2-3):129-37), major depression (Reierson, G. W. et al. Current Neuropharmacology 2011; 9:715-727) and movement disorders as Parkinson's and Huntington's disease (West, A. R. and Tseng K. Y. Neuroscience, 2011; 5:55-64; Kumar P, et al. Behav Pharmacol. 2010 May; 21(3):217-30).

TABLE 4 cAMP and cGMP levels measured in the rat brain with compounds according to the invention.

| | Hippocampus | | Striatum | |
|---|---|---|---|---|
| Compound dosed (10 mg/kg s.c., −1 h) | cAMP (% of Control) | cGMP (% of Control) | cAMP (% of Control) | cGMP (% of Control) |
| B-1a | 91 ± 9 | 298 ± 52** | 101 ± 21 | 240 ± 70** |
| B-11 | 117 ± 20 | 150 ± 42 | 88 ± 12 | 121 ± 20 |
| B-27 | 122 ± 10 | 104 ± 32 | 89 ± 6 | 128 ± 26 |

**$p < 0.005$ student T-test

TABLE 5

Potentiation of cGMP elevation by combined administration of B-1a and MP-10.

| | mean nmol cGMP/ml | sd | fold increase | incr vs contr (pmol cGMP/ml) (measured) | cumulative increase (pmol/ml) (calculated) |
|---|---|---|---|---|---|
| vehicle | 6.2 | 1.1 | 1 | | |
| MP-10 2.5 mpk | 8.7 | 2.9 | 1.4 | 2.4 | |
| B-1a 2.5 mpk | 11.6 | 1.9 | 1.9 | 5.4 | |
| B-1a 10 mpk | 16.0 | 5.7 | 2.6 | 9.7 | |
| MP-10 2.5 mpk + B-1a 2.5 mpk | 21.7 | 3.3 | 3.5 | 15.5 | 7.8 |
| MP-10 2.5 mpk + B-1a 10 mpk | 31.7 | 12.7 | 5.1 | 25.5 | 12.2 | mpk means mg per kg; sd means standard deviation; incr vs contr means increase versus control; cumulative increase means sum of increase induced by treatment of inhibitors separately.

In-Vivo Studies in Rat

Inhibition of Apomorphine-Induced Agitation in Rats (APO)

Overnight starved, male Wiga Wistar rats (Charles River, Germany; 200-260 g) were used. Apomorphine (1.0 mg/kg, i.v.)-induced agitation was scored every 5 min over the first hour after injection of apomorphine. The score system was: (3) pronounced, (2) moderate, (1) slight, and (0) absent. Criteria for drug-induced inhibition of agitation: fewer than 6 scores of 3 (0.16% false positives; n=2966), fewer than 6 scores of ≥2 (0.0% false positives) or fewer than 7 scores of ≥1 (0.0% false positives). For the present purpose, the cumulative agitation score over the whole 60-min observation period was used as a measure to describe the maximum effect (Max effect), i.e. the lowest median cumulative agitation score observed per dose group. The results of this test are shown in table 6 below. Selective PDE2 inhibitors do not affect apomorphine-induced behaviour while PDE10 inhibitors affect apomorphine-induced behaviour; when values of Max effect are <10 (low agitation) there is probably a combined PDE10 and PDE2 inhibitory effect.

TABLE 6

Inhibition of Apomorphine-induced Agitation in Rats: data for compounds according to the invention.

| | PO | | | SC | | |
|---|---|---|---|---|---|---|
| Co. No. | LAD | Max effect | Dose at Max Effect | LAD | Max effect | Dose at max effect |
| B-13 | | | | >10 | 20.5 | 10 |
| B-3 | | | | 5 | 14 | 5 |
| B-4 | | | | >10 | 21 | 10 |
| B-9 | | | | 2.5 | 9 | 10 |
| B-5 | | | | 0.63 | 1 | 40 |
| B-12 | | | | >10 | 21 | 10 |
| B-10 | >10 | 21 | 10 | | | |
| B-18 | | | | >10 | 22 | 10 |
| B-7 | | | | >10 | 24 | 10 |
| B-8 | | | | >10 | 23 | 10 |
| B-1a | | | | >40 | 23 | 40 |

LAD means lowest active dose, defined as the lowest dose at which ≥67% tested animals (when ≥3 animals are tested) respond to the criteria for drug-induced inhibition of agitation; PO means oral route; SC means subcutaneous route.

Inhibition of Apomorphine-induced Agitation in Rats in combination with MP-10 but the animals were simultaneously challenged with MP-10 (0.63 mg/kg) in addition to apomorphine (1.0 mg/kg) via one injection (2 ml/kg, i.v.), at a fixed time interval (standard 1 h) after s.c. or p.o. dosing of test compound or solvent. Twelve times, every 5 min, the intensity of agitation was scored 0 to 3. For the present purpose, the cumulative agitation score over the whole 60-min observation period was used for evaluation. Based on the frequency distribution of the cumulative agitation score in a series of solvent-pretreated control rats, a cumulative score <10 was adopted as all-or-none criterion for drug-induced inhibition of agitation (0.0% false positives in controls; n=93). The results of this test are shown in table 7 below.

TABLE 7

Inhibition of Apomorphine-induced Abnormal Behaviour in combination with MP-10 for compounds according to the invention

| Co. No. | Route | Time | dose | Inh. of agitation < 10 Effect |
|---|---|---|---|---|
| B-1a | SC | 60 | 0.63 | 18 |
| | | | 1.25 | 10 |
| | | | 2.5 | 11 |
| | | | 5 | 6 |
| | | | 10 | 7 |
| | | | 40 | 1 |
| B-6 | SC | 60 | 2.5 | 13 |
| | | | 10 | 1 |
| B-17 | SC | 60 | 10 | 12 |
| B-11 | SC | 60 | 2.5 | 17 |
| | | | 10 | 7 |
| B-18 | SC | 60 | 10 | 17 |
| B-26 | SC | 60 | 10 | 17 |
| B-27 | SC | 60 | 10 | 14 |

Figure 1B:
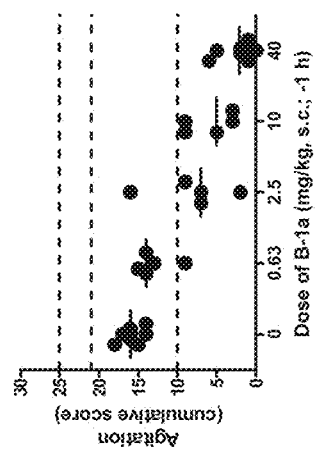
Figure 1C:
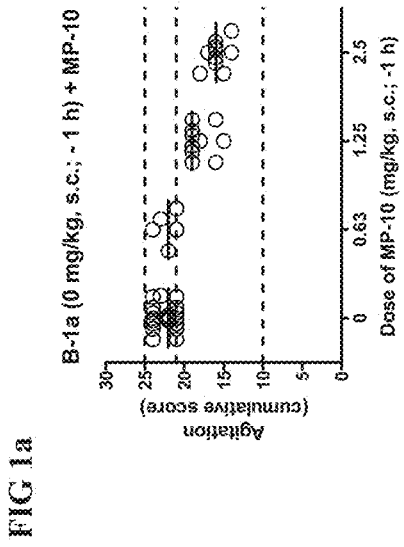

A representation of the effect on agitation of MP-10 (0.63-2.5 mg/kg, s.c.) and solvent (sol); and effect when MP-10 (at 2.5 mg/kg, s.c.) is dosed together with compound B-1a is provided in FIGS. 1a-c. When B-1a (40 mg/kg, s.c.) was dosed together with progressively increasing doses of MP-10, there was a potentiation in the magnitude of the effect of MP-10 without leftward shift of the dose-response curve (compare FIG. 1a with 1b). When MP-10 (2.5 mg/kg, s.c.) was dosed together with progressively increasing doses of B-1a, B-1a resulted in a dose-dependent further decrease of agitation, although it was ineffective against apomorphine when administered alone at the tested doses (without MP-10; Table 6).

Figure 2:
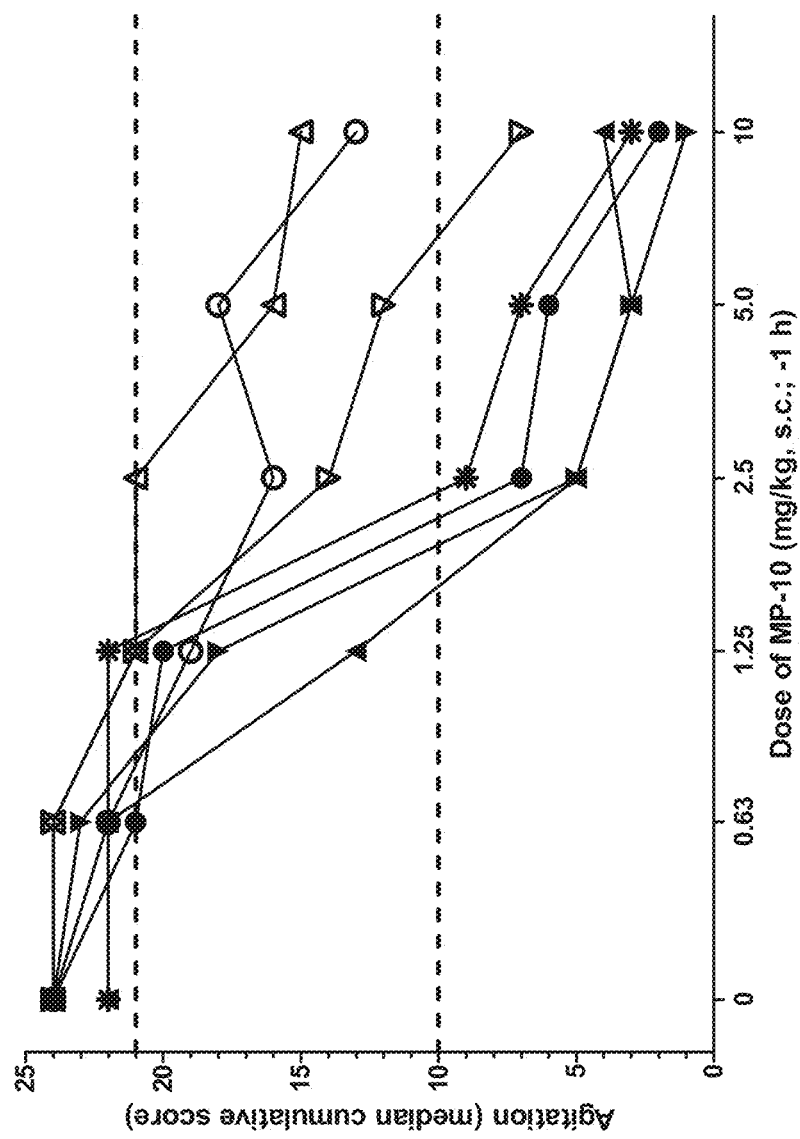
FIG. 2 shows the dose-dependent effect of MP-10 (−1 h, s.c.) on apomorphine-induced agitation (median score) as a function of dose of co-administered PDE2 inhibitor (PDE2-i) B-1a (0.63 to 10 mg/kg, s.c.; −1 h) or solvent (10 ml/kg, s.c.; −1 h). The dotted horizontal lines represent the critical levels for mild inhibition of agitation (score <21; upper line) and pronounced inhibition of agitation (score <10; bottom line).

FIG. 2 shows the effect of MP-10 (−1 h, s.c.) on apomorphine-induced agitation (median score per dose group) as a function of dose of the PDE2-i B-1a (0.63 to 10 mg/kg, s.c.; −1 h) or solvent (10 ml/kg, s.c.; −1 h). The dotted horizontal lines represent the critical levels for mild inhibition of agitation (score <21; upper line) and pronounced inhibition of agitation (score <10; bottom line). MP-10 dose-dependently inhibited agitation; the maximum effect size increased with increasing dose of B-1a. At low doses of co-administered B-1a (≤0.63 mg/kg), median agitation scores <10 were not obtained with MP-10 up to 10 mg/kg. At higher doses of B-1a, however, MP-10 reduced agitation to a score <10 at progressively lower doses.

Figure 3A:
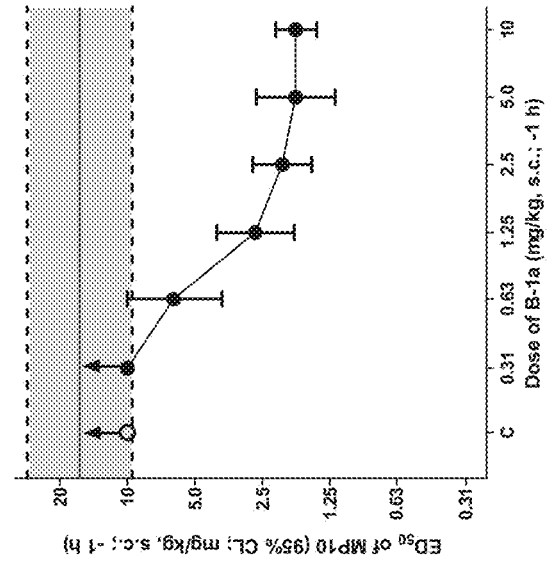
FIG. 3 shows the $ED_{50}$ (and 95% confidence limits) of MP-10 (−1 h, s.c.) for reducing apomorphine-induced agitation to a score <21 (FIG. 3a) or <10 (FIG. 3b) as a function of dose of co-administered PDE2-i B-1a (0.63 to 10 mg/kg, s.c.; −1 h; closed symbols) or solvent (10 ml/kg, s.c.; −1 h; open symbols). The gray horizontal bar represents the $ED_{50}$ (and 95% confidence limits) of MP-10 (−1 h, s.c.) in the solvent group (FIG. 3a) or of MP-10 (−1 h, s.c.) alone (FIG. 3b; historical data).
Figure 3B:
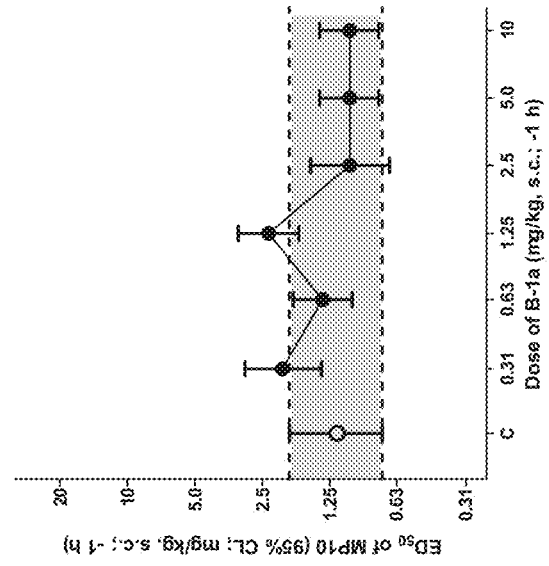

This is further illustrated in FIG. 3, which plots the $ED_{50}$ of MP-10 for inhibition of agitation to a score <21 (FIG. 3a) and to a score <10 (FIG. 3b) as a function of the dose of B-1a. The $ED_{50}$ of MP-10 for inhibition of agitation to a score <21 is hardly affected by the dose of the co-administered B-1a (FIG. 3a). However, the $ED_{50}$ of MP-10 for inhibition of agitation to a score <10 dose-dependently decreased with increasing dose of co-administered B-1a (FIG. 3b).

Figure 4A:
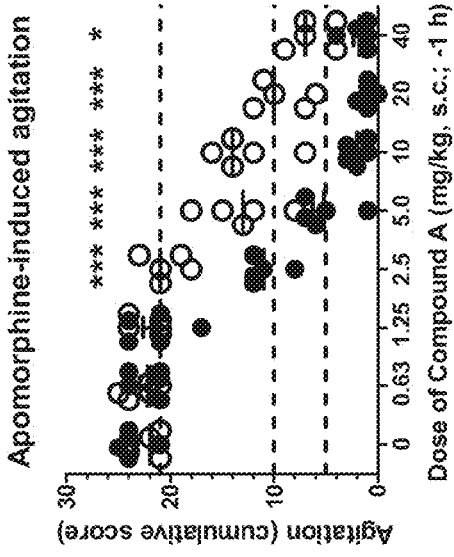
FIG. 4a) and Compound B (−1 h, s.c.
Figure 4B:
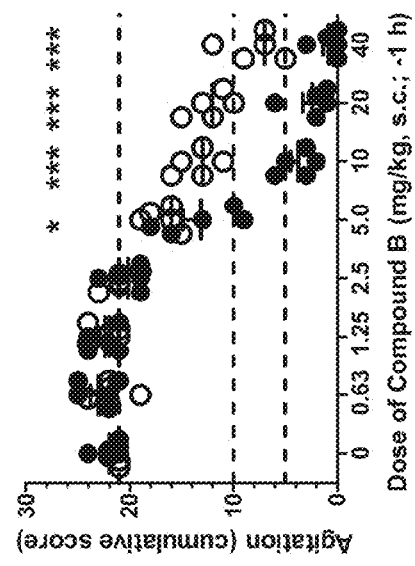
FIG. 4b) for inhibition of apomorphine-induced agitation. Shown are individual scores (open and closed circles for PDE2-i at 0 and 10 mg/kg, respectively) and median scores (horizontal lines) for agitation per dose group.
Figure 5A:
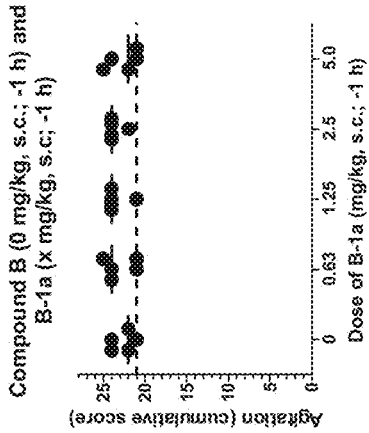
FIGS. 5a-d shows the dose-dependent effect of the PDE2-i B-1a (0, 0.63, 1.25, 2.5 and 5.0 mg/kg s.c.; −1 h) on apomorphine-induced agitation in the presence of standard doses of Compound A (0 or 2.5 mg/kg, s.c., −1 h.
Figure 5B:
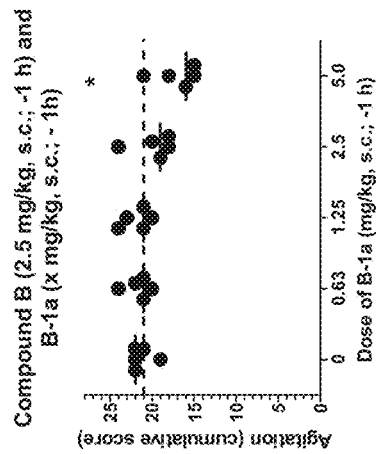
Figure 5C:
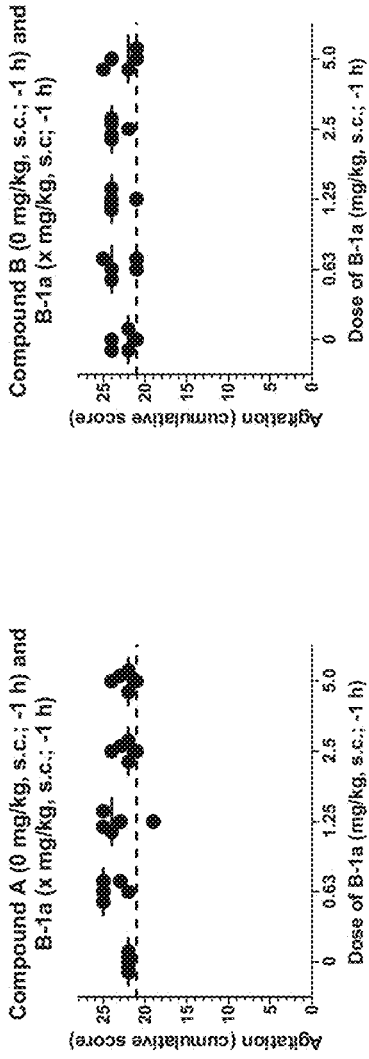
Figure 5D:
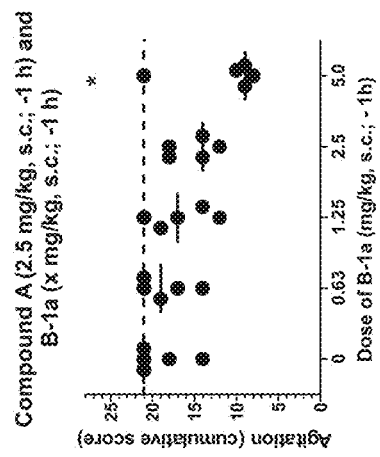

Inhibition of Apomorphine-Induced Agitation in Rats in Combination with Two Other PDE10-is, Viz. Compound A and Compound B In order to show that PDE2-is do not potentiate the effect of only MP-10 but also that of other PDE10-is, we have tested the interaction of B-1a with two additional PDE10-is, viz. Compound A and Compound B. FIG. 4 shows the effect of B-1a (0 vs. 10 mg/kg s.c.; −1 h) on the dose-response relations of Compound A (−1 h, s.c.; FIG. 4a) and Compound B (−1 h, s.c.; FIG. 4b) for inhibition of apomorphine-induced agitation. Shown are individual scores (open and closed circles for PDE2-i at 0 and 10 mg/kg, respectively) and median scores (horizontal lines) for agitation per dose group. $ED_{50}$s (and 95% confidence limits) of the PDE10-is for reducing agitation scores to <21, <10 and <5 have been listed for co-treatment with the PDE2-i at 0 and 10 mg/kg. B-1a potentiated the size of the effect of the PDE10-is without inducing a leftward shift in the dose-response curves. This is also reflected in the listed $ED_{50}$ values. B-1a did not affect the $ED_{50}$s of the PDE10-is for mild inhibition (score <21) but decreased the $ED_{50}$s of the PDE10-is for higher levels of inhibition (score <10 and score <5). FIG. 5 shows the dose-dependent effect of the PDE2-i B-1a (0, 0.63, 1.25, 2.5 and 5.0 mg/kg s.c.; −1 h) on apomorphine-induced agitation in the presence of standard doses of Compound A (0 or 2.5 mg/kg, s.c., −1 h; FIGS. 5a and 5c, respectively) or Compound B (0 or 2.5 mg/kg, s.c., −1 h; FIGS. 5b and 5d, respectively). The dotted horizontal line represents the criterion for mild inhibition of agitation (score <21). B-1a did not affect apomorphine-induced agitation when combined with the solvent of the PDE10-is (FIGS. 5a and b) but significantly potentiated the effect of both PDE10-is versus solvent at 5.0 mg/kg (FIGS. 5c and d, respectively)

d-Amphetamine-Induced Hyperlocomotion in Rats: Potentiation of the Effect of MP-10

Overnight starved, male Wiga Wistar rats (Charles River, Germany; 200-260 g) were used. At a predefined time interval before measuring motor activity, the rats were pretreated with test compound or solvent (10 ml/kg, p.o. or s.c.) and placed in individual cages. Thirty min before starting the locomotor activity test, the rats were challenged with d-amphetamine (1.25 mg/kg, s.c.) in combination with MP-10 (2.5 mg/kg, s.c.), both given as a single injection (10 ml/kg, s.c.). Motor activity was measured over a period of 30 min in microprocessor-based motor activity arenas (closed gray PVC cylinders with a height of 39 cm and a diameter of 31 cm) and analyzed using the Noldus Ethovision XT Video Tracking System (Version 7.0.418; Noldus, Wageningen, The Netherlands). The total distance traveled (cm) was calculated. A total distance traveled <2500 cm was adopted as all-or-none criterion for potentiation of the effect of MP-10 (6.3% false positives in a control population of 412 solvent-pretreated rats). The results of this test are shown in table 8 below.

TABLE 8

Inhibition of d-Amphetamine-induced Hyperlocomotion in Rats: potentiation of the effect of MP-10

| Co. No. | Route | Time | Dose of compound | Distance Total <2500 cm Effect |
|---|---|---|---|---|
| B-1a | SC | −60 | 0.31 | 3066 |
|  |  |  | 0.63 | 2525 |
|  |  |  | 1.25 | 1664 |
|  |  |  | 2.5 | 1659 |

TABLE 8-continued

Inhibition of d-Amphetamine-induced Hyperlocomotion in Rats: potentiation of the effect of MP-10

| Co. No. | Route | Time | Dose of compound | Distance Total <2500 cm Effect |
|---|---|---|---|---|
|  |  |  | 5 | 1281 |
|  |  |  | 10 | 727.6 |
| B-6 | PO | −60 | 10 | 5033 |
|  | SC | −60 | 0.63 | 3096 |
|  |  |  | 2.5 | 1206 |
|  |  |  | 10 | 743.7 |
| B-17 | SC | −60 | 2.5 | 4133 |
|  |  |  | 10 | 1721 |
| B-11 | SC | −60 | 2.5 | 3494 |
|  |  |  | 10 | 1960 |
| B-18 | SC | −60 | 10 | 3369 |
| B-26 | SC | −60 | 2.5 | 3061 |
|  |  |  | 10 | 1653 |
| B-27 | SC | −60 | 2.5 | 4145 |
|  |  |  | 10 | 2500 |
| B-25 | SC | −60 | 10 | 3921 |

A representation of the effects observed with MP-10, B-1a and B1-a in combination with MP-10 is provided in FIGS. 6a-c. FIG. 6a shows the dose-dependent inhibition of d-amphetamine-induced hyperlocomotion measured 1 h after s.c. injection of MP-10. Note that the effect is only partial, hardly reaching levels <2500 cm. FIG. 6b shows the absence of effect against d-amphetamine-induced hyperlocomotion measured 1 h after s.c. injection of B-1a at the tested dose of 40 mg/kg. FIG. 6c shows the dose-dependent potentiation of the effect of MP-10 (2.5 mg/kg, s.c.) on d-amphetamine-induced hyperlocomotion measured 1 h after s.c. injection of B-1a. While B-1a is ineffective per se at the tested dose of 40 mg/kg (FIG. 6b) and MP-10 alone (up to 40 mg/kg) almost never achieves values <2500 cm (FIG. 6a), B-1a potentiates the effect of a low dose of MP-10 (2.5 mg/kg) and consistently results in activity levels <2500 cm with an $ED_{50}$ of 0.51 mg/kg.

Figure 7:
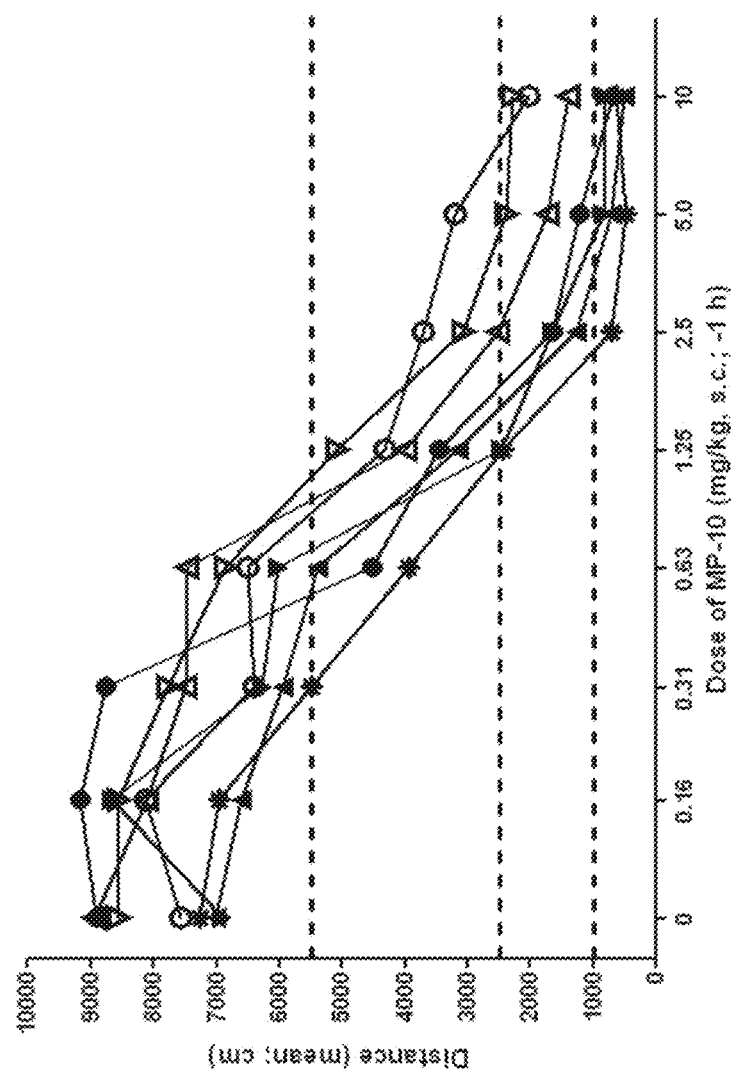
FIG. 7 shows the dose-dependent effect of MP-10 (−1 h, s.c.) on d-amphetamine-induced hyperlocomotion as a function of dose of co-administered PDE2-i B-1a (0.63 to 10 mg/kg, s.c.; −1 h) or solvent (10 ml/kg, s.c.; −1 h). The dotted horizontal bars reflect the critical levels for drug-induced effects (<5500 cm, <2500 cm and <1000 cm).

FIG. 7 shows the dose-dependent effect of MP-10 (−1 h, s.c.) on d-amphetamine-induced hyperlocomotion as a function of dose of co-administered PDE2-i B-1a (0.63 to 10 mg/kg, s.c.; −1 h) or solvent (10 ml/kg, s.c.; −1 h). The dotted horizontal bars reflect the critical levels for drug-induced effects (<5500 cm, <2500 cm and <1000 cm). B-1a dose-dependently potentiated the effect size obtained with MP-10.

This is also illustrated in FIG. 8. FIG. 8 plots the $ED_{50}$ (and 95% confidence limits) of MP-10 (−1 h, s.c.) for reducing d-amphetamine-induced hyperlocomotion to a distance <5500 cm (FIG. 8a), <2500 cm, (FIG. 8b) and <1000 cm (FIG. 8c) as a function of dose of co-administered B-1a (0.63 to 10 mg/kg, s.c.; −1 h; closed symbols) or solvent (10 ml/kg, s.c.; −1 h; open symbols). The gray horizontal bar represents the $ED_{50}$ (and 95% confidence limits) of MP-10 (−1 h, s.c.) combined with the solvent of B-1a (FIGS. 8a and b) or of MP-10 (−1 h, s.c.) alone (FIG. 8c; >40 mg/kg, historical data). B-1a hardly affected the $ED_{50}$ of MP-10 for reducing locomotion to a distance <5500 cm (FIG. 8a) but dose-dependently decreased the $ED_{50}$ of MP-10 for reducing locomotion to a distance <2500 cm and <1000 cm (FIGS. 8b and 8c, respectively).

Inhibition of d-Amphetamine-Induced Hyperlocomotion in Rats in Combination with Two Other PDE10-is, Viz. Compound A and Compound B In order to show that PDE2-is do not potentiate the effect of only MP-10 but also that of other PDE10-is, we have tested the interaction of B-1a with two additional PDE10-is, viz. Compound A and Compound B.

Figure 9A:
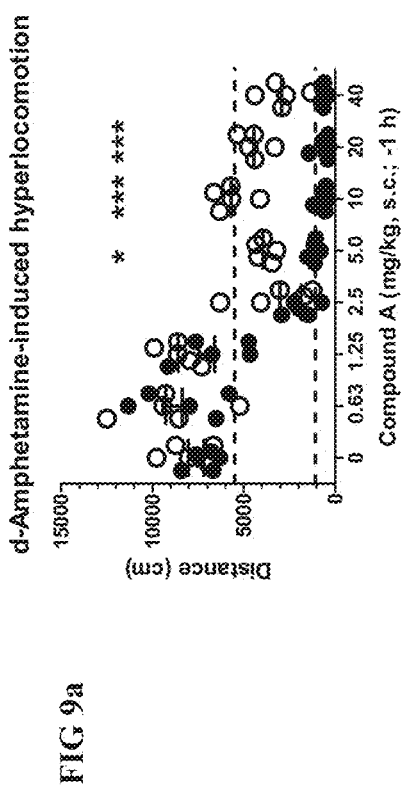
FIG. 9a) and Compound B (−1 h, s.c.
Figure 9B:
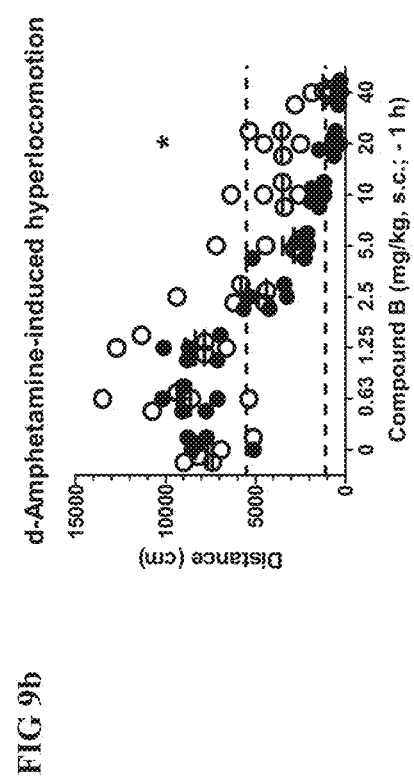
FIG. 9b) for inhibition of d-amphetamine-induced hyperlocomotion. Shown are individual values (open and closed circles for PDE2-i at 0 and 10 mg/kg, respectively) and median values (horizontal lines) for distance traveled per dose group. The dotted horizontal lines represent the criteria adopted for drug-induced effects (<5500 and <1100 cm).

FIG. 9 shows the effect of a standard dose of B-1a (0 vs. 10 mg/kg s.c.; −1 h) on the dose-response of Compound A (−1 h, s.c.; FIG. 9a) and Compound B (−1 h, s.c.; FIG. 9b) for inhibition of d-amphetamine-induced hyperlocomotion. Shown are individual values (open and closed circles for PDE2-i at 0 and 10 mg/kg, respectively) and median values (horizontal lines) for distance traveled per dose group. The dotted horizontal lines represent the criteria adopted for drug-induced effects (<5500 and <1100 cm). $ED_{50}$s (and 95% confidence limits) of the PDE10-is for reducing distance traveled to <5500 cm and to <1100 cm) have been listed for co-treatment with B-1a at 0 and 10 mg/kg. B-1a potentiated the size of the effect of the PDE10-is without inducing a leftward shift in dose-response curve. This is also reflected in the listed $ED_{50}$ values. B-1a did not affect the $ED_{50}$s of the PDE10-is for mild inhibition (distance <5500 cm) but markedly decreased the $ED_{50}$s of the PDE10-is for pronounced inhibition (<1100 cm).

FIG. 10 shows the effect of B-1a (0, 0.63, 1.25, 2.5 and 5.0 mg/kg s.c.; −1 h; FIG. 10a) on d-amphetamine-induced hyperlocomotion in the presence of standard doses of Compound A (0 or 2.5 mg/kg, s.c., −1 h; FIG. 10b) or Compound B (0 or 2.5 mg/kg, s.c., −1 h; FIG. 10c). The dotted horizontal lines represent the critical levels for drug-induced effects (<5500 cm and <1100 cm). B-1a potentiated the effect of both PDE10-is.

Potentiation of [$^3$H]B-1a Binding to PDE2 by MP-10

[$^3$H]B-1a is a radioligand binding selectively to the catalytic domain of the PDE2 enzyme. Using in vitro autoradiography, it has been shown that the distribution of [$^3$H] B-1a binding sites match perfectly with the PDE2 protein expression pattern in rat brain with high densities in the cortex, hippocampus, striatum and substantia nigra. When developing an in vivo occupancy assay of the PDE2 enzyme using [$^3$H]B-1a, it was observed that the PDE10 inhibitor MP-10 could dose-dependently potentiate the in vivo binding of the radioligand. The most plausible explanation of this phenomenon is the sensitivity of the PDE2 GAF domain to cGMP. Indeed, it has been described in literature that cGMP by binding to the PDE2 GAF domain change the conformation of the enzyme and increase the substrate accessibility to the catalytic domain (Pandit J et al., Proc. Natl. Acad. Sci. USA. 2009 Oct. 27; 106(43):18225-30) and most probably increase also the affinity of [$^3$H]B-1a. Therefore, MP-10, by increasing the intracellular concentration of cGMP, would stimulate the GAF domain of PDE2, change its conformation and increase the binding of [$^3$H]B-1a. To demonstrate this hypothesis, it was shown that cBIMP (a non hydrolysable analogue of cGMP) could increase the specific binding of [$^3$H]B-1a on rat brain sections. In addition, it was shown that pre-treatment with L-NAME (a nitric oxide inhibitor that reduce the intracellular concentration of cGMP) prevented the potentiation of [$^3$H]B-1a binding by the PDE10 inhibitor MP-10 demonstrating that this phenomenon is cGMP mediated.

TABLE 9

Influence of MP-10 on in vivo [$^3$H]B-1a binding expressed as % of binding in vehicle-treated rats

| dose MP-10 | AVG | | SEM | n |
|---|---|---|---|---|
| 0.63 mpk | 80 | ± | 28 | 3 |
| 2.5 mpk | 302 | ± | 57 | 3 |
| 10 mpk | 501 | ± | 29 | 3 |
| 40 mpk | 739 | ± | 68 | 3 |

Figure 11:
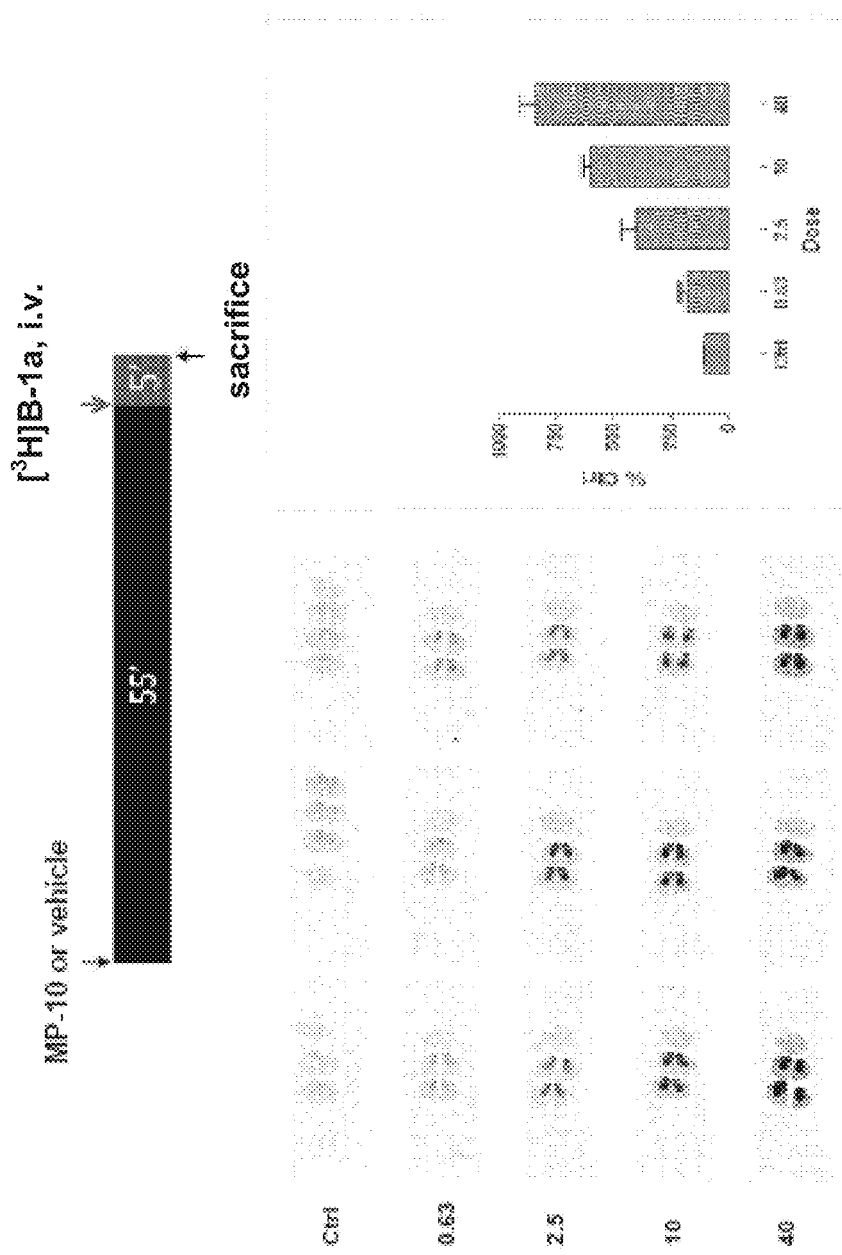
FIG. 11 shows the potentiation of [$^3$H]B1-a binding (administered intravenously, i.v.) to PDE2 by MP-10 by means of ex vivo autoradiography. Ctrl means control.

The data summarised in table 9 is also shown in FIG. 11, including ex vivo autoradiography images.

Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A pharmaceutical composition comprising a carrier and as first active ingredient a PDE2 inhibitor of the formula:

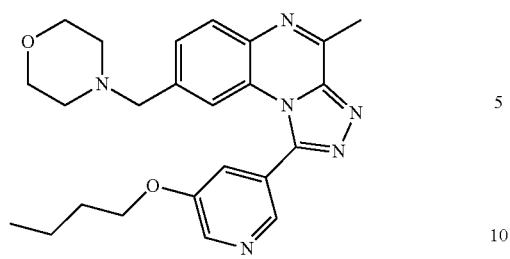
or a pharmaceutically acceptable salt thereof,
and as a second active ingredient a PDE10 inhibitor MP 10.
2. The pharmaceutical composition according to claim 1, wherein the first active ingredient, and the second active ingredient each are provided in a therapeutically effective amount.
* * * * *